(12) United States Patent
Knust et al.

(10) Patent No.: US 7,897,627 B2
(45) Date of Patent: Mar. 1, 2011

(54) HETEROARYL DERIVATIVES AS OREXIN RECEPTOR ANTAGONISTS

(75) Inventors: Henner Knust, Rheinfelden (DE); Matthias Nettekoven, Grenzach-Wyhlen (DE); Emmanuel Pinard, Linsdorf (FR); Olivier Roche, Folgensbourg (FR); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/334,559

(22) Filed: Dec. 15, 2008

(65) Prior Publication Data
US 2009/0163485 A1 Jun. 25, 2009

(30) Foreign Application Priority Data
Dec. 21, 2007 (EP) .................... 07150294

(51) Int. Cl.
| | |
|---|---|
| A61K 31/517 | (2006.01) |
| A61K 31/506 | (2006.01) |
| A61K 31/501 | (2006.01) |
| A61K 31/498 | (2006.01) |
| A61K 31/4439 | (2006.01) |
| A61K 31/427 | (2006.01) |
| A61K 31/428 | (2006.01) |
| A61K 31/4245 | (2006.01) |
| A61K 31/423 | (2006.01) |
| C07D 417/14 | (2006.01) |
| C07D 417/12 | (2006.01) |
| C07D 413/14 | (2006.01) |
| C07D 413/12 | (2006.01) |
| C07D 409/14 | (2006.01) |
| C07D 405/14 | (2006.01) |
| C07D 401/14 | (2006.01) |
| C07D 403/12 | (2006.01) |
| C07D 403/14 | (2006.01) |

(52) U.S. Cl. ............... 514/367; 514/375; 514/249; 514/266.2; 514/338; 514/364; 514/365; 514/275; 514/256; 514/252.05; 544/238; 544/292; 544/329; 544/332; 544/356; 548/131; 548/161; 548/222; 548/204; 546/271.7

(58) Field of Classification Search ........... 546/192; 548/517; 514/317, 422
See application file for complete search history.

(56) References Cited

U.S. PATENT DOCUMENTS

| | | |
|---|---|---|
| 2003/0176454 A1 | 9/2003 | Yamada et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |
| 2007/0219181 A1 | 9/2007 | Kimura et al. |
| 2008/0280948 A1 | 11/2008 | Baumann et al. |
| 2009/0181965 A1 | 7/2009 | Baumann et al. |

FOREIGN PATENT DOCUMENTS

| | | |
|---|---|---|
| EP | 1950211 | 7/2008 |
| WO | 9404487 | 3/1994 |
| WO | 9965884 | 12/1999 |
| WO | WO 0027842 A1 * | 5/2000 |
| WO | WO 01/47897 | 7/2001 |
| WO | 0187845 | 11/2001 |
| WO | WO 03/002561 | 1/2003 |
| WO | WO 2004/069185 | 8/2004 |
| WO | 2004110350 | 12/2004 |
| WO | 2005115990 | 12/2005 |
| WO | 2006058905 | 6/2006 |
| WO | 2006112550 | 10/2006 |
| WO | 2006112551 | 10/2006 |
| WO | WO 2006/111549 | 10/2006 |
| WO | 2007058304 | 5/2007 |
| WO | 2007058305 | 5/2007 |
| WO | 2007102580 | 9/2007 |
| WO | 2007135969 | 11/2007 |
| WO | 2007135970 | 11/2007 |
| WO | 2007139149 | 12/2007 |
| WO | 2008013213 | 1/2008 |
| WO | WO 2008065626 A2 * | 6/2008 |

OTHER PUBLICATIONS

Siegel, Annu Rev. Psychol. vol. 55, pp. 125-148 (2004).
Delecea et al., Proc. Natl. Acad. Sci. USA vol. 95 pp. 322-327 (1998).
Sakurai et al., Cell vol. 92, pp. 573-585 (1998).
Sakurai, Regulatory Peptides vol. 126 pp. 3-10 (2005).

(Continued)

Primary Examiner—Joseph R Kosack
Assistant Examiner—Matthew P Coughlin
(74) Attorney, Agent, or Firm—George W. Johnston; Patricia S. Rocha-Tramaloni; Kimberly J. Prior

(57) ABSTRACT

The present invention relates to compounds of formula

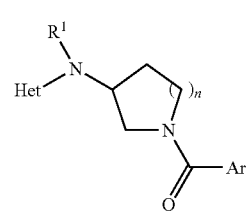

wherein
Ar, Het, $R^1$ and n are as defined herein and to pharmaceutically suitable acid addition salts, optically pure enantiomers, racemates or diastereomeric mixtures thereof. Compounds of formula I are orexin receptor antagonists and are useful in the treatment of sleep apnea, narcolepsy, insomnia, parasomnia, jet lag syndrome, circadian rhythms disorder and sleep disorders associated with neurological diseases.

25 Claims, No Drawings

OTHER PUBLICATIONS

Peyron et al., J. Neurosci. vol. 18, pp. 9996-10015 (1998).
Nambu et al., Brain Res. vol. 827 pp. 243-260 (1999).
Chemelli et al., Cell, vol. 98 pp. 437-451 (1999).
Lin et al., Cell. vol. 98 pp. 365-376 (1999).
Nishino et al., Lancet vol. 355 pp. 39-40 (2000).
Peyron et al., Nature Medicine vol. 6 pp. 991-997 (2000).
Mignot et al., Sleep vol. 11 pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Winsky Sommerer et al., J. Neuroscience vol. 24 pp. 11439-11448 (2004).
Chang et al., Neurosci. Res. vol. 56 pp. 356-362 (2006).
Suzuki et al., Brain Research vol. 1044, pp. 116-121 (2005).
Digby et al., J. Endocrinol. vol. 191 pp. 129-136 (2006).
Expert Opin. Ther. Patents vol. 16(5) pp. 631-646 (2006).
Current Opinion in Drug Discovery & Development vol. 9(5) pp. 551-559 (2006).
J. Neurosci. vol. 20(20) pp. 7760-7765 (2000).
Neurosci. Lett. vol. 341(3) pp. 256-258 (2003).
Malherbe et al., Mol. Pharmacol. vol. 64 pp. 823-832 (2003).
Weggen, et al., Nature vol. 414, pp. 212-216 (2001).
Morihara et al., J. Neurochem. vol. 83, pp. 1009-1012 (2002).
Jantzen et al., J. Neuroscience, vol. 22, pp. 226-254 (2002).
Takahashi et al., J Biol. Chem. vol. 278 pp. 18644-18670 (2003).
Beher et al., J. Biol. Chem. vol. 279 pp. 43419-43426 (2004).
Lleo et al., Nature Med. vol. 10, pp. 1065-1066 (2004).
Kukar et al., Nature Med. vol. 11 pp. 545-550 (2005).
Perretto et al., J. Med. Chem, vol. 48 pp. 5705-5720 (2005).
Clarke et al., J. Biol. Chem. vol. 281 pp. 31279-31289 (2006).
Stock et al., Bioorg. Med. Chem. Lett. vol. 16, pp. 2219-2223 (2006).
Narlawar et al., J. Med. Chem. vol. 49 pp. 7588-7591 (2006).
McPhee et al. J. Med. Chem. Soc. vol. 66 p. 1132 (1944).
Yang et al., J. Org. Chem. vol. 67(21) p. 7429 (2002).
Dorwald F. A., Side Reactions in Organic Synthesis 2005, Wiley, VCH Weinheim Preface & Chapter 1 included (pp. 1-16).
Kubinyi, 3D QSAR in Drug Design: Ligand Protein Interactions & Molecular Similarity vol. 2-3, Springer, 1998, 800 pgs. relevant pages attached (pp. 243-244).
Office Action mailed May 20, 2010 in copending U.S. Appl. No. 12/348,370.
Office Action mailed Jun. 28, 2010 in copending U.S. Appl. No. 12/114,852.

* cited by examiner

HETEROARYL DERIVATIVES AS OREXIN RECEPTOR ANTAGONISTS

PRIORITY TO RELATED APPLICATION(S)

This application claims the benefit of European Patent Application No. 07150294.2, filed Dec. 21, 2007, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al, *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al, *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Preproorexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al, *Cell*, 98, 365-376, 1999), (c) lack of OX-A and OX-B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracerebroventricular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al, *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R (N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

Numerous documents describe the current knowledge on orexin pathway, for example the following documents:

Expert Opin. Ther. Patents (2006), 16(5), 631-646
Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention provides compounds of formula I

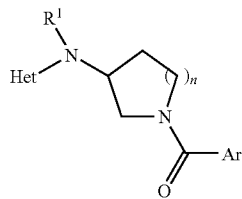

wherein

Ar is an unsubstituted or substituted aryl or heteroaryl group, wherein the substituted aryl and heteroaryl groups are substituted by one or more substituents $R^2$;

$R^2$ is hydroxy, halogen, lower alkyl, lower alkyl substituted by halogen, lower alkoxy, lower alkoxy substituted by halogen, C(O)-lower alkyl, nitro, NR'R", cyano, S-lower alkyl, $SO_2$-lower alkyl, cycloalkyl, heterocycloalkyl, phenyloxy, benzyloxy, phenyl, NH-phenyl or heteroaryl, wherein the phenyl and heteroaryl groups are unsubstituted or substituted by one or more substituents selected from lower alkyl and halogen;

R'/R" are each independently hydrogen or lower alkyl;

$R^1$ is hydrogen or lower alkyl;

Het is a heteroaryl group, unsubstituted or substituted by one or more substituents selected from $R^3$;

$R^3$ is hydroxy, halogen, =O, lower alkyl, lower alkyl substituted by halogen, lower alkoxy, phenyl, lower alkoxy substituted by halogen, nitro, cyano, $SO_2$-lower alkyl, cycloalkyl or heterocycloalkyl;

n is 1 or 2;

and pharmaceutically suitable acid addition salts, optically pure enantiomers, racemates or diastereomeric mixtures thereof.

Compounds of formula I are orexin receptor antagonists. The compounds of the invention can be used in the treatment of disorders in which orexin pathways are involved; like sleep disorders, including sleep apnea, narcolepsy, insomnia, parasomnia, jet lag syndrome, circadian rhythms disorder, and restless leg syndrome. The compounds are also useful for the treatment of psychiatric, neurological and neurodegenerative disorders, including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, and mental retardation. The compounds are also useful for the treatment of dyskinesias, such as Huntington's disease and Tourette syndrome, addictions, craving associated with drug abuse, seizure disorders, epilepsy, and metabolic diseases, such as obesity, diabetes, eating disorders, including anorexia and bulimia, asthma, migraine, pain, neuropathic pain, and sleep disorders associated with psychiatric, neurological and neurodegenerative disorders. The compounds further are useful for the treatment of neuropathic pain, enhanced or exaggerated sensitivity to pain, such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-4 carbon atoms, for example, methyl, ethyl, propyl, isopropyl, n-butyl, i-butyl, t-butyl and the like. The term "alkyl" denotes a straight- or branched-chain hydrocarbon group containing from 1-7 carbon atoms.

The term "lower alkoxy" denotes a group having an alkyl group as defined above, which is attached via an oxygen atom.

The term "cycloalkyl" denotes a monovalent carbocyclic radical of 3 to 10 carbon atoms, preferably 3 to 6 carbon atoms, such as cyclopropyl, cyclobutyl, cyclopentyl, or cyclohexyl. Cycloalkyl groups can optionally be substituted as described below in the description and claims.

The term "heterocycloalkyl" denotes a saturated cyclic group of three to six ring atoms which contains 1 or 2 heteroatoms selected from nitrogen, oxygen and sulphur with the remaining atoms being carbon atoms. Examples of heterocycloalkyl include but are not limited to tetrahydrofuran, pyrrolidine and morpholine.

The term "halogen" denotes chlorine, iodine, fluorine and bromine.

The term "aryl" means the monovalent cyclic aromatic hydrocarbon group having 6 to 10 ring atoms and consisting of one or more fused rings in which at least one ring is aromatic in nature. Examples of aryl radicals include, but are not limited to, phenyl, naphthyl, biphenyl, indanyl, anthraquinolyl, and the like.

The term "heteroalkyl" means a non-aromatic cyclic group, having at least one heteroatom selected from N, S and O with the rest of the ring atoms being carbon, for example pyrrolidinyl, morpholinyl, piperazinyl or piperidinyl;

"Heteroaryl" means the monovalent aromatic group having one or more rings incorporating one, two, or three heteroatoms within the ring (chosen from nitrogen, oxygen, or sulfur). Examples of heteroaryl radicals include, but are not limited to, imidazolyl, oxazolyl, pyrazolyl, 1,3-benzodioxol, [1,2,4]triazolyl, [1,2,4]oxadiazolyl, isoxazolyl, thiazolyl, thiophenyl, furanyl, pyridinyl, pyrazinyl, pyrimidinyl, pyridazinyl, pyrrolyl, quinolinyl, quinoxalinyl, quinazolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphtyridinyl, and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds are those, wherein Het is benzooxazolyl, for example the following compounds

[3-(6-chloro-benzooxazol-2-ylamino)-pyrrolidin-1-yl]-(2,6-dimethoxy-phenyl)-methanone;
[(R)-3-(6-chloro-benzooxazol-2-ylamino)-pyrrolidin-1-yl]-(2,6-dimethoxy-phenyl)-methanone;
[(R)-3-(6-chloro-benzooxazol-2-ylamino)-pyrrolidin-1-yl]-(2-pyrrol-1-yl-phenyl)-methanone;
[(R)-3-(6-chloro-benzooxazol-2-ylamino)-pyrrolidin-1-yl]-(2,6-dichloro-phenyl)-methanone;
[(R)-3-(6-chloro-benzooxazol-2-ylamino)-pyrrolidin-1-yl]-(2-chloro-6-methyl-phenyl)-methanone;
[(R)-3-(6-chloro-benzooxazol-2-ylamino)-pyrrolidin-1-yl]-(2-ethyl-phenyl)-methanone;
[(R)-3-(6-chloro-benzooxazol-2-ylamino)-pyrrolidin-1-yl]-(2-ethoxy-phenyl)-methanone;
[(R)-3-(6-chloro-benzooxazol-2-ylamino)-pyrrolidin-1-yl]-(2-methylsulfanyl-phenyl)-methanone;
[(R)-3-(6-chloro-benzooxazol-2-ylamino)-pyrrolidin-1-yl]-(2-difluoromethoxy-phenyl)-methanone;
[(R)-3-(6-chloro-benzooxazol-2-ylamino)-pyrrolidin-1-yl]-(2-furan-2-yl-phenyl)-methanone;
[(R)-3-(6-chloro-benzooxazol-2-ylamino)-pyrrolidin-1-yl]-(5-phenyl-isoxazol-4-yl)-methanone;
[(R)-3-(6-chloro-benzooxazol-2-ylamino)-pyrrolidin-1-yl]-[2-(2H-[1,2,4]triazol-3-yl)-phenyl]-methanone;
[(R)-3-(6-chloro-benzooxazol-2-ylamino)-pyrrolidin-1-yl]-(2-trifluoromethyl-phenyl)-methanone;
[(R)-3-(6-chloro-benzooxazol-2-ylamino)-pyrrolidin-1-yl]-(2-pyridin-3-yl-phenyl)-methanone;
[(R)-3-(6-chloro-benzooxazol-2-ylamino)-pyrrolidin-1-yl]-(5-methyl-3-phenyl-isoxazol-4-yl)-methanone;
[(R)-3-(6-chloro-benzooxazol-2-ylamino)-pyrrolidin-1-yl]-(5-methyl-2-trifluoromethyl-phenyl)-methanone;
[(R)-3-(6-chloro-benzooxazol-2-ylamino)-pyrrolidin-1-yl]-[2-(3-methyl-[1,2,4]oxadiazol-5-yl)-phenyl]-methanone;
[(R)-3-(6-chloro-benzooxazol-2-ylamino)-pyrrolidin-1-yl]-(2-thiophen-2-yl-phenyl)-methanone;
[(R)-3-(6-chloro-benzooxazol-2-ylamino)-pyrrolidin-1-yl]-(2-trifluoromethoxy-phenyl)-methanone;
[(R)-3-(6-chloro-benzooxazol-2-ylamino)-pyrrolidin-1-yl]-(2-fluoro-6-trifluoromethyl-phenyl)-methanone;
[(R)-3-(6-chloro-benzooxazol-2-ylamino)-pyrrolidin-1-yl]-(2,6-diethoxy-phenyl)-methanone;
[(R)-3-(6-chloro-benzooxazol-2-ylamino)-pyrrolidin-1-yl]-(3'-methyl-biphenyl-2-yl)-methanone;
[(R)-3-(6-chloro-benzooxazol-2-ylamino)-pyrrolidin-1-yl]-(2-methyl-4-phenyl-thiazol-5-yl)-methanone;
[(R)-3-(6-chloro-benzooxazol-2-ylamino)-pyrrolidin-1-yl]-(2-chloro-6-trifluoromethyl-phenyl)-methanone;
[(R)-3-(6-chloro-benzooxazol-2-ylamino)-pyrrolidin-1-yl]-[2-(1,1,2,2-tetrafluoro-ethoxy)-phenyl]-methanone;
[(R)-3-(6-chloro-benzooxazol-2-ylamino)-pyrrolidin-1-yl]-(2-thiophen-3-yl-phenyl)-methanone;
[(R)-3-(6-chloro-benzooxazol-2-ylamino)-pyrrolidin-1-yl]-(5-methyl-2-trifluoromethyl-furan-3-yl)-methanone;
[(R)-3-(6-chloro-benzooxazol-2-ylamino)-pyrrolidin-1-yl]-(2-fluoro-6-pyrrolidin-1-yl-phenyl)-methanone;
[(R)-3-(6,7-difluoro-benzooxazol-2-ylamino)-pyrrolidin-1-yl]-(2,6-dimethoxy-phenyl)-methanone;
(2,6-dimethoxy-phenyl)-[(R)-3-(6-fluoro-benzooxazol-2-ylamino)-pyrrolidin-1-yl]-methanone;
[(R)-3-(7-chloro-benzooxazol-2-ylamino)-pyrrolidin-1-yl]-(2,6-dimethoxy-phenyl)-methanone;
(2,6-dimethoxy-phenyl)-[(R)-3-(4-methyl-benzooxazol-2-ylamino)-pyrrolidin-1-yl]-methanone;
[(R)-3-(7-fluoro-benzooxazol-2-ylamino)-pyrrolidin-1-yl]-[2-(1,1,2,2-tetrafluoro-ethoxy)-phenyl]-methanone;
[(R)-3-(6,7-difluoro-benzooxazol-2-ylamino)-pyrrolidin-1-yl]-(2-trifluoromethoxy-phenyl)-methanone;
[(R)-3-(6,7-difluoro-benzooxazol-2-ylamino)-pyrrolidin-1-yl]-[2-(1,1,2,2-tetrafluoro-ethoxy)-phenyl]-methanone;
[(R)-3-(6,7-difluoro-benzooxazol-2-ylamino)-pyrrolidin-1-yl]-(5-methyl-2-trifluoromethyl-phenyl)-methanone;
[(R)-3-(6,7-difluoro-benzooxazol-2-ylamino)-pyrrolidin-1-yl]-(5-methyl-3-phenyl-isoxazol-4-yl)-methanone;
[(R)-3-(6,7-difluoro-benzooxazol-2-ylamino)-pyrrolidin-1-yl]-(2-methyl-5-phenyl-thiazol-4-yl)-methanone;
[(R)-3-(6-fluoro-benzooxazol-2-ylamino)-pyrrolidin-1-yl]-(2-trifluoromethoxy-phenyl)-methanone;
[(R)-3-(6-fluoro-benzooxazol-2-ylamino)-pyrrolidin-1-yl]-[2-(1,1,2,2-tetrafluoro-ethoxy)-phenyl]-methanone;
[(R)-3-(6-fluoro-benzooxazol-2-ylamino)-pyrrolidin-1-yl]-(5-methyl-2-trifluoromethyl-phenyl)-methanone; or
[(R)-3-(6-fluoro-benzooxazol-2-ylamino)-pyrrolidin-1-yl]-(2-methyl-5-phenyl-thiazol-4-yl)-methanone.

A further embodiment of the invention are compounds, wherein Het is benzooxazol and Ar is aryl that is unsubstituted or substituted by $R^2$.

A further embodiment of the invention are compounds, wherein Het is benzooxazol and Ar is heteroaryl that is unsubstituted or substituted by $R^2$.

Preferred compounds are further those, wherein Het is quinoxalinyl, for example the following compounds
(2,6-dimethoxy-phenyl)-[3-(quinoxalin-2-ylamino)-pyrrolidin-1-yl]-methanone;
(2,6-dimethoxy-phenyl)-[(R)-3-(quinoxalin-2-ylamino)-pyrrolidin-1-yl]-methanone;
[(R)-3-(6-chloro-quinoxalin-2-ylamino)-pyrrolidin-1-yl]-(2,6-dimethoxy-phenyl)-methanone;
(2,6-dimethoxy-phenyl)-[(R)-3-(6-fluoro-quinoxalin-2-ylamino)-pyrrolidin-1-yl]-methanone;
[(R)-3-(6,7-difluoro-quinoxalin-2-ylamino)-pyrrolidin-1-yl]-(2-trifluoromethyl-phenyl)-methanone;
[(R)-3-(6,7-difluoro-quinoxalin-2-ylamino)-pyrrolidin-1-yl]-(2-trifluoromethoxy-phenyl)-methanone;
[(R)-3-(6,7-difluoro-quinoxalin-2-ylamino)-pyrrolidin-1-yl]-[2-(1,1,2,2-tetrafluoro-ethoxy)-phenyl]-methanone;
[(R)-3-(6,7-difluoro-quinoxalin-2-ylamino)-pyrrolidin-1-yl]-(5-methyl-3-phenyl-isoxazol-4-yl)-methanone;
[(R)-3-(6,7-difluoro-quinoxalin-2-ylamino)-pyrrolidin-1-yl]-[2-(3-methyl-[1,2,4]oxadiazol-5-yl)-phenyl]-methanone;
(2-chloro-5-methyl-phenyl)-[(R)-3-(6,7-difluoro-quinoxalin-2-ylamino)-pyrrolidin-1-yl]-methanone;
[(R)-3-(6,7-difluoro-quinoxalin-2-ylamino)-pyrrolidin-1-yl]-(2-methoxy-5-methyl-phenyl)-methanone;
[(R)-3-(6,7-difluoro-quinoxalin-2-ylamino)-pyrrolidin-1-yl]-(2-methyl-5-phenyl-thiazol-4-yl)-methanone;
[(R)-3-(6-chloro-quinoxalin-2-ylamino)-pyrrolidin-1-yl]-[2-(1,1,2,2-tetrafluoro-ethoxy)-phenyl]-methanone;
[(R)-3-(6-chloro-quinoxalin-2-ylamino)-pyrrolidin-1-yl]-(5-methyl-2-trifluoromethyl-phenyl)-methanone;
[(R)-3-(6-chloro-quinoxalin-2-ylamino)-pyrrolidin-1-yl]-(5-methyl-3-phenyl-isoxazol-4-yl)-methanone;
[(R)-3-(6-chloro-quinoxalin-2-ylamino)-pyrrolidin-1-yl]-[2-(3-methyl-[1,2,4]oxadiazol-5-yl)-phenyl]-methanone;
(2-chloro-5-methyl-phenyl)-[(R)-3-(6-chloro-quinoxalin-2-ylamino)-pyrrolidin-1-yl]-methanone;
[(R)-3-(6-chloro-quinoxalin-2-ylamino)-pyrrolidin-1-yl]-(2-methyl-5-phenyl-thiazol-4-yl)-methanone;
[(R)-3-(quinoxalin-2-ylamino)-pyrrolidin-1-yl]-(2-trifluoromethyl-phenyl)-methanone;
[(R)-3-(quinoxalin-2-ylamino)-pyrrolidin-1-yl]-(2-trifluoromethoxy-phenyl)-methanone;

[(R)-3-(quinoxalin-2-ylamino)-pyrrolidin-1-yl]-[2-(1,1,2,2-tetrafluoro-ethoxy)-phenyl]-methanone;
(5-methyl-2-trifluoromethyl-phenyl)-[(R)-3-(quinoxalin-2-ylamino)-pyrrolidin-1-yl]-methanone;
(2-methyl-5-phenyl-thiazol-4-yl)-[(R)-3-(quinoxalin-2-ylamino)-pyrrolidin-1-yl]-methanone;
[(R)-3-(7-chloro-quinoxalin-2-ylamino)-pyrrolidin-1-yl]-[2-(1,1,2,2-tetrafluoro-ethoxy)-phenyl]-methanone;
(R)-3-(6-tert-butyl-quinoxalin-2-ylamino)-pyrrolidin-1-yl]-(5-methyl-2-trifluoromethyl-phenyl)-methanone;
(R)-3-(6-fluoro-quinoxalin-2-ylamino)-pyrrolidin-1-yl]-(5-methyl-2-trifluoromethyl-phenyl)-methanone;
(R)-3-(7-chloro-6-methyl-quinoxalin-2-ylamino)-pyrrolidin-1-yl]-(5-methyl-2-trifluoromethyl-phenyl)-methanone; or
(R)-3-(6-Chloro-7-methyl-quinoxalin-2-ylamino)-pyrrolidin-1-yl]-(5-methyl-2-trifluoromethyl-phenyl)-methanone.

A further embodiment of the invention are compounds, wherein Het is quinoxalin and Ar is aryl that is unsubstituted or substituted by $R^2$.

A further embodiment of the invention are compounds, wherein Het is quinoxalin and Ar is heteroaryl that is unsubstituted or substituted by $R^2$.

Preferred compounds are further those, wherein Het is benzothiazolyl, for example the following compounds
[3-(6-Chloro-benzothiazol-2-ylamino)-pyrrolidin-1-yl]-(2,6-dimethoxy-phenyl)-methanone;
[(R)-3-(6-chloro-benzothiazol-2-ylamino)-pyrrolidin-1-yl]-(2,6-dimethoxy-phenyl)-methanone;
[(R)-3-(4-chloro-benzothiazol-2-ylamino)-pyrrolidin-1-yl]-(2,6-dimethoxy-phenyl)-methanone;
(2,6-dimethoxy-phenyl)-[(R)-3-(6-fluoro-benzothiazol-2-ylamino)-pyrrolidin-1-yl]-methanone;
(2,6-dimethoxy-phenyl)-[(R)-3-(4-fluoro-benzothiazol-2-ylamino)-pyrrolidin-1-yl]-methanone;
(2,6-dimethoxy-phenyl)-[(R)-3-(7-fluoro-benzothiazol-2-ylamino)-pyrrolidin-1-yl]-methanone;
[(R)-3-(5,7-difluoro-benzothiazol-2-ylamino)-pyrrolidin-1-yl]-(2,6-dimethoxy-phenyl)-methanone;
[(R)-3-(6-fluoro-benzothiazol-2-ylamino)-pyrrolidin-1-yl]-(2-trifluoromethyl-phenyl)-methanone;
[(R)-3-(6-fluoro-benzothiazol-2-ylamino)-pyrrolidin-1-yl]-(2-trifluoromethoxy-phenyl)-methanone;
[(R)-3-(6-fluoro-benzothiazol-2-ylamino)-pyrrolidin-1-yl]-[2-(1,1,2,2-tetrafluoro-ethoxy)-phenyl]-methanone;
[(R)-3-(6-fluoro-benzothiazol-2-ylamino)-pyrrolidin-1-yl]-(5-methyl-2-trifluoromethyl-phenyl)-methanone;
[(R)-3-(6-fluoro-benzothiazol-2-ylamino)-pyrrolidin-1-yl]-(5-methyl-3-phenyl-isoxazol-4-yl)-methanone;
[(R)-3-(6-fluoro-benzothiazol-2-ylamino)-pyrrolidin-1-yl]-[2-(3-methyl-[1,2,4]oxadiazol-5-yl)-phenyl]-methanone;
(2-chloro-5-methyl-phenyl)-[(R)-3-(6-fluoro-benzothiazol-2-ylamino)-pyrrolidin-1-yl]-methanone;
[(R)-3-(6-fluoro-benzothiazol-2-ylamino)-pyrrolidin-1-yl]-(2-methyl-5-phenyl-thiazol-4-yl)-methanone;
[(R)-3-(4-fluoro-benzothiazol-2-ylamino)-pyrrolidin-1-yl]-(2-trifluoromethoxy-phenyl)-methanone;
[(R)-3-(4-fluoro-benzothiazol-2-ylamino)-pyrrolidin-1-yl]-[2-(1,1,2,2-tetrafluoro-ethoxy)-phenyl]-methanone;
[(R)-3-(4-fluoro-benzothiazol-2-ylamino)-pyrrolidin-1-yl]-(5-methyl-2-trifluoromethyl-phenyl)-methanone;
[(R)-3-(4-fluoro-benzothiazol-2-ylamino)-pyrrolidin-1-yl]-[2-(3-methyl-[1,2,4]oxadiazol-5-yl)-phenyl]-methanone;
[(R)-3-(5,7-difluoro-benzothiazol-2-ylamino)-pyrrolidin-1-yl]-[2-(1,1,2,2-tetrafluoro-ethoxy)-phenyl]-methanone;
[(R)-3-(5,7-difluoro-benzothiazol-2-ylamino)-pyrrolidin-1-yl]-(5-methyl-3-phenyl-isoxazol-4-yl)-methanone;
[(R)-3-(5,7-difluoro-benzothiazol-2-ylamino)-pyrrolidin-1-yl]-[2-(3-methyl-[1,2,4]oxadiazol-5-yl)-phenyl]-methanone;
[(R)-3-(5,6-difluoro-benzothiazol-2-ylamino)-pyrrolidin-1-yl]-(5-methyl-2-trifluoromethyl-phenyl)-methanone; or
(R)-3-(4-chloro-benzothiazol-2-ylamino)-pyrrolidin-1-yl]-(5-methyl-2-trifluoromethyl-phenyl)-methanone.

A further embodiment of the invention are compounds, wherein Het is benzothiazol and Ar is aryl that is unsubstituted or substituted by $R^2$.

A further embodiment of the invention are compounds, wherein Het is benzothiazol and Ar is heteroaryl that is unsubstituted or substituted by $R^2$.

Preferred compounds are further those, wherein Het is pyrimidinyl, for example the following compound
(5-methyl-2-trifluoromethyl-phenyl)-[(R)-3-(2-phenyl-pyrimidin-4-ylamino)-pyrrolidin-1-yl]-methanone.

A further embodiment of the invention are compounds, wherein Het is pyrimidin and Ar is aryl that is unsubstituted or substituted by $R^2$.

A further embodiment of the invention are compounds, wherein Het is pyrimidin and Ar is heteroaryl that is unsubstituted or substituted by $R^2$.

The present compounds of formula I and their pharmaceutically acceptable salts can be prepared by methods known in the art, for example, by processes described below, which process comprises a) reacting a compound of formula

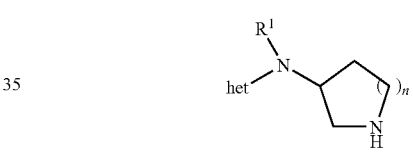

II with an acid chloride of formula

III to obtain the compound of formula

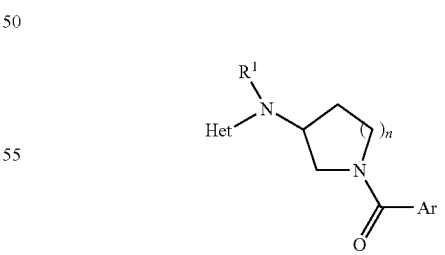

I wherein the substituents are as described above, and
if desired, converting the compounds obtained into pharmaceutically acceptable acid addition salts.

General Experimental Procedure:
The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

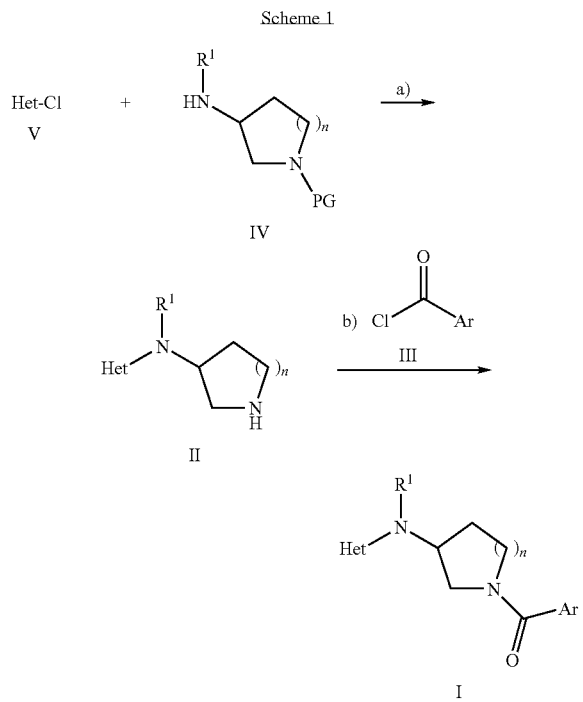

Step a)

Aromatic heterocyclic compounds (Het-Cl) V are either commercially available or can be synthesized according to procedures described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999) for instance from their respective HET-OH derivatives. Protected amino piperidines or pyrrolidines (IV, $R^1$=H) are commercially available or can be synthesized according to procedures described in literature. Protected amino piperidines or pyrrolidines (IV, $R^1$=H) can conveniently be converted by reductive amination with suitable aldehydes to protected amino piperidines or pyrrolidines (IV, $R^1$=lower alkyl) which can be reacted with Het-Cl V in the presence or absence of a solvent and the presence or the absence of a base. There is no particular restriction on the nature of the solvent to be employed, provided that it has no adverse effect on the reaction or the reagents involved and that it can dissolve the reagents, at least to some extent. Examples for suitable solvents include dichloromethane (DCM), dimethylformamide (DMF), tetrahydrofuran (THF) and the like. There is no particular restriction on the nature of the base used in this stage, and any base commonly used in this type of reaction can equally be employed here. Examples of such bases include $NEt_3$, DIPEA and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the protected intermediate (convenient PG=Boc) which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include dichloromethane (DCM), dioxane, tetrahydrofuran (THF) and the like. There is no particular restriction on the nature of the acid used in this stage, and any acid commonly used in this type of reaction can equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield amino piperidine or pyrrolidine derivatives IV.

Step b)

Transformation of intermediate amino piperidine or pyrrolidine derivatives II with acids (under coupling conditions with a coupling agent) or acid chlorides is well know in the art. For analogous examples in literature refer to Comprehensive Organic Transformations: A Guide to Functional Group Preparations, 2nd Edition, Richard C. Larock. John Wiley & Sons, New York, N.Y. 1999. However, we find it convenient to react intermediate amino piperidine or pyrrolidine derivatives II with acid chlorides in the presence or absence of a base and the presence or absence of a solvent. There is no particular restriction on the nature of the solvent to be employed, provided that it has no adverse effect on the reaction or the reagents involved and that it can dissolve the reagents, at least to some extent. Examples for suitable solvents include dichloromethane (DCM), dimethylformamide (DMF), tetrahydrofuran (THF) and the like. There is no particular restriction on the nature of the base used in this stage, and any base commonly used in this type of reaction can equally be employed here. Examples of such bases include pyridine, $NEt_3$, DIPEA and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield amino piperidine or pyrrolidine derivatives I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1×) with GlutaMax™1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 μg/ml penicillin and 100 μg/ml streptomycin. The cells were seeded at $5×10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 μM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., Mol. Pharmacol., 64, 823-832, 2003). Orexin A (catalog No. 1455, Toris Cookson Ltd, Bristol, UK) was used as agonist. Orexin A (50 mM stock solution in DMSO) was diluted in FLIPR buffer+0.1% BSA. The $EC_{50}$ and $EC_{80}$ values of orexin-A were measured daily from standard agonist concentration-response curves in CHO(dHFr-)-OX1R and -OX2R cell lines. All compounds were dissolved in 100% DMSO. Inhibition curves were determined by addition of 11 concentrations (0.0001-10 μM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{nH})$, where $n_H$=slope factor using Excel-fit 4 software (Microsoft).

$K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

The compounds show a $K_b$ value (μM)<1.0 in human on orexin receptor. The preferred compounds show a $K_b$ value<0.5 μM. Values for representative compounds are provided in the table below.

| Example | $K_b$ (μM) OX2R (human) |
|---|---|
| 1 | 0.0279 |
| 5 | 0.0242 |
| 6 | 0.0104 |
| 7 | 0.0228 |
| 24 | 0.0415 |
| 25 | 0.0163 |
| 28 | 0.0096 |
| 33 | 0.0354 |
| 35 | 0.045 |
| 41 | 0.0302 |
| 43 | 0.0015 |
| 45 | 0.0031 |
| 47 | 0.0377 |
| 52 | 0.0249 |
| 53 | 0.0299 |
| 56 | 0.047 |
| 57 | 0.0025 |
| 61 | 0.0054 |
| 62 | 0.014 |
| 63 | 0.0219 |
| 65 | 0.0272 |
| 67 | 0.0051 |
| 68 | 0.0018 |
| 69 | 0.0155 |
| 70 | 0.0024 |
| 71 | 0.0097 |
| 72 | 0.0298 |
| 73 | 0.0012 |
| 75 | 0.0163 |
| 78 | 0.0145 |
| 79 | 0.0173 |
| 82 | 0.0041 |
| 84 | 0.0056 |
| 86 | 0.0169 |
| 90 | 0.0186 |
| 92 | 0.0029 |
| 93 | 0.0164 |
| 94 | 0.0091 |
| 95 | 0.0426 |
| 97 | 0.0063 |
| 100 | 0.01 |
| 102 | 0.0144 |
| 106 | 0.0129 |
| 110 | 0.0319 |
| 112 | 0.0344 |
| 113 | 0.0217 |
| 114 | 0.002 |
| 115 | 0.0068 |
| 116 | 0.0261 |
| 117 | 0.0197 |
| 118 | 0.039 |
| 120 | 0.0188 |
| 122 | 0.0193 |
| 123 | 0.0032 |
| 124 | 0.0363 |
| 126 | 0.0144 |
| 132 | 0.016 |
| 134 | 0.0228 |
| 135 | 0.0394 |
| 141 | 0.0138 |
| 148 | 0.0386 |
| 149 | 0.0072 |
| 150 | 0.0136 |
| 151 | 0.0355 |
| 155 | 0.0304 |
| 157 | 0.0247 |
| 158 | 0.0039 |
| 159 | 0.0205 |
| 164 | 0.047 |
| 165 | 0.0185 |
| 166 | 0.009 |
| 167 | 0.001 |
| 168 | 0.0038 |
| 169 | 0.0021 |
| 170 | 0.0129 |
| 171 | 0.0245 |
| 172 | 0.0032 |
| 175 | 0.0187 |
| 176 | 0.014 |
| 177 | 0.0423 |
| 178 | 0.0244 |
| 181 | 0.028 |

-continued

| Example | $K_b$ (µM) OX2R (human) |
|---|---|
| 182 | 0.027 |
| 183 | 0.02 |
| 184 | 0.0021 |
| 185 | 0.0075 |
| 189 | 0.028 |
| 192 | 0.0324 |
| 200 | 0.0073 |
| 202 | 0.0046 |
| 203 | 0.008 |
| 204 | 0.0052 |
| 207 | 0.0046 |
| 212 | 0.0086 |
| 213 | 0.0371 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

[3-(6-Chloro-benzooxazol-2-ylamino)-pyrrolidin-1-yl]-(2,6-dimethoxy-phenyl)-methanone

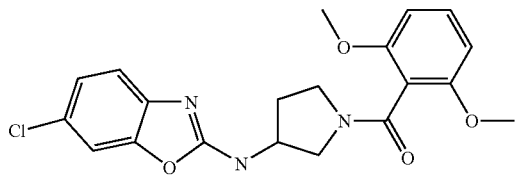

a) Step 1: (6-Chloro-benzooxazol-2-yl)-pyrrolidin-3-yl-amine; hydrochloride

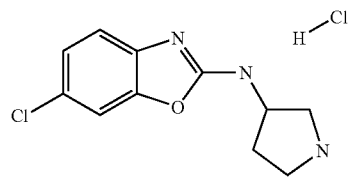

A mixture of 470 mg (2.5 mmol) 2,6-dichloro-benzooxazole (commercially available), 511 mg (2.75 mmol) 3-amino-pyrrolidine-1-carboxylic acid tert-butyl ester (commercially available) and 328 mg (3.25 mmol) NEt$_3$ in 8 mL DCM was stirred at room temperature over night. KHSO$_4$ aq (1N) was added and the organic layer was evaporated under reduced pressure. The residue was taken up in 10 mL HCl in dioxane (4N) and concentrated under reduced pressure to yield the crude title compound which was used without further purification in the consecutive step. (MH$^+$) 238.0.

b) Step 2: [3-(6-Chloro-benzooxazol-2-ylamino)-pyrrolidin-1-yl]-(2,6-dimethoxy-phenyl-methanone A mixture of 110 mg (6-chloro-benzooxazol-2-yl)-pyrrolidin-3-yl-amine; hydrochloride (crude) and 120 mg (0.6 mmol) 2,6-dimethoxybenzoyl chloride in 1.6 mL pyridine was stirred at room temperature over night. The mixture was evaporated and subjected to preparative HPLC purification on reversed phase eluting with a gradient formed from acetonitrile, water and NEt$_3$. The combined product containing fractions were evaporated to yield 1.6 mg of the title compound. (MH$^+$) 402.2.

EXAMPLE 2

[3-(Benzooxazol-2-ylamino)-pyrrolidin-1-yl]-(2,6-dimethoxy-phenyl)-methanone

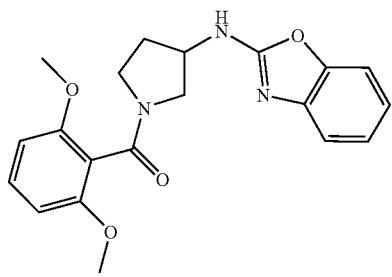

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2-chloro-benzooxazole (commercially available), 3-amino-pyrrolidine-1-carboxylic acid tert-butyl ester (commercially available) and 2,6-dimethoxybenzoyl chloride (commercially available). (MH$^+$) 368.2

EXAMPLE 3

[3-(6-Chloro-benzooxazol-2-ylamino)-pyrrolidin-1-yl]-(5-chloro-2-methoxy-phenyl)-methanone

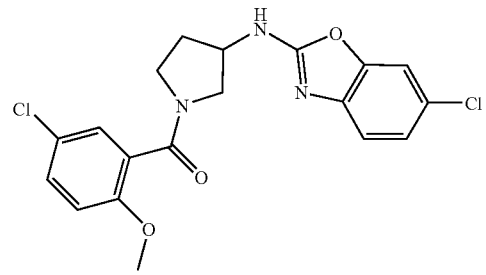

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzooxazole (commercially available), 3-amino-pyrrolidine-1-carboxylic acid tert-butyl ester (commercially available) and 5-chloro-2-methoxy-benzoyl chloride (commercially available). (MH$^+$) 406.1

EXAMPLE 4

[3-(Benzooxazol-2-ylamino)-pyrrolidin-1-yl]-(5-chloro-2-methoxy-phenyl)-methanone

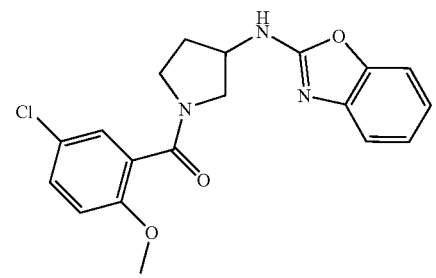

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2-chloro-benzooxazole (commercially available), 3-amino-pyrrolidine-1-carboxylic acid tert-butyl ester (commercially available) and 5-chloro-2-methoxy-benzoyl chloride (commercially available). (MH$^+$) 372.2.

EXAMPLE 5

[(R)-3-(6-Chloro-benzooxazol-2-ylamino)-pyrrolidin-1-yl]-(2,6-dimethoxy-phenyl)-methanone

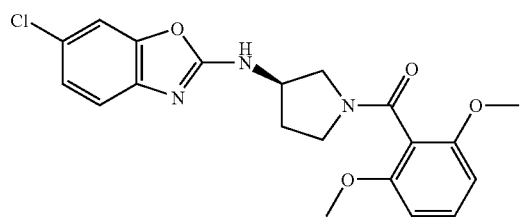

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzooxazole (commercially available), 3-(R)-amino-pyrrolidine-1-carboxylic acid tert-butyl ester (commercially available) and 2,6-dimethoxybenzoyl chloride (commercially available). (MH+) 402.2.

EXAMPLE 6

(2,6-Dimethoxy-phenyl)-[3-(quinoxalin-2-ylamino)-pyrrolidin-1-yl]-methanone

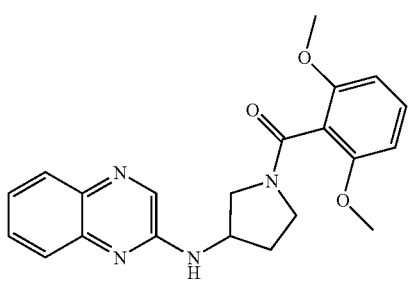

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2-chloro-quinoxaline (commercially available), 3-amino-pyrrolidine-1-carboxylic acid tert-butyl ester (commercially available) (coupling at elevated temperature) and 2,6-dimethoxybenzoyl chloride (commercially available). (MH+) 379.2.

EXAMPLE 7

[3-(6-Chloro-benzothiazol-2-ylamino)-pyrrolidin-1-yl]-(2,6-dimethoxy-phenyl)-methanone

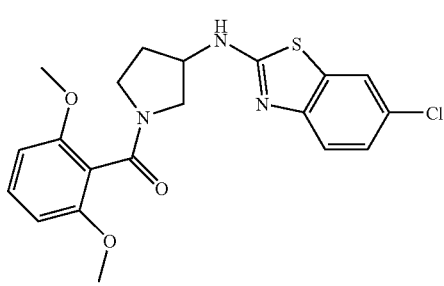

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzothiazole (commercially available), 3-amino-pyrrolidine-1-carboxylic acid tert-butyl ester (commercially available) and 2,6-dimethoxybenzoyl chloride (commercially available). (MH+) 418.2.

EXAMPLE 8

[3-(6-Chloro-benzooxazol-2-ylamino)-piperidin-1-yl]-(2,6-dimethoxy-phenyl)-methanone

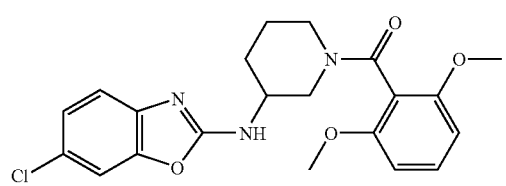

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzooxazole (commercially available), 3-amino-piperidine-1-carboxylic acid tert-butyl ester (commercially available) and 2,6-dimethoxybenzoyl chloride (commercially available). (MH+) 416.2.

EXAMPLE 9

[3-(6-Chloro-quinolin-2-ylamino)-piperidin-1-yl]-(2,6-dimethoxy-phenyl)-methanone

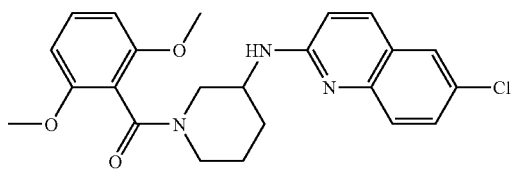

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-quinoline (commercially available), 3-amino-piperidine-1-carboxylic acid tert-butyl ester (commercially available) and 2,6-dimethoxybenzoyl chloride (commercially available). (MH+) 426.2.

EXAMPLE 10

(5-Chloro-2-methoxy-phenyl)-[3-(quinoxalin-2-ylamino)-pyrrolidin-1-yl]-methanone

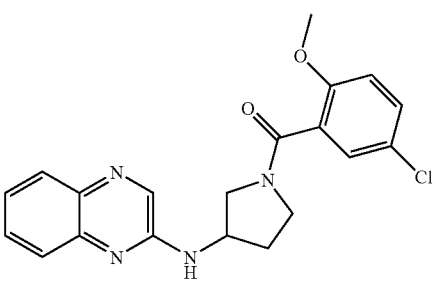

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2-chloro-quinoxaline (commercially available), 3-amino-pyrrolidine-1-carboxylic acid tert-butyl ester (commercially available) and 5-chloro-2-methoxy-benzoyl chloride (commercially available). (MH+) 383.2.

EXAMPLE 11

[3-(6-Chloro-benzothiazol-2-ylamino)-pyrrolidin-1-yl]-(5-chloro-2-methoxy-phenyl)-methanone

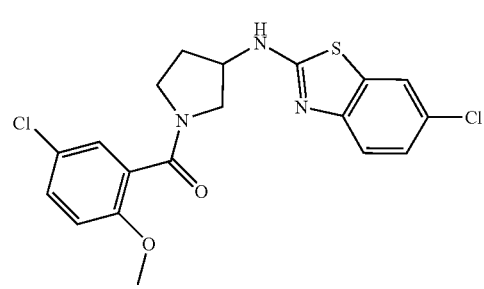

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzothiazole (commercially available), 3-amino-pyrrolidine-1-carboxylic acid tert-butyl ester (commercially available) and 5-chloro-2-methoxy-benzoyl chloride (commercially available). (MH+) 422.1.

EXAMPLE 12

[3-(6-Chloro-benzooxazol-2-ylamino)-piperidin-1-yl]-(5-chloro-2-methoxy-phenyl)-methanone

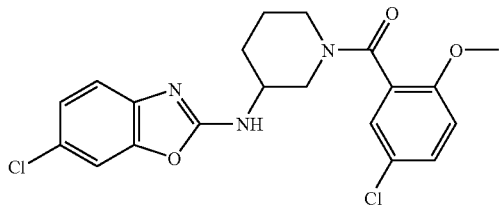

In analogy to the procedure described for the synthesis of [3-(6-chloro-benzooxazol-2-ylamino)-pyrrolidin-1-yl]-(2,6-dimethoxy-phenyl)-methanone (example 1) the title compound was prepared from 2,6-dichloro-benzooxazole (commercially available), 3-amino-piperidine-1-carboxylic acid tert-butyl ester (commercially available) and 5-chloro-2-methoxy-benzoyl chloride (commercially available). (MH+) 420.1.

EXAMPLE 13

[(R)-3-(6-Chloro-benzooxazol-2-ylamino)-piperidin-1-yl]-(2,6-dimethoxy-phenyl)-methanone

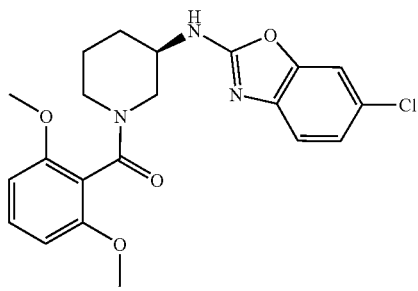

a) Step 1: ((R)-3-Amino-piperidin-1-yl)-(2,6-dimethoxy-phenyl)-methanone

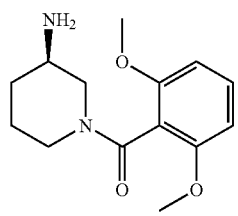

A mixture of 0.143 g (0.786 mmol) 2,6-dimethoxybenzoic acid (commercially available), 0.15 g (0.749 mmol) (R)-piperidin-3-yl-carbamic acid tert-butyl ester (commercially available), 0.264 g (0.824 mmol) TBTU and 0.145 g (1.123 mmol) DIPEA in 9.2 mL DMF was stirred at room tempera- ture over night. DMF was evaporated and the residue was purified by preparative HPLC on reversed phase eluting with a gradient formed from acetonitrile, water and formic acid. The product containing fractions were evaporated and the residue was treated with 4N HCl in dioxane and stirred at 50° C. over night. The mixture was evaporated to dryness and treated with NaHCO$_3$ aq. and DCM. The organic layer was separated, dried with MgSO$_4$ and evaporated to yield 22 mg (11%) of the title compound as colourless oil. (MH+) 265.1.

b) Step 2

A mixture of 22 mg (0.083 mmol) ((R)-3-Amino-piperidin-1-yl)-(2,6-dimethoxy-phenyl)-methanone, 15.6 mg (0.083 mmol) 2,6-dichlorobenzoxazole and 12.6 mg (0.125 mmol) NEt$_3$ in 3 mL DCM was stirred at room temperature over night. The mixture was evaporated to dryness and the residue was purified by preparative HPLC on reversed phase eluting with a gradient formed from acetonitrile, water and formic acid. The product containing fractions were evaporated to yield 12 mg (35%) of the title compound as colourless oil. (MH+) 416.2.

EXAMPLE 14

[(R)-3-(6-Chloro-benzooxazol-2-ylamino)-pyrrolidin-1-yl]-o-tolyl-methanone

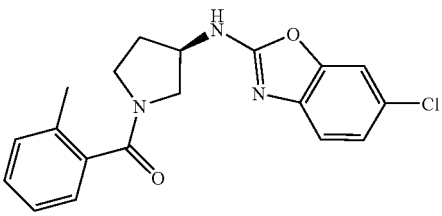

A mixture of 32.9 mg (0.12 mmol) (6-Chloro-benzooxazol-2-yl)-pyrrolidin-3-yl-amine; hydrochloride, 19.6 mg (0.144 mmol) 2-methyl-benzoic acid, 53.9 mg (0.168 mmol) TBTU and 77.5 mg (0.6 mmol) DIPEA in 2 mL DMF was stirred at room temperature for 16 h. The mixture was concentrated, taken up in methanol and formic acid and subjected to purification by preparative HPLC on reversed phase eluting with a gradient formed from acetonitrile, water and formic acid. The product containing fractions were evaporated to yield 26.2 mg (61%) of the title compound. (MH+) 356.1.

EXAMPLE 15

{(R)-3-[(6-Chloro-benzooxazol-2-yl)-methyl-amino]-pyrrolidin-1-yl}-(2,6-dimethoxy-phenyl)-methanone

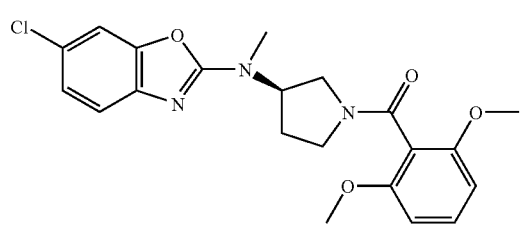

A mixture of 20 mg (0.05 mmol) [3-(6-Chloro-benzooxazol-2-ylamino)-pyrrolidin-1-yl]-(2,6-dimethoxy-phenyl)- methanone (example 1), 353 mg (2.48 mmol) methyliodid and 10 mg (0.075 mmol) K$_2$CO$_3$ in 0.5 mL DMF was stirred at 75° C. The mixture was concentrated, water and methanol was added and the mixture was subjected to purification by preparative HPLC on reversed phase eluting with a gradient formed from acetonitrile, water and formic acid. The product containing fractions were evaporated to yield 9.6 mg (461%) of the title compound as light yellow solid. (MH$^+$) 418.1.

EXAMPLE 16

{(R)-3-[(6-Chloro-benzothiazol-2-yl)-methyl-amino]-pyrrolidin-1-yl}-(2,6-dimethoxy-phenyl)-methanone

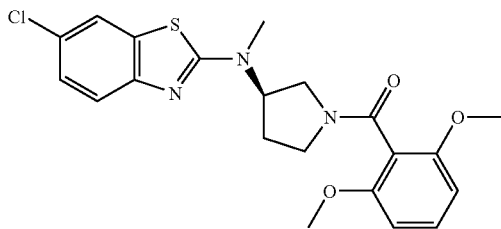

In analogy to the procedure described for the synthesis of {(R)-3-[(6-Chloro-benzooxazol-2-yl)-methyl-amino]-pyrrolidin-1-yl}-(2,6-dimethoxy-phenyl)-methanone (example 15) the title compound was prepared from [3-(6-Chloro-benzothiazol-2-ylamino)-pyrrolidin-1-yl]-(2,6-dimethoxy-phenyl)-methanone (example 7) and methyliodide. (MH$^+$) 432.1.

Intermediate 1

(7-Chloro-quinazolin-2-yl)-piperidin-3-yl-amine

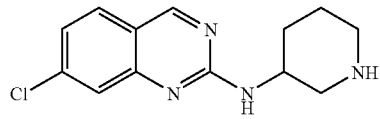

In analogy to the procedure described for the synthesis of (6-Chloro-benzooxazol-2-yl)-pyrrolidin-3-yl-amine; hydrochloride (example 1, step 1) the title compound was prepared from 2,7-dichloro-quinazoline (Synthesis 1978, 5, 379-82) and 3-Amino-piperidine-1-carboxylic acid tert-butyl ester (commercially available) and subsequent cleavage of the tert-butyl oxy carbonyl protecting group under acidic conditions. (MH$^+$) 263.1.

Intermediate 2

(7-Chloro-quinazolin-2-yl)-pyrrolidin-3-yl-amine

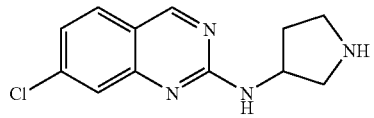

In analogy to the procedure described for the synthesis of (6-Chloro-benzooxazol-2-yl)-pyrrolidin-3-yl-amine; hydrochloride (example 1, step 1) the title compound was prepared from 2,7-dichloro-quinazoline (Synthesis 1978, 5, 379-82) and 3-Amino-pyrrolidine-1-carboxylic acid tert-butyl ester (commercially available) and subsequent cleavage of the tert-butyl oxy carbonyl protecting group under acidic conditions. (MH$^+$) 249.1.

Intermediate 3

7-Chloro-2-(pyrrolidin-3-ylamino)-3H-quinazolin-4-one

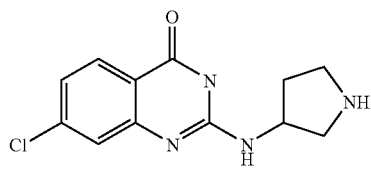

In analogy to the procedure described for the synthesis of (6-Chloro-benzooxazol-2-yl)-pyrrolidin-3-yl-amine; hydrochloride (example 1, step 1) the title compound was prepared from 2,7-Dichloro-4(3H)-quinazoline (Bioorganic & Medicinal Chemistry 2003, 11, 2439-2444) and 3-Amino-pyrrolidine-1-carboxylic acid tert-butyl ester (commercially available) and subsequent cleavage of the tert-butyl oxy carbonyl protecting group under acidic conditions. (MH$^+$) 265.1

Intermediate 4

(6-Chloro-benzooxazol-2-yl)-(R)-pyrrolidin-3-yl-amine, hydrochloride

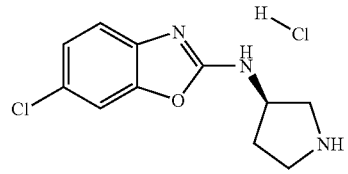

In analogy to the procedure described for the synthesis of (6-Chloro-benzooxazol-2-yl)-pyrrolidin-3-yl-amine; hydrochloride (example 1, step 1) the title compound was prepared from 2,6-dichloro-benzoxazole (commercially available) and R-3-amino-pyrrolidine-1-carboxylic acid tert-butyl ester (commercially available) and subsequent cleavage of the tert-butyl oxy carbonyl protecting group under acidic conditions. (MH$^+$) 238.0.

Intermediate 5

((R)-3-Amino-pyrrolidin-1-yl)-(2,6-dimethoxy-phenyl)-methanone

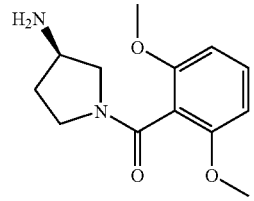

a) Step 1: [(R)-1-(2,6-Dimethoxy-benzoyl)-pyrrolidin-3-yl]-carbamic acid tert-butyl ester

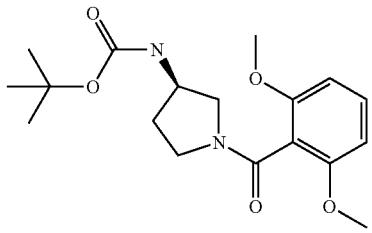

A mixture of 2.94 g (15.8 mmol) (R)-pyrrolidin-3-yl-carbamic acid tert-butyl ester (commercially available), 2,6-dimethoxybenzoyl chloride (commercially available) and 2.08 g (2.05 mmol) NEt$_3$ in 15 mL DCM was stirred at room temperature over night. The mixture was absorbed on isolute SPE and purified by column chromatography on silica eluting with a gradient formed from heptane and ethyl acetate to yield 3.78 g (68%) of the title compound as white foam. (MH$^+$) 351.2 b) Step 2

A mixture of 3.78 g (10.8 mmol) [(R)-1-(2,6-Dimethoxy-benzoyl)-pyrrolidin-3-yl]-carbamic acid tert-butyl ester and 13.5 mL 4N HCl in dioxane was stirred at room temperature for 1 h. The mixture was concentrated, NaHCO$_3$ aq. sat. was added and extracted with DCM. The combined organic layers were evaporated to yield 2.6 g of the title compound which was used without further purification. (MH$^+$) 251.1

Intermediate 6

2-Chloro-6,7-difluoro-benzooxazole

Commercially available

Intermediate 7

2-Chloro-4-fluoro-benzooxazole

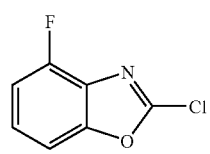

a) Step 1: 4-Fluoro-benzooxazole-2-thiol

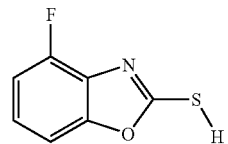

A mixture of 1 g (7.867 mmol) 2-amino-3-fluorophenol and 1.42 g (8.654 mmol) potassium ethylxanthogenate in 28 mL methanol was heated in a 70° C. oil bath for 3 h. The solvent was removed in vacuo. The residue was dissolved in 50 mL water. The aqueous layer was acidified with HCl 2N. The solid was filtered, washed with water and dried to provide 568 mg (42.7%) of the title compound as a light grey solid. MS(m/e): 168.0 (M−H$^+$).

b) Step 2: 2-Chloro-4-fluoro-benzooxazole

To a solution of 560 mg (3.31 mmol) 4-fluoro-benzooxazole-2-thiol in 3.6 mL (49.65 mmol) thionyl chloride was added dropwise 60.3 □L N,N-dimethylformamide dry at room temperature. The mixture was stirred at room temperature for 2.5 h. The solvent was removed in vacuo. The crude compound was purified with flash column chromatography on silica eluting with a gradient formed from n-heptane and ethyl acetate to provide 434 mg (76.4%) of the title compound as a white solid. MS(m/e): 171 (M+H$^+$).

Intermediate 8

Benzooxazol-2-yl-methyl-(R)-pyrrolidin-3-yl-amine

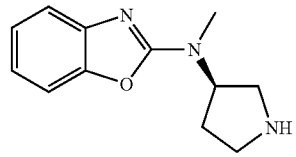

a) Step 1: ((R)-1-Benzyl-pyrrolidin-3-yl)-(6-chloro-benzooxazol-2-yl)-methyl-amine

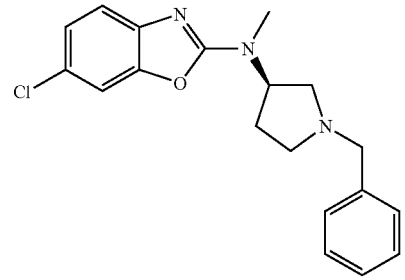

A mixture of 0.5 g (2.6 mmol) 2,6-dichloro benzoxazole, 0.68 g (3.58 mmol) ((R)-1-benzyl-pyrrolidin-3-yl)-methyl-amine and 0.4 g (4 mmol) NEt$_3$ in 12 mL DCM was stirred over night at room temperature. DCM was added and the mixture was washed with NaHCO$_3$ aq., dried with MgSO$_4$ and evaporated to dryness to yield the title compound as yellow oil which was used in the consecutive step without further purification. (MH$^+$) 342.1 b) Step 2

A solution of 0.99 g ((R)-1-Benzyl-pyrrolidin-3-yl)-(6-chloro-benzooxazol-2-yl)-methyl-amine in 5 mL ethanol and 0.4 mL acetic acid was hydrogenated over Pd/C 10% to yield after filtration and evaporation the title compound as yellow oil which was used in the consecutive step without further purification. (MH$^+$) 218.0

Intermediate 9

2,6,7-Trichloro-benzothiazole

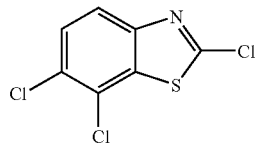

a) Step 1: 6,7-dichloro-benzothiazole-2-thiol

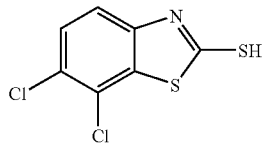

A mixture of 1.5 g (8.33 mmol) 3.4-dichloro-2-fluoroaniline and 1.64 g (10.00 mmol) potassium ethylxanthogenate in 8 mL dry N,N-dimethylformamide was heated in a 95° C. oil bath for 5 h. The reaction mixture was cooled to room temperature and diluted with water (25 mL). The mixture was acidified with aqueous HCl 2N. The precipitate was collected by filtration, washed with water and dried to provide 1.8 g (92%) of the title compound as a white solid. MS(m/e): 233.8 (M–H$^+$).

b) Step 2: 2,6,7-Trichloro-benzothiazole

To a suspension of 300 mg (1.270 mmol) 6,7-dichloro-benzothiazole-2-thiol in 1.4 mL (19.05 mmol) thionyl chloride was added dropwise 32.3 □L N,N-dimethylformamide dry at room temperature. The mixture was stirred at room temperature for 4 h. The solvent was removed in vacuo. The residue was purified with flash column chromatography on silica eluting with a gradient formed from n-heptane and ethyl acetate to provide 127 mg (41.9%) of the title compound as a yellow solid. MS(m/e): 239 (M+H$^+$).

Intermediate 10

((R)-3-Amino-pyrrolidin-1-yl)-(2-trifluoromethyl-phenyl)-methanone

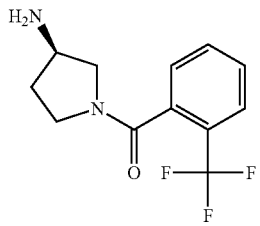

A mixture of 0.363 g (1.95 mmol) (R)-pyrrolidin-3-yl-carbamic acid tert-butyl ester (commercially available), 0.38 g (2 mmol) 2-trifluoromethyl-benzoic acid (commercially available), 0.69 g (2.15 mmol) TBTU and 0.378 g (2.92 mmol) DIPEA in 8 mL DMF was stirred at room temperature for 16 h. KHSO$_4$ aq. was added and the mixture was extracted with ethyl acetate. The combined organic layers were evaporated and the residue was treated with 4.87 mL 4N HCl in dioxane and stirred for 16 h at room temperature. The mixture was concentrated and methanol and water was added and the mixture was passed over a basic solid phase extraction cartridge eluting with methanol. The title compound was obtained after evaporation and used without further purification in the consecutive step. (MH$^+$) 259.1.

Intermediate 11

((R)-3-Amino-pyrrolidin-1-yl)-(2-trifluoromethoxy-phenyl)-methanone

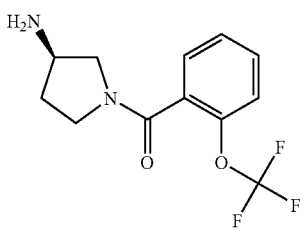

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-trifluoromethoxy-benzoic acid (commercially available) and subsequent cleavage of the tert-butyl oxy carbonyl protecting group under acidic conditions. (MH$^+$) 275.1.

Intermediate 12

((R)-3-Amino-pyrrolidin-1-yl)-[2-(1,1,2,2-tetrafluoro-ethoxy)-phenyl]-methanone

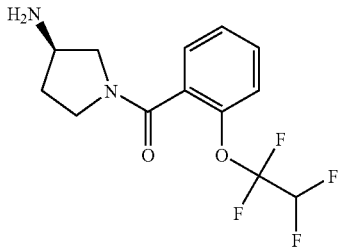

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-(1,1,2,2-Tetrafluoro-ethoxy)-benzoic acid (commercially available) and subsequent cleavage of the tert-butyl oxy carbonyl protecting group under acidic conditions. (MH$^+$) 307.1.

Intermediate 13

((R)-3-Amino-pyrrolidin-1-yl)-(5-methyl-2-trifluoromethyl-phenyl)-methanone

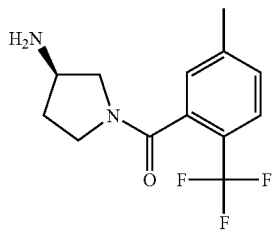

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 5-Methyl-2-trifluoromethyl-benzoic acid (commercially available) and subsequent cleavage of the tert-butyl oxy carbonyl protecting group under acidic conditions. (MH$^+$) 273.1.

Intermediate 14

((R)-3-Amino-pyrrolidin-1-yl)-(5-methyl-3-phenyl-isoxazol-4-yl)-methanone

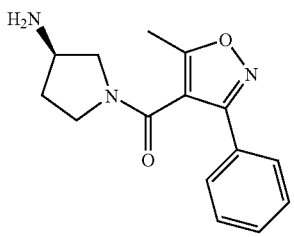

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 5-Methyl-3-phenyl-isoxazole-4-carboxylic acid (commercially available) and subsequent cleavage of the tert-butyl oxy carbonyl protecting group under acidic conditions. (MH$^+$) 272.1.

Intermediate 15

((R)-3-Amino-pyrrolidin-1-yl)-[2-(3-methyl-[1,2,4]oxadiazol-5-yl)-phenyl]-methanone

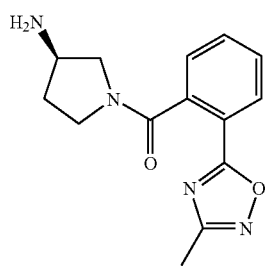

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-(3-Methyl-[1,2,4]oxadiazol-5-yl)-benzoic acid (commercially available) and subsequent cleavage of the tert-butyl oxy carbonyl protecting group under acidic conditions. (MH$^+$) 273.1.

Intermediate 16

((R)-3-Amino-pyrrolidin-1-yl)-(2-chloro-5-methyl-phenyl)-methanone

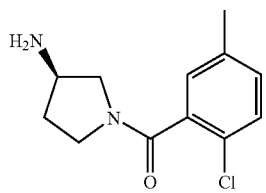

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-Chloro-5-methyl-benzoic acid (commercially available) and subsequent cleavage of the tert-butyl oxy carbonyl protecting group under acidic conditions. (MH$^+$) 239.0

Intermediate 17

((R)-3-Amino-pyrrolidin-1-yl)-(2-methoxy-5-methyl-phenyl)-methanone

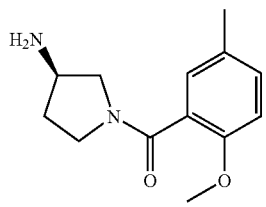

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-Methoxy-5-methyl-benzoic acid (commercially available) and subsequent cleavage of the tert-butyl oxy carbonyl protecting group under acidic conditions.

Intermediate 18

((R)-3-Amino-pyrrolidin-1-yl)-(2-methyl-5-phenyl-thiazol-4-yl)-methanone

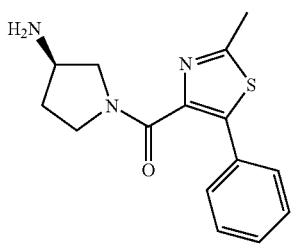

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 2-Methyl-5-phenyl-thiazole-4-carboxylic acid (commercially available) and subsequent cleavage of the tert-butyl oxy carbonyl protecting group under acidic conditions. (MH$^+$) 288.1.

Intermediate 19

((R)-3-Amino-pyrrolidin-1-yl)-(5-phenyl-isoxazol-4-yl)-methanone

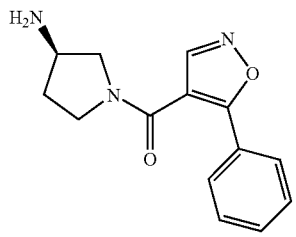

In analogy to the procedure described for the synthesis of ((R)-3-Amino-pyrrolidin-1-yl)-(2-trifluoromethyl-phenyl)-methanone (intermediate 10) the title compound was prepared from (R)-pyrrolidin-3-yl-carbamic acid tert-butyl ester (commercially available), 5-phenyl-4-isoxazolecarboxylic acid (commercially available) and subsequent cleavage of the tert-butyl oxy carbonyl protecting group under acidic conditions. (MH$^+$) 258.3.

In analogy to the procedures described for examples 1, 13 and 14 further compounds have been synthesized from the starting materials listed in table 1. Table 1 comprises examples 17-199.

| No. | structure | MW | name | starting materials | MW found (MH+) |
|---|---|---|---|---|---|
| 17 | 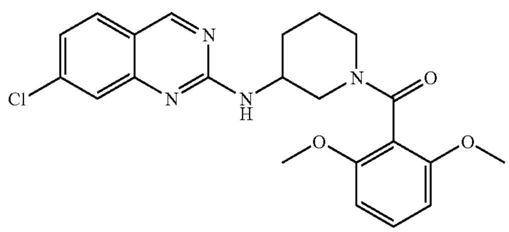 | 426.9 | [3-(7-Chloro-quinazolin-2-ylamino)-piperidin-1-yl]-(2,6-dimethoxy-phenyl)-methanone | (7-Chloro-quinazolin-2-yl)-piperidin-3-yl-amine (intermediate 1) and 2,6-Dimethoxy-benzoyl chloride (commercially available) | 427.3 |
| 18 | 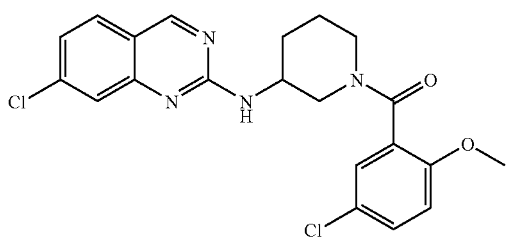 | 431.3 | (5-Chloro-2-methoxy-phenyl)-[3-(7-chloro-quinazolin-2-ylamino)-piperidin-1-yl]-methanone | (7-Chloro-quinazolin-2-yl)-piperidin-3-yl-amine (intermediate 1) and 5-Chloro-2-methoxy-benzoyl chloride (commercially available) | 431.1 |
| 19 | 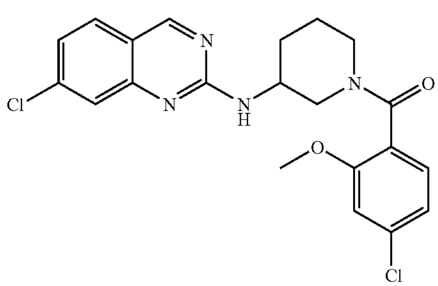 | 431.3 | (4-Chloro-2-methoxy-phenyl)-[3-(7-chloro-quinazolin-2-ylamino)-piperidin-1-yl]-methanone | (7-Chloro-quinazolin-2-yl)-piperidin-3-yl-amine (intermediate 1) and 4-Chloro-2-methoxy-benzoic acid (commercially available) | 431.1 |
| 20 | 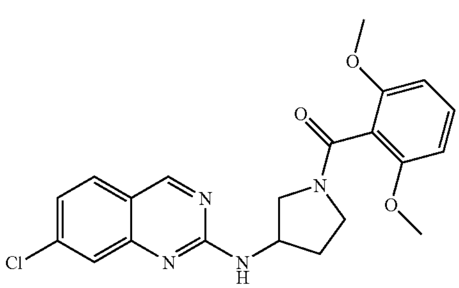 | 412.9 | [3-(7-Chloro-quinazolin-2-ylamino)-pyrrolidin-1-yl]-(2,6-dimethoxy-phenyl)-methanone | (7-Chloro-quinazolin-2-yl)-pyrrolidin-3-yl-amine (intermediate 2) and 2,6-Dimethoxy-benzoyl chloride (commercially available) | 413.3 |

| No. | structure | MW | name | starting materials | MW found (MH+) |
|---|---|---|---|---|---|
| 21 | 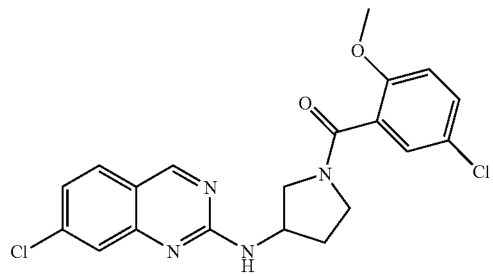 | 417.3 | (5-Chloro-2-methoxy-phenyl)-[3-(7-chloro-quinazolin-2-ylamino)-pyrrolidin-1-yl]-methanone | (7-Chloro-quinazolin-2-yl)-pyrrolidin-3-yl-amine (intermediate 2) and 5-Chloro-2-methoxy-benzoyl chloride (commercially available) | 417.4 |
| 22 | 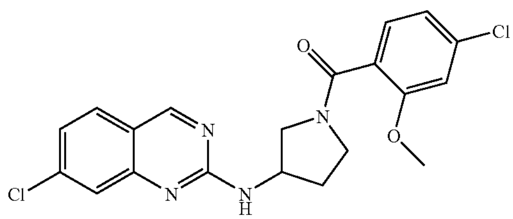 | 417.3 | (4-Chloro-2-methoxy-phenyl)-[3-(7-chloro-quinazolin-2-ylamino)-pyrrolidin-1-yl]-methanone | (7-Chloro-quinazolin-2-yl)-pyrrolidin-3-yl-amine (intermediate 2) and 4-Chloro-2-methoxy-benzoic acid (commercially available) | 417.4 |
| 23 | 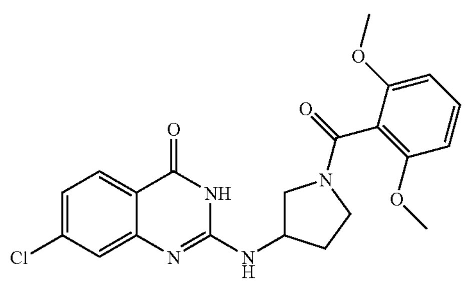 | 428.9 | 7-Chloro-2-[1-(2,6-dimethoxy-benzoyl)-pyrrolidin-3-ylamino]-3H-quinazolin-4-one | 7-Chloro-2-(pyrrolidin-3-ylamino)-3H-quinazolin-4-one (intermediate 3) and 2,6-Dimethoxy-benzoyl chloride (commercially available) | 429.4 |
| 24 | 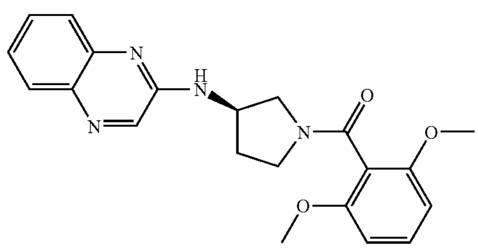 | 378.4 | (2,6-Dimethoxy-phenyl)-[(R)-3-(quinoxalin-2-ylamino)-pyrrolidin-1-yl]-methanone | 2-chloro-quinoxaline (commercially available), 3-(R)-amino-pyrrolidine-1-carboxylic acid tert-butyl ester (commercially available) (coupling at elevated temperature) and 2,6-dimethoxybenzoyl chloride (commercially available) | 379.2 |
| 25 | 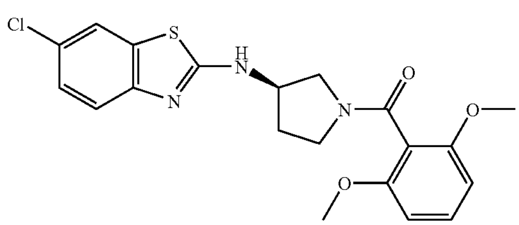 | 417.9 | [(R)-3-(6-Chloro-benzothiazol-2-ylamino)-pyrrolidin-1-yl]-(2,6-dimethoxy-phenyl)-methanone | 2,6-dichloro-benzothiazole (commercially available), 3-(R)-amino-pyrrolidine-1-carboxylic acid tert-butyl ester (commercially available) and 2,6-dimethoxybenzoyl chloride (commercially available). | 418.1 |
| 26 | 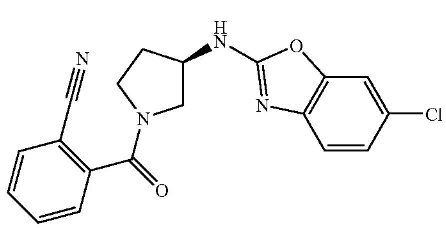 | 366.8 | 2-[(R)-3-(6-Chloro-benzooxazol-2-ylamino)-pyrrolidine-1-carbonyl]-benzonitrile | (6-Chloro-benzooxazol-2-yl)-(R)-pyrrolidin-3-yl-amine, hydrochloride and 2-Cyano-benzoic acid (commercially available) | 367.1 |

| No. | structure | MW | name | starting materials | MW found (MH+) |
|---|---|---|---|---|---|
| 27 | 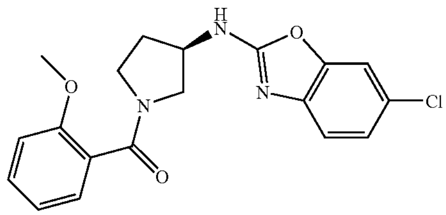 | 371.8 | [(R)-3-(6-Chloro-benzooxazol-2-ylamino)-pyrrolidin-1-yl]-(2-methoxy-phenyl)-methanone | (6-Chloro-benzooxazol-2-yl)-(R)-pyrrolidin-3-yl-amine, hydrochloride (intermediate 4) and 2-Methoxy-benzoic acid (commercially available) | 372.1 |
| 28 | 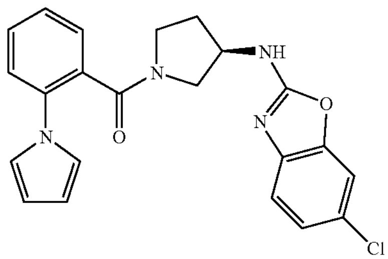 | 406.9 | [(R)-3-(6-Chloro-benzooxazol-2-ylamino)-pyrrolidin-1-yl]-(2-pyrrol-1-yl-phenyl)-methanone | (6-Chloro-benzooxazol-2-yl)-(R)-pyrrolidin-3-yl-amine, hydrochloride (intermediate 4) and 2-Pyrrol-1-yl-benzoic acid (commercially available) | 407.1 |
| 29 | 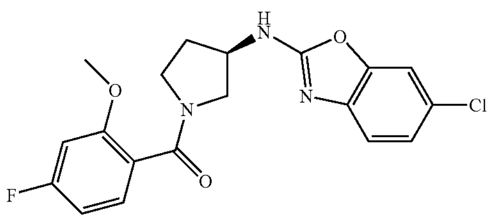 | 389.8 | [(R)-3-(6-Chloro-benzooxazol-2-ylamino)-pyrrolidin-1-yl]-(4-fluoro-2-methoxy-phenyl)-methanone | (6-Chloro-benzooxazol-2-yl)-(R)-pyrrolidin-3-yl-amine, hydrochloride (intermediate 4) and 4-Fluoro-2-methoxy-benzoic acid (commercially available) | 390.1 |
| 30 | 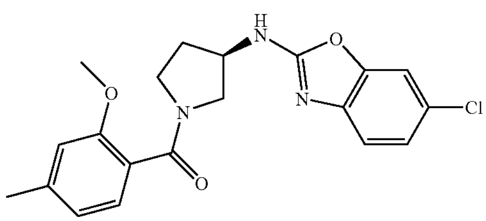 | 385.8 | [(R)-3-(6-Chloro-benzooxazol-2-ylamino)-pyrrolidin-1-yl]-(2-methoxy-4-methyl-phenyl)-methanone | (6-Chloro-benzooxazol-2-yl)-(R)-pyrrolidin-3-yl-amine, hydrochloride (intermediate 4) and 2-Methoxy-4-methyl-benzoic acid (commercially available) | 386.1 |
| 31 | 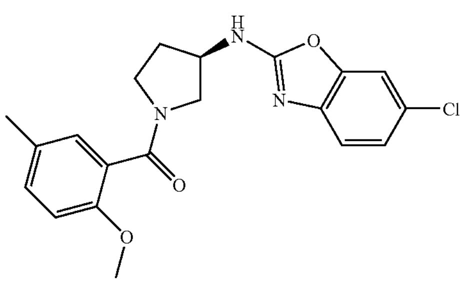 | 385.8 | [(R)-3-(6-Chloro-benzooxazol-2-ylamino)-pyrrolidin-1-yl]-(2-methoxy-5-methyl-phenyl)-methanone | (6-Chloro-benzooxazol-2-yl)-(R)-pyrrolidin-3-yl-amine, hydrochloride (intermediate 4) and 2-Methoxy-5-methyl-benzoic acid (commercially available) | 386.1 |
| 32 | 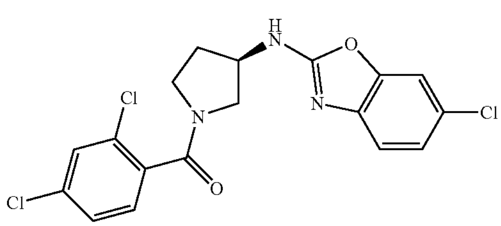 | 410.7 | [(R)-3-(6-Chloro-benzooxazol-2-ylamino)-pyrrolidin-1-yl]-(2,4-dichloro-phenyl)-methanone | (6-Chloro-benzooxazol-2-yl)-(R)-pyrrolidin-3-yl-amine, hydrochloride (intermediate 4) and 2,4-Dichloro-benzoic acid (commercially available) | 410 |

| No. | structure | MW | name | starting materials | MW found (MH+) |
|---|---|---|---|---|---|
| 33 | 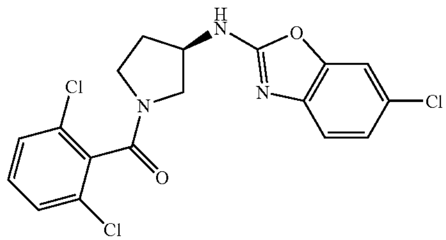 | 410.7 | [(R)-3-(6-Chloro-benzooxazol-2-ylamino)-pyrrolidin-1-yl]-(2,6-dichloro-phenyl)-methanone | (6-Chloro-benzooxazol-2-yl)-(R)-pyrrolidin-3-yl-amine, hydrochloride (intermediate 4) and 2,6-Dichloro-benzoic acid (commercially available) | 410 |
| 34 | 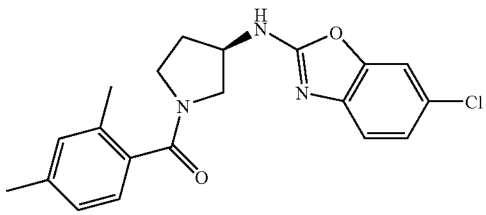 | 369.9 | [(R)-3-(6-Chloro-benzooxazol-2-ylamino)-pyrrolidin-1-yl]-(2,4-dimethyl-phenyl)-methanone | (6-Chloro-benzooxazol-2-yl)-(R)-pyrrolidin-3-yl-amine, hydrochloride (intermediate 4) and 2,4-Dimethyl-benzoic acid (commercially available) | 370.1 |
| 35 | 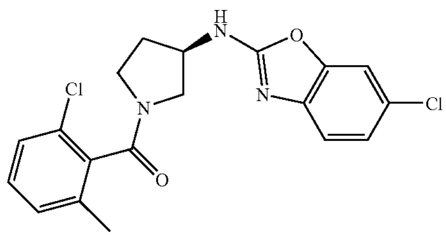 | 390.3 | [(R)-3-(6-Chloro-benzooxazol-2-ylamino)-pyrrolidin-1-yl]-(2-chloro-6-methyl-phenyl)-methanone | (6-Chloro-benzooxazol-2-yl)-(R)-pyrrolidin-3-yl-amine, hydrochloride (intermediate 4) and 2-Chloro-6-methyl-benzoic acid (commercially available) | 390.1 |
| 36 | 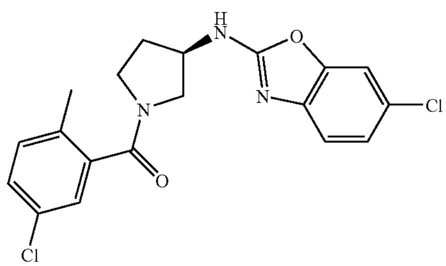 | 390.3 | [(R)-3-(6-Chloro-benzooxazol-2-ylamino)-pyrrolidin-1-yl]-(5-chloro-2-methyl-phenyl)-methanone | (6-Chloro-benzooxazol-2-yl)-(R)-pyrrolidin-3-yl-amine, hydrochloride (intermediate 4) and 5-Chloro-2-methyl-benzoic acid (commercially available) | 390.1 |
| 37 | 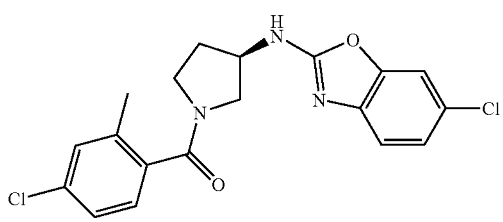 | 390.3 | [(R)-3-(6-Chloro-benzooxazol-2-ylamino)-pyrrolidin-1-yl]-(4-chloro-2-methyl-phenyl)-methanone | (6-Chloro-benzooxazol-2-yl)-(R)-pyrrolidin-3-yl-amine, hydrochloride (intermediate 4) and 4-Chloro-2-methyl-benzoic acid (commercially available) | 390.1 |
| 38 | 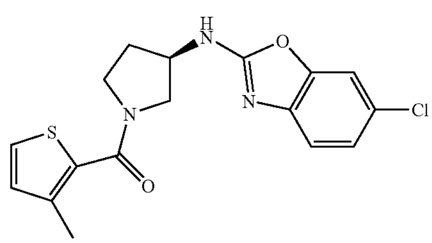 | 361.9 | [(R)-3-(6-Chloro-benzooxazol-2-ylamino)-pyrrolidin-1-yl]-(3-methyl-thiophen-2-yl)-methanone | (6-Chloro-benzooxazol-2-yl)-(R)-pyrrolidin-3-yl-amine, hydrochloride (intermediate 4) and 3-Methyl-thiophene-2-carboxylic acid (commercially available) | 362.1 |

| No. | structure | MW | name | starting materials | MW found (MH+) |
|---|---|---|---|---|---|
| 39 | 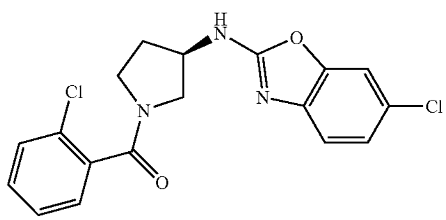 | 376.2 | [(R)-3-(6-Chloro-benzooxazol-2-ylamino)-pyrrolidin-1-yl]-(2-chloro-phenyl)-methanone | (6-Chloro-benzooxazol-2-yl)-(R)-pyrrolidin-3-yl-amine, hydrochloride (intermediate 4) and 2-Chloro-benzoic acid (commercially available) | 376 |
| 40 | 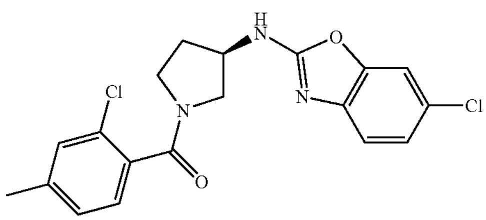 | 390.3 | [(R)-3-(6-Chloro-benzooxazol-2-ylamino)-pyrrolidin-1-yl]-(2-chloro-4-methyl-phenyl)-methanone | (6-Chloro-benzooxazol-2-yl)-(R)-pyrrolidin-3-yl-amine, hydrochloride (intermediate 4) and 2-Chloro-4-methyl-benzoic acid (commercially available) | 390.1 |
| 41 | 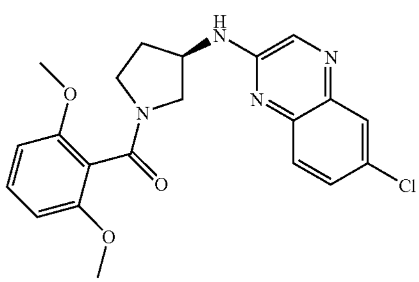 | 412.9 | [(R)-3-(6-Chloro-quinoxalin-2-ylamino)-pyrrolidin-1-yl]-(2,6-dimethoxy-phenyl)-methanone | ((R)-3-Amino-pyrrolidin-1-yl)-(2,6-dimethoxy-phenyl)-methanone (intermediate 5) and 2,6-Dichloro-quinoxaline (commercially available) | 413.1 |
| 42 | 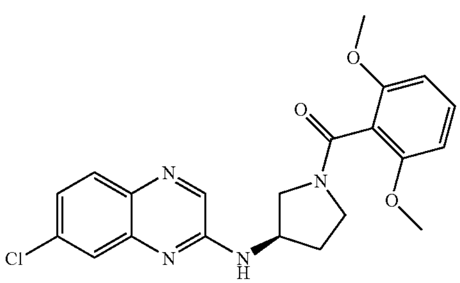 | 412.9 | [(R)-3-(7-Chloro-quinoxalin-2-ylamino)-pyrrolidin-1-yl]-(2,6-dimethoxy-phenyl)-methanone | ((R)-3-Amino-pyrrolidin-1-yl)-(2,6-dimethoxy-phenyl)-methanone (intermediate 5) and 2,7-Dichloro-quinoxaline (commercially available) | 413.1 |
| 43 | 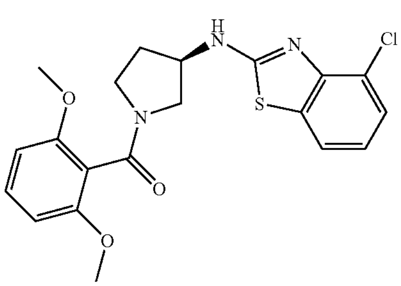 | 417.9 | [(R)-3-(4-Chloro-benzothiazol-2-ylamino)-pyrrolidin-1-yl]-(2,6-dimethoxy-phenyl)-methanone | ((R)-3-Amino-pyrrolidin-1-yl)-(2,6-dimethoxy-phenyl)-methanone (intermediate 5) and 2,4-dichloro-benzothiazole (commercially available) | 418.1 |

-continued

| No. | structure | MW | name | starting materials | MW found (MH+) |
|---|---|---|---|---|---|
| 44 | 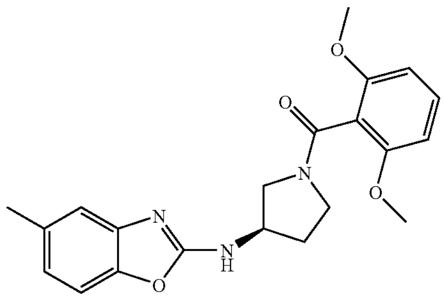 | 381.4 | (2,6-Dimethoxy-phenyl)-[(R)-3-(5-methyl-benzooxazol-2-ylamino)-pyrrolidin-1-yl]-methanone | ((R)-3-Amino-pyrrolidin-1-yl)-(2,6-dimethoxy-phenyl)-methanone (intermediate 5) and 2-chloro-5-methyl-1,3-benzoxazole (commercially available) | 382.2 |
| 45 | 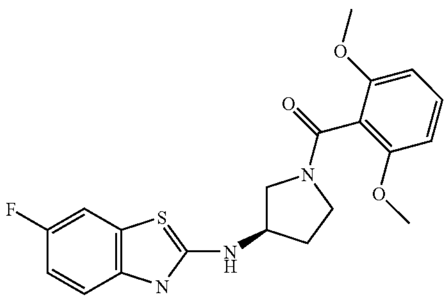 | 401.5 | (2,6-Dimethoxy-phenyl)-[(R)-3-(6-fluoro-benzothiazol-2-ylamino)-pyrrolidin-1-yl]-methanone | ((R)-3-Amino-pyrrolidin-1-yl)-(2,6-dimethoxy-phenyl)-methanone (intermediate 5) and 2-Chloro-5-fluorobenzothiazole (commercially available) | 402.1 |
| 46 | 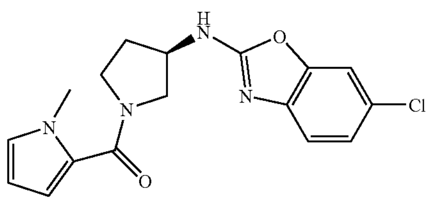 | 344.8 | [(R)-3-(6-Chloro-benzooxazol-2-ylamino)-pyrrolidin-1-yl]-(1-methyl-1H-pyrrol-2-yl)-methanone | (6-Chloro-benzooxazol-2-yl)-(R)-pyrrolidin-3-yl-amine, hydrochloride (intermediate 4) and 1-Methyl-1H-pyrrole-2-carboxylic acid (commercially available) | 345.1 |
| 47 | 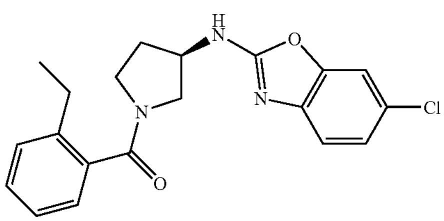 | 369.9 | [(R)-3-(6-Chloro-benzooxazol-2-ylamino)-pyrrolidin-1-yl]-(2-ethyl-phenyl)-methanone | (6-Chloro-benzooxazol-2-yl)-(R)-pyrrolidin-3-yl-amine, hydrochloride (intermediate 4) and 2-Ethyl-benzoic acid (commercially available) | 370.1 |
| 48 | 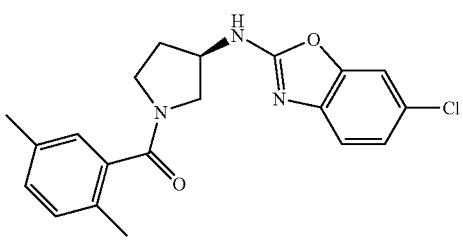 | 369.9 | [(R)-3-(6-Chloro-benzooxazol-2-ylamino)-pyrrolidin-1-yl]-(2,5-dimethyl-phenyl)-methanone | (6-Chloro-benzooxazol-2-yl)-(R)-pyrrolidin-3-yl-amine, hydrochloride (intermediate 4) and 2,5-Dimethyl-benzoic acid (commercially available) | 370.1 |
| 49 | 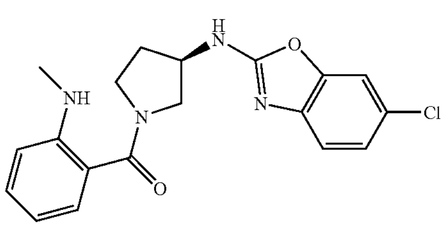 | 370.8 | [(R)-3-(6-Chloro-benzooxazol-2-ylamino)-pyrrolidin-1-yl]-(2-methylamino-phenyl)-methanone | (6-Chloro-benzooxazol-2-yl)-(R)-pyrrolidin-3-yl-amine, hydrochloride (intermediate 4) and 2-Methylamino-benzoic acid (commercially available) | 371.1 |

-continued

| No. | structure | MW | name | starting materials | MW found (MH+) |
|---|---|---|---|---|---|
| 50 | 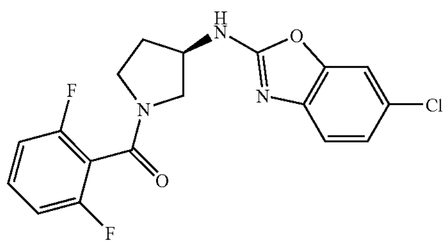 | 377.8 | [(R)-3-(6-Chloro-benzooxazol-2-ylamino)-pyrrolidin-1-yl]-(2,6-difluoro-phenyl)-methanone | (6-Chloro-benzooxazol-2-yl)-(R)-pyrrolidin-3-yl-amine, hydrochloride (intermediate 4) and 2,6-Difluoro-benzoic acid (commercially available) | 378.1 |
| 51 | 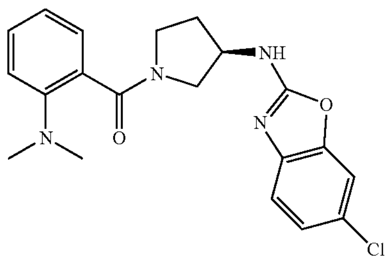 | 384.9 | [(R)-3-(6-Chloro-benzooxazol-2-ylamino)-pyrrolidin-1-yl]-(2-dimethylamino-phenyl)-methanone | (6-Chloro-benzooxazol-2-yl)-(R)-pyrrolidin-3-yl-amine, hydrochloride (intermediate 4) and 2-Dimethylamino-benzoic acid (commercially available) | 385.1 |
| 52 | 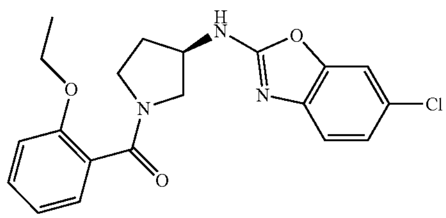 | 385.8 | [(R)-3-(6-Chloro-benzooxazol-2-ylamino)-pyrrolidin-1-yl]-(2-ethoxy-phenyl)-methanone | (6-Chloro-benzooxazol-2-yl)-(R)-pyrrolidin-3-yl-amine, hydrochloride (intermediate 4) and 2-Ethoxy-benzoic acid (commercially available) | 386.1 |
| 53 | 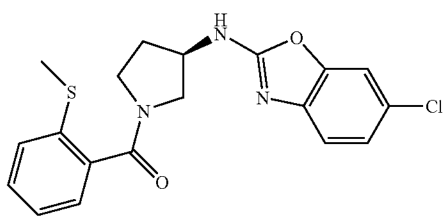 | 387.9 | [(R)-3-(6-Chloro-benzooxazol-2-ylamino)-pyrrolidin-1-yl]-(2-methylsulfanyl-phenyl)-methanone | (6-Chloro-benzooxazol-2-yl)-(R)-pyrrolidin-3-yl-amine, hydrochloride (intermediate 4) and 2-Methylsulfanyl-benzoic acid (commercially available) | 388.1 |
| 54 | 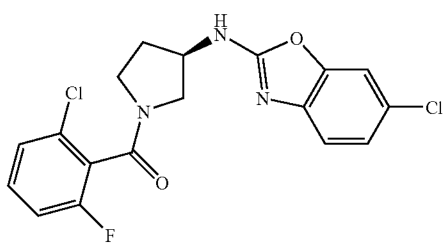 | 394.2 | [(R)-3-(6-Chloro-benzooxazol-2-ylamino)-pyrrolidin-1-yl]-(2-chloro-6-fluoro-phenyl)-methanone | (6-Chloro-benzooxazol-2-yl)-(R)-pyrrolidin-3-yl-amine, hydrochloride (intermediate 4) and 2-Chloro-6-fluoro-benzoic acid (commercially available) | 394 |
| 55 | 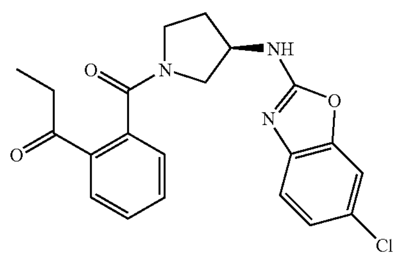 | 397.9 | 1-{2-[(R)-3-(6-Chloro-benzooxazol-2-ylamino)-pyrrolidine-1-carbonyl]-phenyl}-propan-1-one | (6-Chloro-benzooxazol-2-yl)-(R)-pyrrolidin-3-yl-amine, hydrochloride (intermediate 4) and 2-Propionyl-benzoic acid (commercially available) | 398.1 |

-continued

| No. | structure | MW | name | starting materials | MW found (MH+) |
|---|---|---|---|---|---|
| 56 | 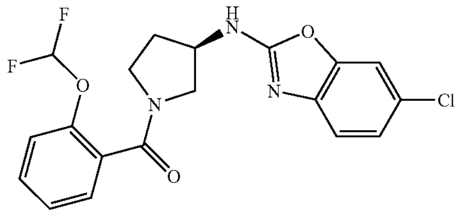 | 407.8 | [(R)-3-(6-Chloro-benzooxazol-2-ylamino)-pyrrolidin-1-yl]-(2-difluoromethoxy-phenyl)-methanone | (6-Chloro-benzooxazol-2-yl)-(R)-pyrrolidin-3-yl-amine, hydrochloride (intermediate 4) and 2-Difluoromethoxy-benzoic acid (commercially available) | 408.1 |
| 57 | 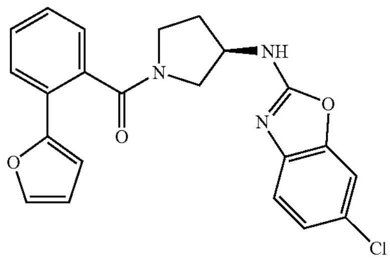 | 407.9 | [(R)-3-(6-Chloro-benzooxazol-2-ylamino)-pyrrolidin-1-yl]-(2-furan-2-yl-phenyl)-methanone | (6-Chloro-benzooxazol-2-yl)-(R)-pyrrolidin-3-yl-amine, hydrochloride (intermediate 4) and 2-Furan-2-yl-benzoic acid (commercially available) | 408.1 |
| 58 | 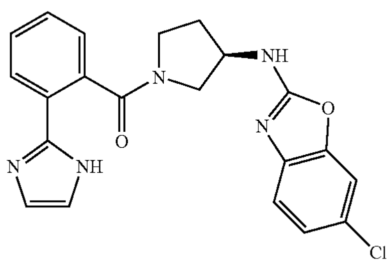 | 407.9 | [(R)-3-(6-Chloro-benzooxazol-2-ylamino)-pyrrolidin-1-yl]-[2-(1H-imidazol-2-yl)-phenyl]-methanone | (6-Chloro-benzooxazol-2-yl)-(R)-pyrrolidin-3-yl-amine, hydrochloride (intermediate 4) and 2-(1H-Imidazol-2-yl)-benzoic acid (commercially available) | 408.1 |
| 59 | 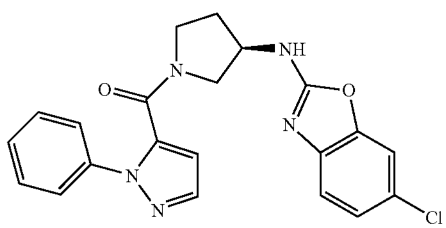 | 407.9 | [(R)-3-(6-Chloro-benzooxazol-2-ylamino)-pyrrolidin-1-yl]-(2-phenyl-2H-pyrazol-3-yl)-methanone | (6-Chloro-benzooxazol-2-yl)-(R)-pyrrolidin-3-yl-amine, hydrochloride (intermediate 4) and 2-Phenyl-2H-pyrazole-3-carboxylic acid (commercially available) | 408.1 |
| 60 | 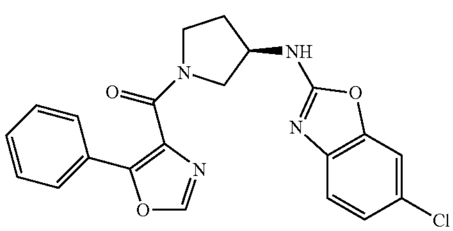 | 408.8 | [(R)-3-(6-Chloro-benzooxazol-2-ylamino)-pyrrolidin-1-yl]-(5-phenyl-oxazol-4-yl)-methanone | (6-Chloro-benzooxazol-2-yl)-(R)-pyrrolidin-3-yl-amine, hydrochloride (intermediate 4) and 5-Phenyl-oxazole-4-carboxylic acid (commercially available) | 409.1 |
| 61 | 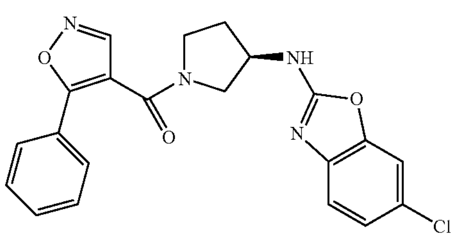 | 408.8 | [(R)-3-(6-Chloro-benzooxazol-2-ylamino)-pyrrolidin-1-yl]-(5-phenyl-isoxazol-4-yl)-methanone | (6-Chloro-benzooxazol-2-yl)-(R)-pyrrolidin-3-yl-amine, hydrochloride (intermediate 4) and 5-Phenyl-isoxazole-4-carboxylic acid (commercially available) | 409.1 |

-continued

| No. | structure | MW | name | starting materials | MW found (MH+) |
|---|---|---|---|---|---|
| 62 | 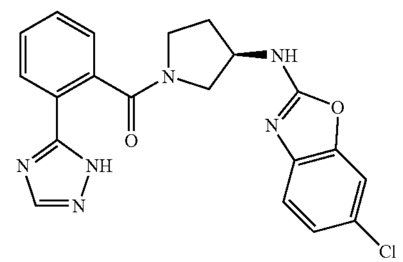 | 408.8 | [(R)-3-(6-Chloro-benzooxazol-2-ylamino)-pyrrolidin-1-yl]-[2-(2H-[1,2,4]triazol-3-yl)-phenyl]-methanone | (6-Chloro-benzooxazol-2-yl)-(R)-pyrrolidin-3-yl-amine, hydrochloride (intermediate 4) and 2-(2H-[1,2,4]Triazol-3-yl)-benzoic acid (commercially available) | 409.1 |
| 63 | 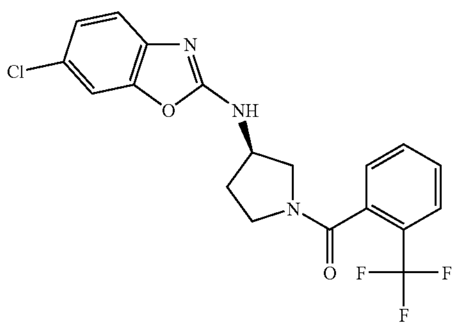 | 409.8 | [(R)-3-(6-Chloro-benzooxazol-2-ylamino)-pyrrolidin-1-yl]-(2-trifluoromethyl-phenyl)-methanone | (6-Chloro-benzooxazol-2-yl)-(R)-pyrrolidin-3-yl-amine, hydrochloride (intermediate 4) and 2-Trifluoromethyl-benzoic acid (commercially available) | 410.1 |
| 64 | 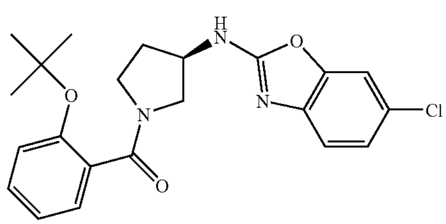 | 413.9 | (2-tert-Butoxy-phenyl)-[(R)-3-(6-chloro-benzooxazol-2-ylamino)-pyrrolidin-1-yl]-methanone | (6-Chloro-benzooxazol-2-yl)-(R)-pyrrolidin-3-yl-amine, hydrochloride (intermediate 4) and 2-tert-Butoxy-benzoic acid (commercially available) | 414.1 |
| 65 | 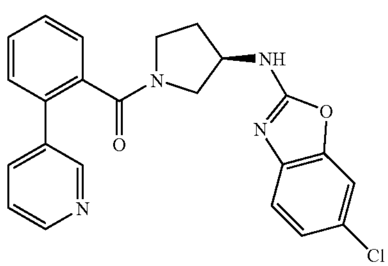 | 418.9 | [(R)-3-(6-Chloro-benzooxazol-2-ylamino)-pyrrolidin-1-yl]-(2-pyridin-3-yl-phenyl)-methanone | (6-Chloro-benzooxazol-2-yl)-(R)-pyrrolidin-3-yl-amine, hydrochloride (intermediate 4) and 2-Pyridin-3-yl-benzoic acid (commercially available) | 419.1 |
| 66 | 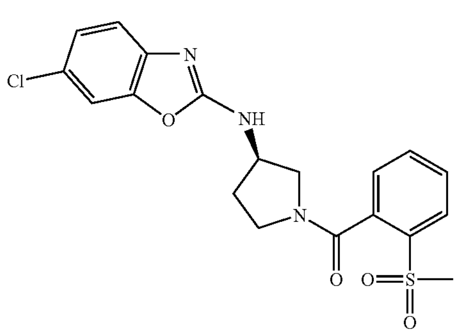 | 419.9 | [(R)-3-(6-Chloro-benzooxazol-2-ylamino)-pyrrolidin-1-yl]-(2-methanesulfonyl-phenyl)-methanone | (6-Chloro-benzooxazol-2-yl)-(R)-pyrrolidin-3-yl-amine, hydrochloride (intermediate 4) and 2-Methanesulfonyl-benzoic acid (commerically available) | 420.1 |

-continued

| No. | structure | MW | name | starting materials | MW found (MH+) |
|---|---|---|---|---|---|
| 67 | 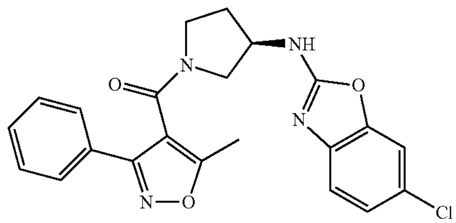 | 422.9 | [(R)-3-(6-Chloro-benzooxazol-2-ylamino)-pyrrolidin-1-yl]-(5-methyl-3-phenyl-isoxazol-4-yl)-methanone | (6-Chloro-benzooxazol-2-yl)-(R)-pyrrolidin-3-yl-amine, hydrochloride (intermediate 4) and 5-Methyl-3-phenyl-isoxazole-4-carboxylic acid (commercially available) | 423.1 |
| 68 | 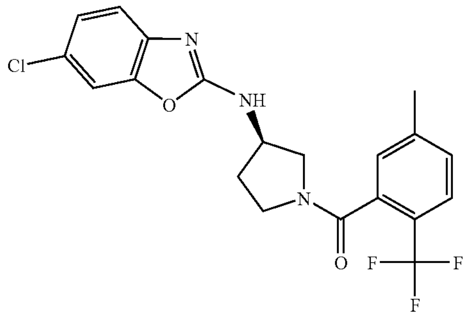 | 423.8 | [(R)-3-(6-Chloro-benzooxazol-2-ylamino)-pyrrolidin-1-yl]-(5-methyl-2-trifluoromethyl-phenyl)-methanone | (6-Chloro-benzooxazol-2-yl)-(R)-pyrrolidin-3-yl-amine, hydrochloride (intermediate 4) and 5-Methyl-2-trifluoromethyl-benzoic acid (commercially available) | 424.1 |
| 69 | 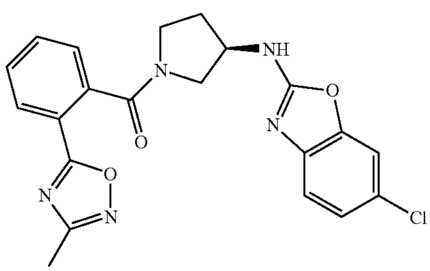 | 423.9 | [(R)-3-(6-Chloro-benzooxazol-2-ylamino)-pyrrolidin-1-yl]-[2-(3-methyl-[1,2,4]oxadiazol-5-yl)-phenyl]-methanone | (6-Chloro-benzooxazol-2-yl)-(R)-pyrrolidin-3-yl-amine, hydrochloride (intermediate 4) and 2-(3-Methyl-[1,2,4]oxadiazol-5-yl)-benzoic acid (commercially available) | 424.1 |
| 70 | 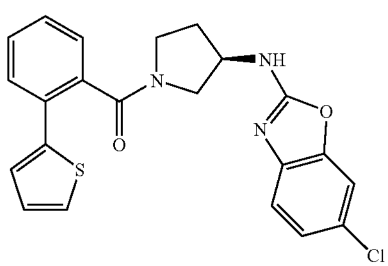 | 423.9 | [(R)-3-(6-Chloro-benzooxazol-2-ylamino)-pyrrolidin-1-yl]-(2-thiophen-2-yl-phenyl)-methanone | (6-Chloro-benzooxazol-2-yl)-(R)-pyrrolidin-3-yl-amine, hydrochloride (intermediate 4) and 2-Thiophen-2-yl-benzoic acid (commercially available) | 424.1 |
| 71 | 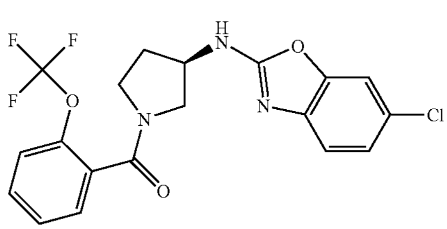 | 425.8 | [(R)-3-(6-Chloro-benzooxazol-2-ylamino)-pyrrolidin-1-yl]-(2-trifluoromethoxy-phenyl)-methanone | (6-Chloro-benzooxazol-2-yl)-(R)-pyrrolidin-3-yl-amine, hydrochloride (intermediate 4) and 2-Trifluoromethoxy-benzoic acid (commercially available) | 426.1 |

-continued

| No. | structure | MW | name | starting materials | MW found (MH+) |
|---|---|---|---|---|---|
| 72 | 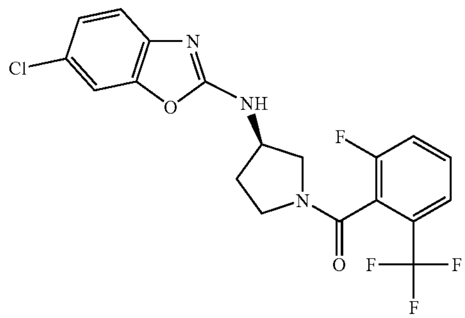 | 427.8 | [(R)-3-(6-Chloro-benzooxazol-2-ylamino)-pyrrolidin-1-yl]-(2-fluoro-6-trifluoromethyl-phenyl)-methanone | (6-Chloro-benzooxazol-2-yl)-(R)-pyrrolidin-3-yl-amine, hydrochloride (intermediate 4) and 2-Fluoro-6-trifluoromethyl-benzoic acid (commercially available) | 428.1 |
| 73 | 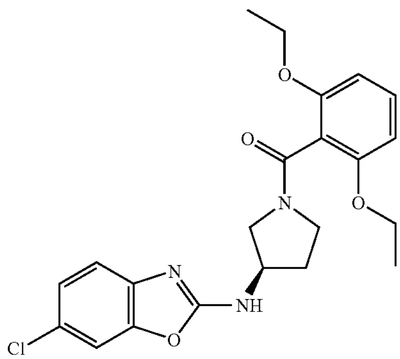 | 429.9 | [(R)-3-(6-Chloro-benzooxazol-2-ylamino)-pyrrolidin-1-yl]-(2,6-diethoxy-phenyl)-methanone | (6-Chloro-benzooxazol-2-yl)-(R)-pyrrolidin-3-yl-amine, hydrochloride (intermediate 4) and 2,6-Diethoxy-benzoic acid (commercially available) | 430.1 |
| 74 | 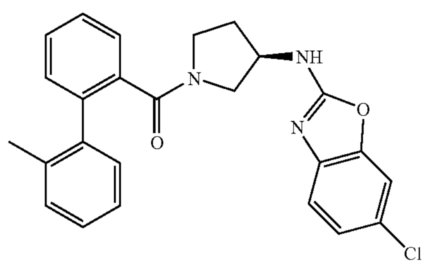 | 431.9 | [(R)-3-(6-Chloro-benzooxazol-2-ylamino)-pyrrolidin-1-yl]-(2'-methyl-biphenyl-2-yl)-methanone | (6-Chloro-benzooxazol-2-yl)-(R)-pyrrolidin-3-yl-amine, hydrochloride (intermediate 4) and 2'-Methyl-biphenyl-2-carboxylic acid (commercially available) | 432.1 |
| 75 | 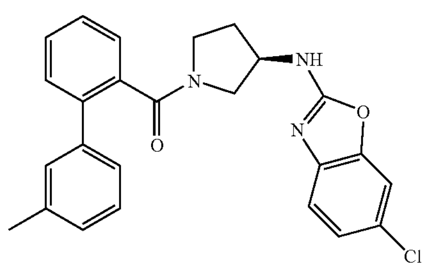 | 431.9 | [(R)-3-(6-Chloro-benzooxazol-2-ylamino)-pyrrolidin-1-yl]-(3'-methyl-biphenyl-2-yl)-methanone | (6-Chloro-benzooxazol-2-yl)-(R)-pyrrolidin-3-yl-amine, hydrochloride (intermediate 4) and 3'-Methyl-biphenyl-2-carboxylic acid (commercially available) | 432.1 |
| 76 | 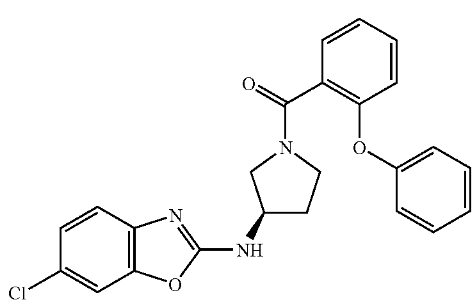 | 433.9 | [(R)-3-(6-Chloro-benzooxazol-2-ylamino)-pyrrolidin-1-yl]-(2-phenoxy-phenyl)-methanone | (6-Chloro-benzooxazol-2-yl)-(R)-pyrrolidin-3-yl-amine, hydrochloride (intermediate 4) and 2-Phenoxy-benzoic acid (commercially available) | 434.1 |

-continued

| No. | structure | MW | name | starting materials | MW found (MH+) |
|---|---|---|---|---|---|
| 77 | 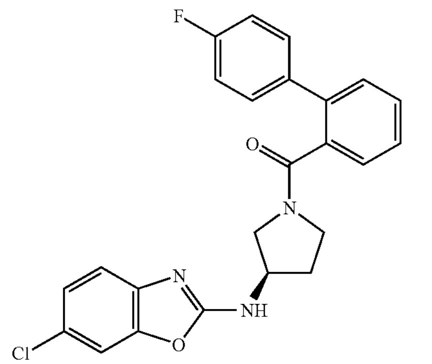 | 435.9 | [(R)-3-(6-Chloro-benzooxazol-2-ylamino)-pyrrolidin-1-yl]-(4'-fluoro-biphenyl-2-yl)-methanone | (6-Chloro-benzooxazol-2-yl)-(R)-pyrrolidin-3-yl-amine, hydrochloride (intermediate 4) and 4'-Fluoro-biphenyl-2-carboxylic acid (commercially available) | 436.1 |
| 78 | 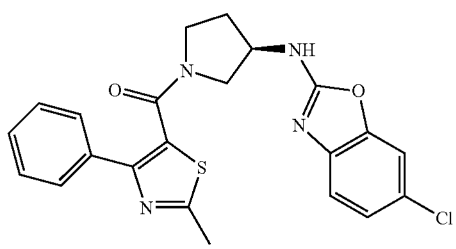 | 438.9 | [(R)-3-(6-Chloro-benzooxazol-2-ylamino)-pyrrolidin-1-yl]-(2-methyl-4-phenyl-thiazol-5-yl)-methanone | (6-Chloro-benzooxazol-2-yl)-(R)-pyrrolidin-3-yl-amine, hydrochloride (intermediate 4) and 2-Methyl-4-phenyl-thiazole-5-carboxylic acid (commercially available) | 439.1 |
| 79 | 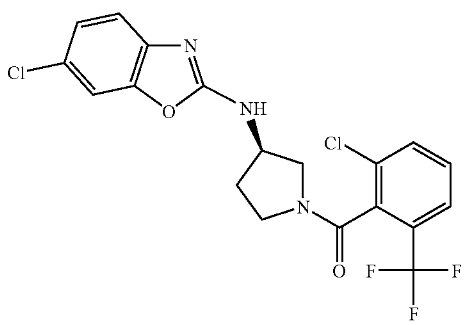 | 444.2 | [(R)-3-(6-Chloro-benzooxazol-2-ylamino)-pyrrolidin-1-yl]-(2-chloro-6-trifluoromethyl-phenyl)-methanone | (6-Chloro-benzooxazol-2-yl)-(R)-pyrrolidin-3-yl-amine, hydrochloride (intermediate 4) and 2-Chloro-6-trifluoromethyl-benzoic acid (commercially available) | 444.1 |
| 80 | 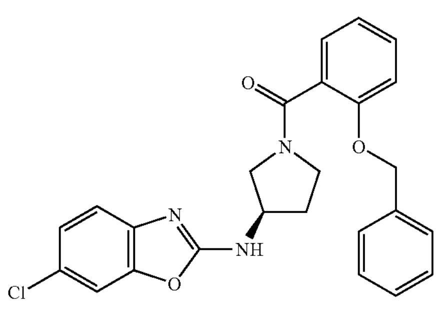 | 447.9 | (2-Benzyloxy-phenyl)-[(R)-3-(6-chloro-benzooxazol-2-ylamino)-pyrrolidin-1-yl]-methanone | (6-Chloro-benzooxazol-2-yl)-(R)-pyrrolidin-3-yl-amine, hydrochloride (intermediate 4) and 2-Benzyloxy-benzoic acid (commercially available) | 448.1 |
| 81 | 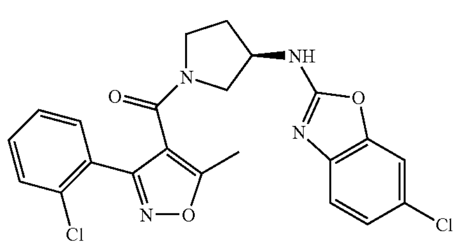 | 457.3 | [(R)-3-(6-Chloro-benzooxazol-2-ylamino)-pyrrolidin-1-yl]-[3-(2-chloro-phenyl)-5-methyl-isoxazol-4-yl]-methanone | (6-Chloro-benzooxazol-2-yl)-(R)-pyrrolidin-3-yl-amine, hydrochloride (intermediate 4) and 3-(2-Chloro-phenyl)-5-methyl-isoxazole-4-carboxylic acid (commerically available) | 457.1 |

| No. | structure | MW | name | starting materials | MW found (MH+) |
|---|---|---|---|---|---|
| 82 | 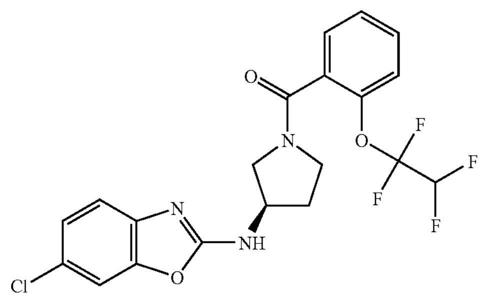 | 457.8 | [(R)-3-(6-Chloro-benzooxazol-2-ylamino)-pyrrolidin-1-yl]-[2-(1,1,2,2-tetrafluoro-ethoxy)-phenyl]-methanone | (6-Chloro-benzooxazol-2-yl)-(R)-pyrrolidin-3-yl-amine, hydrochloride (intermediate 4) and 2-Pentafluoroethyloxy-benzoic acid (commercially available) | 458.1 |
| 83 | 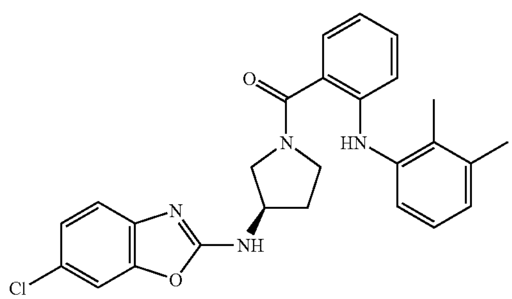 | 461.0 | [(R)-3-(6-Chloro-benzooxazol-2-ylamino)-pyrrolidin-1-yl]-[2-(2,3-dimethyl-phenylamino)-phenyl]-methanone | (6-Chloro-benzooxazol-2-yl)-(R)-pyrrolidin-3-yl-amine, hydrochloride (intermediate 4) and 2-(2,3-Dimethyl-phenylamino)-benzoic acid (commercially available) | 461.2 |
| 84 | 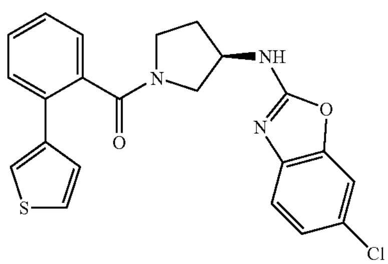 | 423.9 | [(R)-3-(6-Chloro-benzooxazol-2-ylamino)-pyrrolidin-1-yl]-(2-thiophen-3-yl-phenyl)-methanone | (6-Chloro-benzooxazol-2-yl)-(R)-pyrrolidin-3-yl-amine, hydrochloride (intermediate 4) and 2-Thiophen-3-yl-benzoic acid (commercially available) | 424.1 |
| 85 | 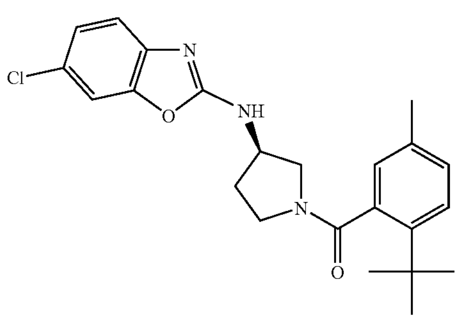 | 411.9 | (2-tert-Butyl-5-methyl-phenyl)-[(R)-3-(6-chloro-benzooxazol-2-ylamino)-pyrrolidin-1-yl]-methanone | (6-Chloro-benzooxazol-2-yl)-(R)-pyrrolidin-3-yl-amine, hydrochloride (intermediate 4) and 2-tert-Butyl-5-methyl-benzoic acid (commercially available) | 412.1 |
| 86 | 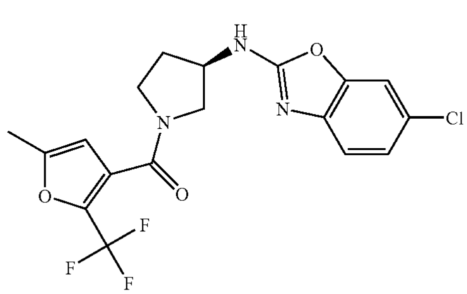 | 413.8 | [(R)-3-(6-Chloro-benzooxazol-2-ylamino)-pyrrolidin-1-yl]-(5-methyl-2-trifluoromethyl-furan-3-yl)-methanone | (6-Chloro-benzooxazol-2-yl)-(R)-pyrrolidin-3-yl-amine, hydrochloride (intermediate 4) and 5-Methyl-2-trifluoromethyl-furan-3-carboxylic acid (commercially available) | 414.1 |

-continued

| No. | structure | MW | name | starting materials | MW found (MH+) |
|---|---|---|---|---|---|
| 87 | 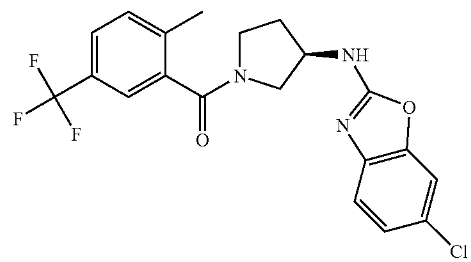 | 423.8 | [(R)-3-(6-Chloro-benzooxazol-2-ylamino)-pyrrolidin-1-yl]-(2-methyl-5-trifluoromethyl-phenyl)-methanone | (6-Chloro-benzooxazol-2-yl)-(R)-pyrrolidin-3-yl-amine, hydrochloride (intermediate 4) and 2-Methyl-5-trifluoromethyl-benzoic acid (commerically available) | 424.1 |
| 88 | 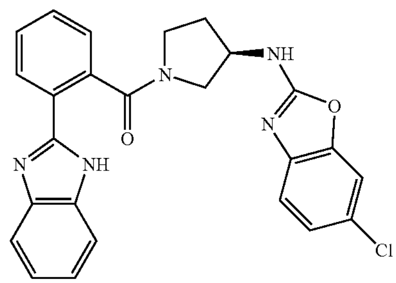 | 457.9 | [2-(1H-Benzoimidazol-2-yl)-phenyl]-[(R)-3-(6-chloro-benzooxazol-2-ylamino)-pyrrolidin-1-yl]-methanone | (6-Chloro-benzooxazol-2-yl)-(R)-pyrrolidin-3-yl-amine, hydrochloride (intermediate 4) and 2-(1H-Benzoimidazol-2-yl)-benzoic acid (commerically available) | 458.1 |
| 89 | 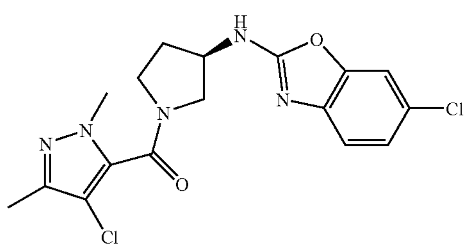 | 394.3 | [(R)-3-(6-Chloro-benzooxazol-2-ylamino)-pyrrolidin-1-yl]-(4-chloro-2,5-dimethyl-2H-pyrazol-3-yl)-methanone | (6-Chloro-benzooxazol-2-yl)-(R)-pyrrolidin-3-yl-amine, hydrochloride (intermediate 4) and 4-Chloro-2,5-dimethyl-2H-pyrazole-3-carboxylic acid (commerically available) | 394.1 |
| 90 | 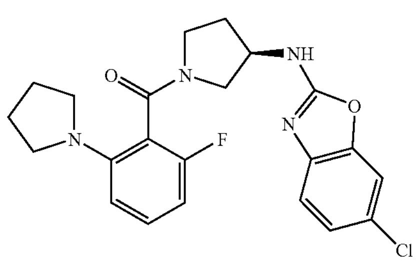 | 428.9 | [(R)-3-(6-Chloro-benzooxazol-2-ylamino)-pyrrolidin-1-yl]-(2-fluoro-6-pyrrolidin-1-yl-phenyl)-methanone | (6-Chloro-benzooxazol-2-yl)-(R)-pyrrolidin-3-yl-amine, hydrochloride (intermediate 4) and 2-Fluoro-6-pyrrolidin-1-yl-benzoic acid (commercially available) | 429.1 |
| 91 | 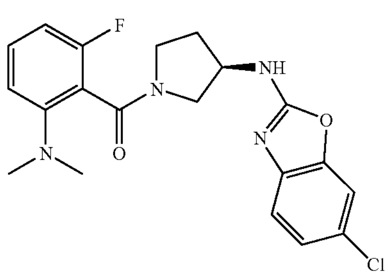 | 402.9 | [(R)-3-(6-Chloro-benzooxazol-2-ylamino)-pyrrolidin-1-yl]-(2-dimethylamino-6-fluoro-phenyl)-methanone | (6-Chloro-benzooxazol-2-yl)-(R)-pyrrolidin-3-yl-amine, hydrochloride (intermediate 4) and 2-Dimethylamino-6-fluoro-benzoic acid (commercially available) | 403.1 |

-continued

| No. | structure | MW | name | starting materials | MW found (MH+) |
|---|---|---|---|---|---|
| 92 | 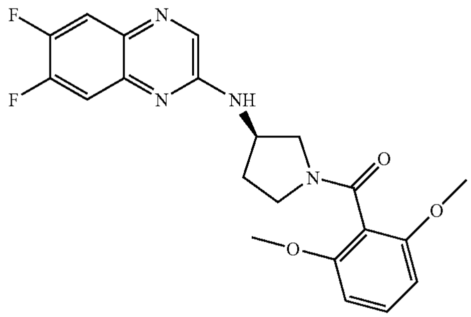 | 414.4 | [(R)-3-(6,7-Difluoro-quinoxalin-2-ylamino)-pyrrolidin-1-yl]-(2,6-dimethoxy-phenyl)-methanone | 2-Chloro-6,7-difluoroquinoxaline (WO2003051368) and ((R)-3-Amino-pyrrolidin-1-yl)-(2,6-dimethoxy-phenyl)-methanone (intermediate 5) | 415.1 |
| 93 | 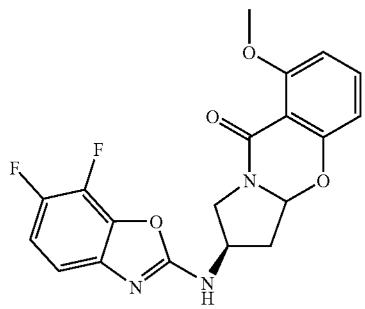 | 403.4 | [(R)-3-(6,7-Difluoro-benzooxazol-2-ylamino)-pyrrolidin-1-yl]-(2,6-dimethoxy-phenyl)-methanone | 2-Chloro-6,7-difluoro-benzooxazole (intermediate 6) and ((R)-3-Amino-pyrrolidin-1-yl)-(2,6-dimethoxy-phenyl)-methanone (intermediate 5) | 404.1 |
| 94 | 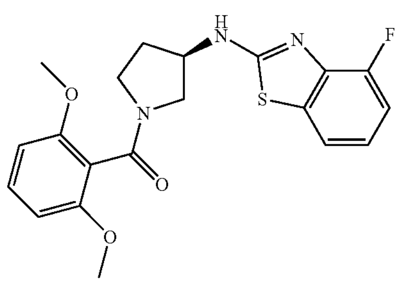 | 401.5 | (2,6-Dimethoxy-phenyl)-[(R)-3-(4-fluoro-benzothiazol-2-ylamino)-pyrrolidin-1-yl]-methanone | 2-Chloro-4-fluorobenzothiazole (commercially available) and ((R)-3-Amino-pyrrolidin-1-yl)-(2,6-dimethoxy-phenyl)-methanone (intermediate 5) | 402.1 |
| 95 | 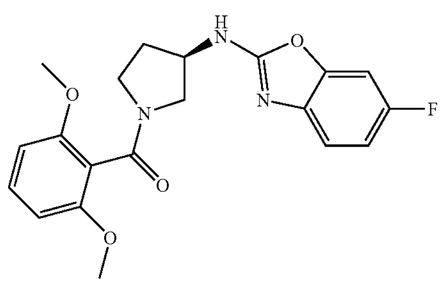 | 385.4 | (2,6-Dimethoxy-phenyl)-[(R)-3-(6-fluoro-benzooxazol-2-ylamino)-pyrrolidin-1-yl]-methanone | 2-Chloro-6-fluorobenzothiazole (Bioorganic & Medicinal Chemistry Letters 2007, 17, 4689) and ((R)-3-Amino-pyrrolidin-1-yl)-(2,6-dimethoxy-phenyl)-methanone (intermediate 5) | 386.1 |
| 96 | 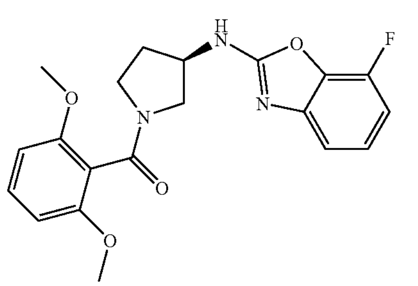 | 385.4 | (2,6-Dimethoxy-phenyl)-[(R)-3-(7-fluoro-benzooxazol-2-ylamino)-pyrrolidin-1-yl]-methanone | 2-Chloro-7-fluorobenzooxazole (Bioorganic & Medicinal Chemistry Letters 2007, 17, 4689) and ((R)-3-Amino-pyrrolidin-1-yl)-(2,6-dimethoxy-phenyl)-methanone (intermediate 5) | 386.1 |

-continued

| No. | structure | MW | name | starting materials | MW found (MH+) |
|---|---|---|---|---|---|
| 97 | 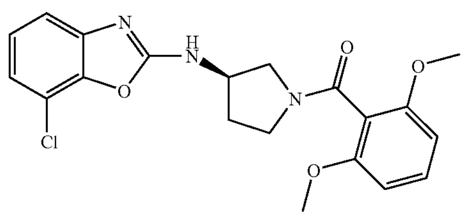 | 401.8 | [(R)-3-(7-Chloro-benzooxazol-2-ylamino)-pyrrolidin-1-yl]-(2,6-dimethoxy-phenyl)-methanone | 2,7-Dichlorobenzoxazole (WO8301448A1) and ((R)-3-Amino-pyrrolidin-1-yl)-(2,6-dimethoxy-phenyl)-methanone (intermediate 5) | 402.1 |
| 98 | 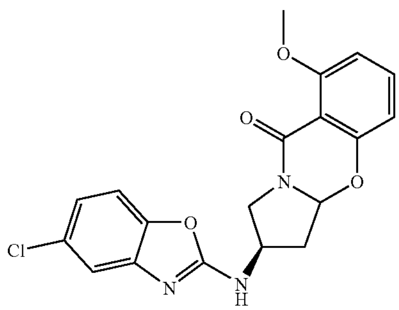 | 401.8 | [(R)-3-(5-Chloro-benzooxazol-2-ylamino)-pyrrolidin-1-yl]-(2,6-dimethoxy-phenyl)-methanone | 2,6-Dichlorobenzoxazole (commercially available) and ((R)-3-Amino-pyrrolidin-1-yl)-(2,6-dimethoxy-phenyl)-methanone (intermediate 5) | 402.1 |
| 99 | 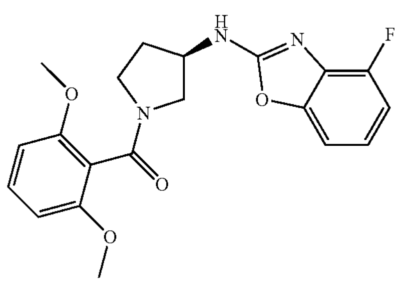 | 385.4 | (2,6-Dimethoxy-phenyl)-[(R)-3-(4-fluoro-benzooxazol-2-ylamino)-pyrrolidin-1-yl]-methanone | 2-Chloro-4-fluoro-benzooxazole (intermediate 7) and ((R)-3-Amino-pyrrolidin-1-yl)-(2,6-dimethoxy-phenyl)-methanone (intermediate 5) | 386.1 |
| 100 | 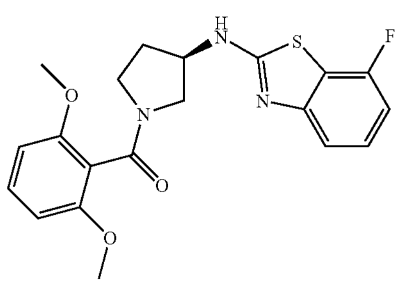 | 401.5 | (2,6-Dimethoxy-phenyl)-[(R)-3-(7-fluoro-benzothiazol-2-ylamino)-pyrrolidin-1-yl]-methanone | 2-Chloro-7-fluorobenzothiazole (commercially available) and ((R)-3-Amino-pyrrolidin-1-yl)-(2,6-dimethoxy-phenyl)-methanone (intermediate 5) | 402.1 |
| 101 | 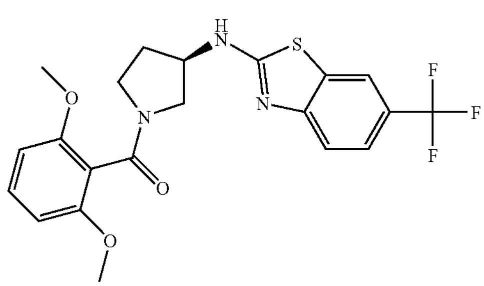 | 451.5 | (2,6-Dimethoxy-phenyl)-[(R)-3-(6-trifluoromethyl-benzothiazol-2-ylamino)-pyrrolidin-1-yl]-methanone | 2-Chloro-6-trifluoromethylbenzothiazole (commercially available) and ((R)-3-Amino-pyrrolidin-1-yl)-(2,6-dimethoxy-phenyl)-methanone (intermediate 5) | 452.1 |

-continued

| No. | structure | MW | name | starting materials | MW found (MH+) |
|---|---|---|---|---|---|
| 102 | 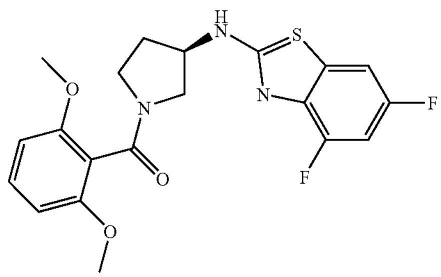 | 419.5 | [(R)-3-(5,7-Difluoro-benzothiazol-2-ylamino)-pyrrolidin-1-yl]-(2,6-dimethoxy-phenyl)-methanone | 2-Chloro-5,7-difluorobenzothiazole (commercially available) and ((R)-3-Amino-pyrrolidin-1-yl)-(2,6-dimethoxy-phenyl)-methanone (intermediate 5) | 420.1 |
| 103 | 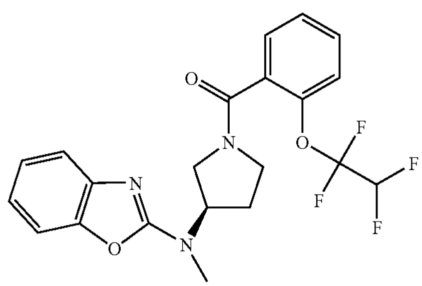 | 437.4 | [(R)-3-(Benzooxazol-2-yl-methyl-amino)-pyrrolidin-1-yl]-[2-(1,1,2,2-tetrafluoro-ethoxy)-phenyl]-methanone | Benzooxazol-2-yl-methyl-(R)-pyrrolidin-3-yl-amine (intermediate 8) and 2-(1,1,2,2-Tetrafluoro-ethoxy)-benzoic acid (commercially available) | 438.2 |
| 104 | 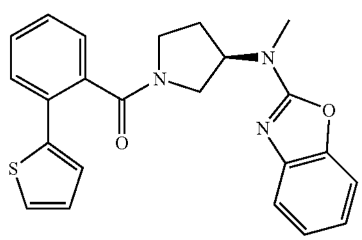 | 403.5 | [(R)-3-(Benzooxazol-2-yl-methyl-amino)-pyrrolidin-1-yl]-(2-thiophen-2-yl-phenyl)-methanone | Benzooxazol-2-yl-methyl-(R)-pyrrolidin-3-yl-amine (intermediate 8) and 2-Thiophen-2-yl-benzoic acid (commercially available) | 404.2 |
| 105 | 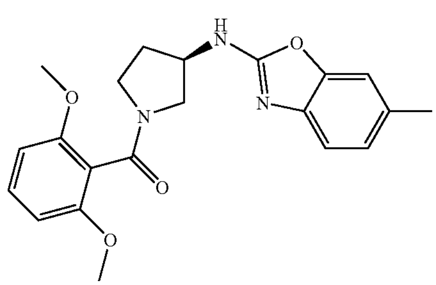 | 381.4 | (2,6-Dimethoxy-phenyl)-[(R)-3-(6-methyl-benzooxazol-2-ylamino)-pyrrolidin-1-yl]-methanone | 2-Chloro-6-methylbenzooxazole (Organic Process Research & Development, 1997, 1, 331) and ((R)-3-Amino-pyrrolidin-1-yl)-(2,6-dimethoxy-phenyl)-methanone (intermediate 5) | 382.2 |
| 106 | 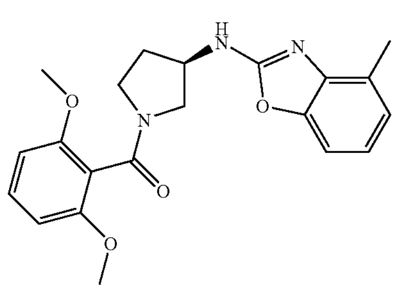 | 381.4 | (2,6-Dimethoxy-phenyl)-[(R)-3-(4-methyl-benzooxazol-2-ylamino)-pyrrolidin-1-yl]-methanone | 2-Chloro-6-methylbenzooxazole (WO2008005368) and ((R)-3-Amino-pyrrolidin-1-yl)-(2,6-dimethoxy-phenyl)-methanone (intermediate 5) | 382.2 |

-continued

| No. | structure | MW | name | starting materials | MW found (MH+) |
|---|---|---|---|---|---|
| 107 | 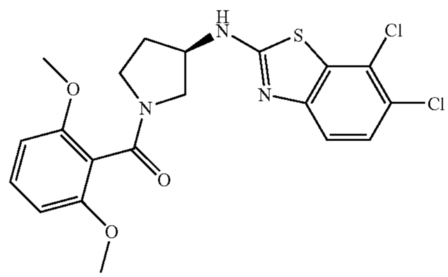 | 452.4 | [(R)-3-(6,7-Dichloro-benzothiazol-2-ylamino)-pyrrolidin-1-yl]-(2,6-dimethoxy-phenyl)-methanone | 2,6,7-Trichloro-benzothiazole (intermediate 9) and ((R)-3-Amino-pyrrolidin-1-yl)-(2,6-dimethoxy-phenyl)-methanone (intermediate 5) | 452.1 |
| 108 | 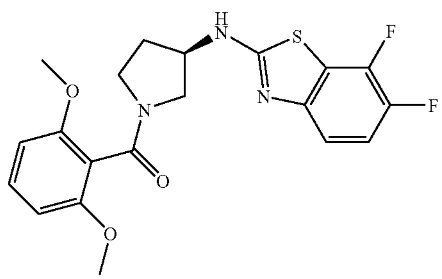 | 419.5 | [(R)-3-(6,7-Difluoro-benzothiazol-2-ylamino)-pyrrolidin-1-yl]-(2,6-dimethoxy-phenyl)-methanone | 2-chloro-6,7-difluoro-benzthiazole (WO2007146066) and ((R)-3-Amino-pyrrolidin-1-yl)-(2,6-dimethoxy-phenyl)-methanone (intermediate 5) | 420.1 |
| 109 | 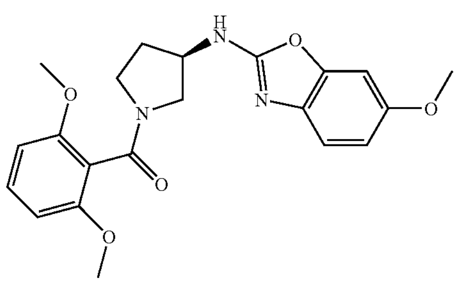 | 397.4 | (2,6-Dimethoxy-phenyl)-[(R)-3-(6-methoxy-benzooxazol-2-ylamino)-pyrrolidin-1-yl]-methanone | 2-Chloro-6-methoxybenzoxazole (EP621271) and ((R)-3-Amino-pyrrolidin-1-yl)-(2,6-dimethoxy-phenyl)-methanone (intermediate 5) | 398.2 |
| 110 | 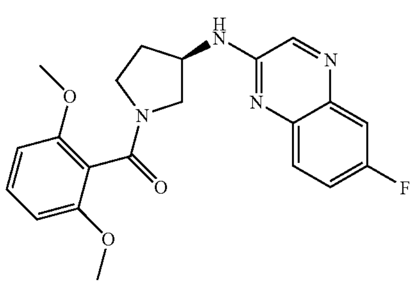 | 396.4 | (2,6-Dimethoxy-phenyl)-[(R)-3-(6-fluoro-quinoxalin-2-ylamino)-pyrrolidin-1-yl]-methanone | 2-Chloro-6-fluoroquinoxaline (commercially available) and ((R)-3-Amino-pyrrolidin-1-yl)-(2,6-dimethoxy-phenyl)-methanone (intermediate 5) | 397.2 |
| 111 | 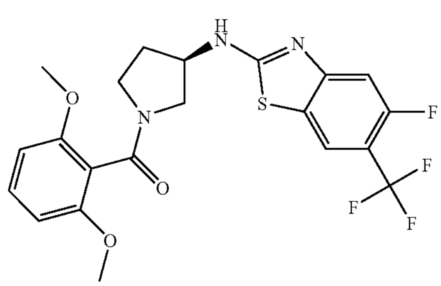 | 469.5 | (2,6-Dimethoxy-phenyl)-[(R)-3-(5-fluoro-6-trifluoromethyl-benzothiazol-2-ylamino)-pyrrolidin-1-yl]-methanone | 2-Chloro-5-fluoro-6-trifluoromethylbenzothiazole (WO2007023882) and ((R)-3-Amino-pyrrolidin-1-yl)-(2,6-dimethoxy-phenyl)-methanone (intermediate 5) | 470.2 |

| No. | structure | MW | name | starting materials | MW found (MH+) |
|---|---|---|---|---|---|
| 112 | 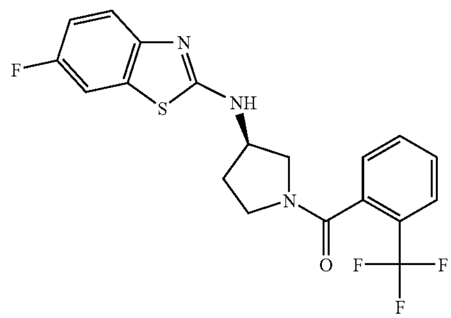 | 409.4 | [(R)-3-(6-Fluoro-benzothiazol-2-ylamino)-pyrrolidin-1-yl]-(2-trifluoromethyl-phenyl)-methanone | 2-Chloro-6-fluorobenzothiazole (commercially available) and ((R)-3-Amino-pyrrolidin-1-yl)-(2-trifluoromethyl-phenyl)-methanone (intermediate 10) | 410.1 |
| 113 | 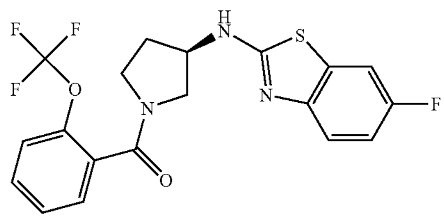 | 425.4 | [(R)-3-(6-Fluoro-benzothiazol-2-ylamino)-pyrrolidin-1-yl]-(2-trifluoromethoxy-phenyl)-methanone | 2-Chloro-6-fluorobenzothiazole (commercially available) and ((R)-3-Amino-pyrrolidin-1-yl)-(2-trifluoromethoxy-phenyl)-methanone (intermediate 11) | 426.1 |
| 114 | 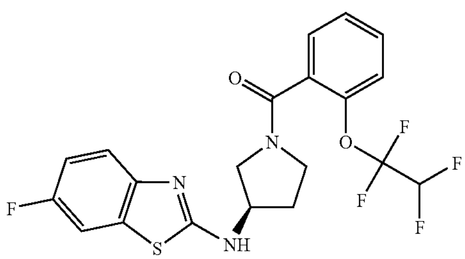 | 457.4 | [(R)-3-(6-Fluoro-benzothiazol-2-ylamino)-pyrrolidin-1-yl]-[2-(1,1,2,2-tetrafluoro-ethoxy)-phenyl]-methanone | 2-Chloro-6-fluorobenzothiazole (commercially available) and ((R)-3-Amino-pyrrolidin-1-yl)-[2-(1,1,2,2-tetrafluoro-ethoxy)-phenyl]-methanone (intermediate 12) | 458.2 |
| 115 | 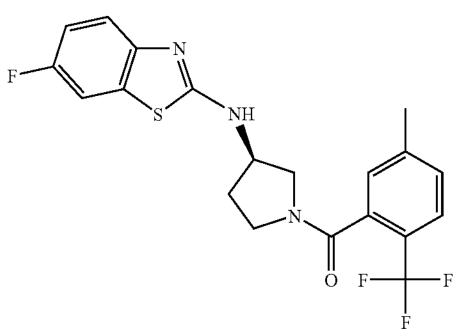 | 423.4 | [(R)-3-(6-Fluoro-benzothiazol-2-ylamino)-pyrrolidin-1-yl]-(5-methyl-2-trifluoromethyl-phenyl)-methanone | 2-Chloro-6-fluorobenzothiazole (commercially available) and ((R)-3-Amino-pyrrolidin-1-yl)-(5-methyl-2-trifluoromethyl-phenyl)-methanone (intermediate 13) | 424.1 |
| 116 | 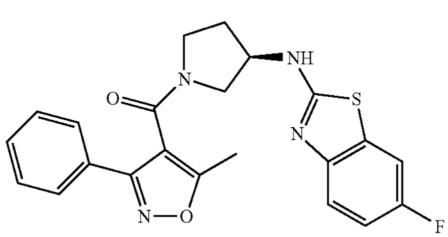 | 422.5 | [(R)-3-(6-Fluoro-benzothiazol-2-ylamino)-pyrrolidin-1-yl]-(5-methyl-3-phenyl-isoxazol-4-yl)-methanone | 2-Chloro-6-fluorobenzothiazole (commercially available) and ((R)-3-Amino-pyrrolidin-1-yl)-(5-methyl-3-phenyl-isoxazol-4-yl)-methanone (intermediate 14) | 423.2 |

-continued

| No. | structure | MW | name | starting materials | MW found (MH+) |
|---|---|---|---|---|---|
| 117 | 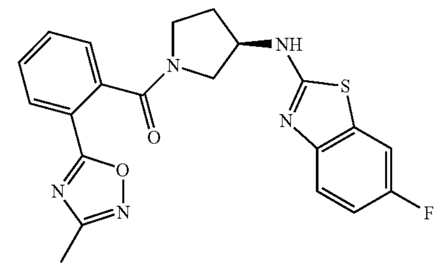 | 423.5 | [(R)-3-(6-Fluoro-benzothiazol-2-ylamino)-pyrrolidin-1-yl]-[2-(3-methyl-[1,2,4]oxadiazol-5-yl)-phenyl]-methanone | 2-Chloro-6-fluorobenzothiazole (commercially available) and ((R)-3-Amino-pyrrolidin-1-yl)-[2-(3-methyl-[1,2,4]oxadiazol-5-yl)-phenyl]-methanone (intermediate 15) | 424.1 |
| 118 | 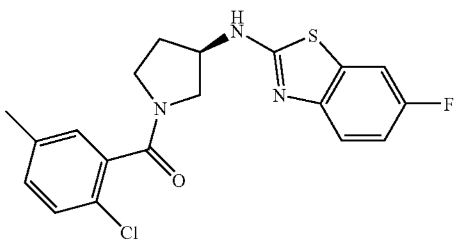 | 389.9 | (2-Chloro-5-methyl-phenyl)-[(R)-3-(6-fluoro-benzothiazol-2-ylamino)-pyrrolidin-1-yl]-methanone | 2-Chloro-6-fluorobenzothiazole (commercially available) and ((R)-3-Amino-pyrrolidin-1-yl)-(2-chloro-5-methyl-phenyl)-methanone (intermediate 16) | 390.1 |
| 119 | 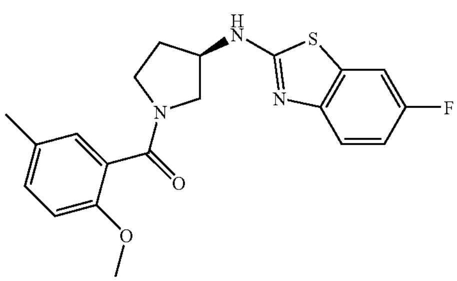 | 385.5 | [(R)-3-(6-Fluoro-benzothiazol-2-ylamino)-pyrrolidin-1-yl]-(2-methoxy-5-methyl-phenyl)-methanone | 2-Chloro-6-fluorobenzothiazole (commercially available) and ((R)-3-Amino-pyrrolidin-1-yl)-(2-methoxy-5-methyl-phenyl)-methanone (intermediate 17) | 386.1 |
| 120 | 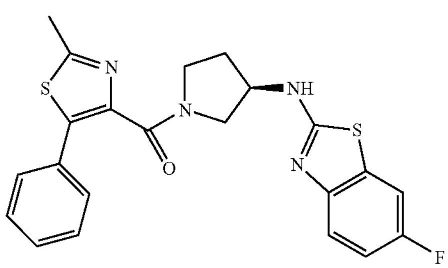 | 438.5 | [(R)-3-(6-Fluoro-benzothiazol-2-ylamino)-pyrrolidin-1-yl]-(2-methyl-5-phenyl-thiazol-4-yl)-methanone | 2-Chloro-6-fluorobenzothiazole (commercially available) and ((R)-3-Amino-pyrrolidin-1-yl)-(2-methyl-5-phenyl-thiazol-4-yl)-methanone (intermediate 18) | 439.1 |
| 121 | 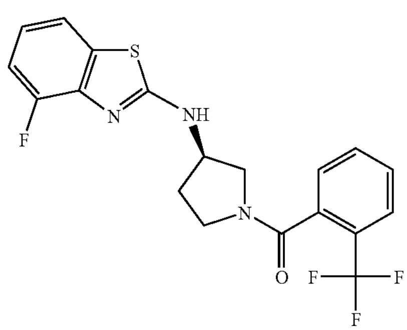 | 409.4 | [(R)-3-(4-Fluoro-benzothiazol-2-ylamino)-pyrrolidin-1-yl]-(2-trifluoromethyl-phenyl)-methanone | 2-Chloro-4-fluorobenzothiazole (commercially available) and ((R)-3-Amino-pyrrolidin-1-yl)-(2-trifluoromethyl-phenyl)-methanone (intermediate 10) | 410.1 |

-continued

| No. | structure | MW | name | starting materials | MW found (MH+) |
|---|---|---|---|---|---|
| 122 | 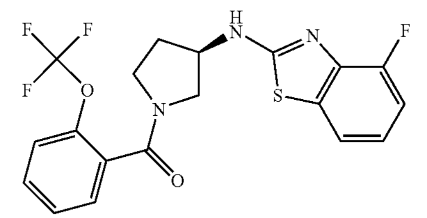 | 425.4 | [(R)-3-(4-Fluoro-benzothiazol-2-ylamino)-pyrrolidin-1-yl]-(2-trifluoromethoxy-phenyl)-methanone | 2-Chloro-4-fluorobenzothiazole (commercially available) and ((R)-3-Amino-pyrrolidin-1-yl)-(2-trifluoromethoxy-phenyl)-methanone (intermediate 11) | 426.1 |
| 123 | 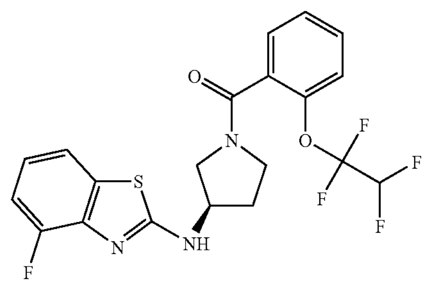 | 457.4 | [(R)-3-(4-Fluoro-benzothiazol-2-ylamino)-pyrrolidin-1-yl]-[2-(1,1,2,2-tetrafluoro-ethoxy)-phenyl]-methanone | 2-Chloro-4-fluorobenzothiazole (commercially available) and ((R)-3-Amino-pyrrolidin-1-yl)-[2-(1,1,2,2-tetrafluoro-ethoxy)-phenyl]-methanone (intermediate 12) | 458.1 |
| 124 | 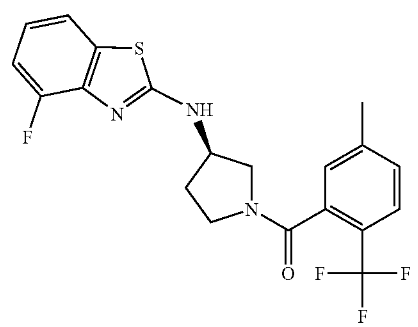 | 423.4 | [(R)-3-(4-Fluoro-benzothiazol-2-ylamino)-pyrrolidin-1-yl]-(5-methyl-2-trifluoromethyl-phenyl)-methanone | 2-Chloro-4-fluorobenzothiazole (commercially available) and ((R)-3-Amino-pyrrolidin-1-yl)-(5-methyl-2-trifluoromethyl-phenyl)-methanone (intermediate 13) | 424.1 |
| 125 | 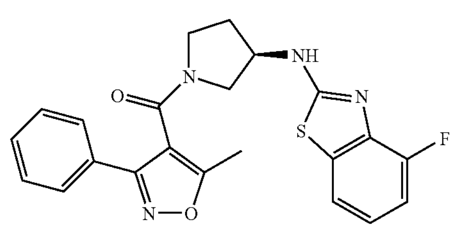 | 422.5 | [(R)-3-(4-Fluoro-benzothiazol-2-ylamino)-pyrrolidin-1-yl]-(5-methyl-3-phenyl-isoxazol-4-yl)-methanone | 2-Chloro-4-fluorobenzothiazole (commercially available) and ((R)-3-Amino-pyrrolidin-1-yl)-(5-methyl-3-phenyl-isoxazol-4-yl)-methanone (intermediate 14) | 423.1 |
| 126 | 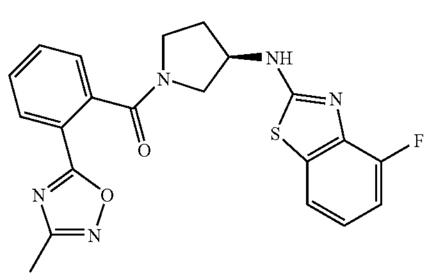 | 423.5 | [(R)-3-(4-Fluoro-benzothiazol-2-ylamino)-pyrrolidin-1-yl]-[2-(3-methyl-[1,2,4]oxadiazol-5-yl)-phenyl]-methanone | 2-Chloro-4-fluorobenzothiazole (commercially available) and ((R)-3-Amino-pyrrolidin-1-yl)-[2-(3-methyl-[1,2,4]oxadiazol-5-yl)-phenyl]-methanone (intermediate 15) | 424.1 |

-continued

| No. | structure | MW | name | starting materials | MW found (MH+) |
|---|---|---|---|---|---|
| 127 | 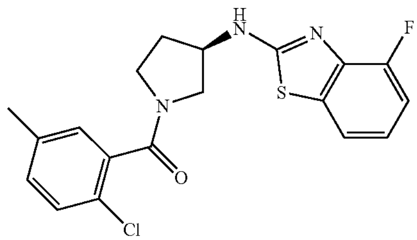 | 389.9 | (2-Chloro-5-methyl-phenyl)-[(R)-3-(4-fluoro-benzothiazol-2-ylamino)-pyrrolidin-1-yl]-methanone | 2-Chloro-4-fluorobenzothiazole (commercially available) and ((R)-3-Amino-pyrrolidin-1-yl)-(2-chloro-5-methyl-phenyl)-methanone (intermediate 16) | 390.1 |
| 128 | 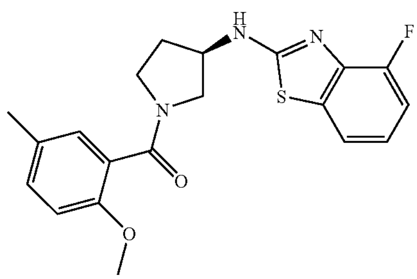 | 385.5 | [(R)-3-(4-Fluoro-benzothiazol-2-ylamino)-pyrrolidin-1-yl]-(2-methoxy-5-methyl-phenyl)-methanone | 2-Chloro-4-fluorobenzothiazole (commercially available) and ((R)-3-Amino-pyrrolidin-1-yl)-(2-methoxy-5-methyl-phenyl)-methanone (intermediate 17) | 386.1 |
| 129 | 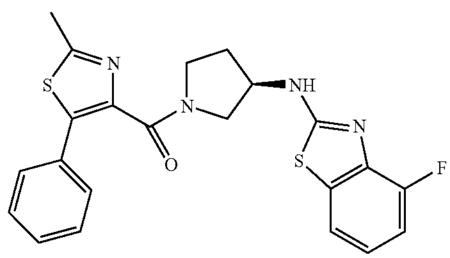 | 438.5 | [(R)-3-(4-Fluoro-benzothiazol-2-ylamino)-pyrrolidin-1-yl]-(2-methyl-5-phenyl-thiazol-4-yl)-methanone | 2-Chloro-4-fluorobenzothiazole (commercially available) and ((R)-3-Amino-pyrrolidin-1-yl)-(2-methyl-5-phenyl-thiazol-4-yl)-methanone (intermediate 18) | 439.1 |
| 130 | 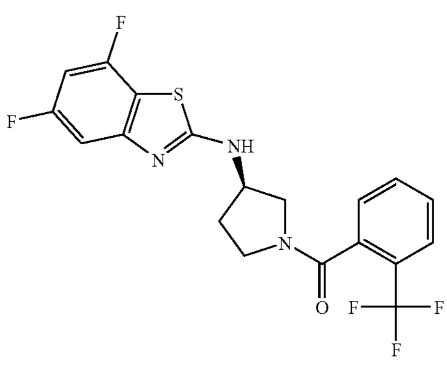 | 427.4 | [(R)-3-(5,7-Difluoro-benzothiazol-2-ylamino)-pyrrolidin-1-yl]-(2-trifluoromethyl-phenyl)-methanone | 2-Chloro-5,7-difluorobenzothiazole (commercially available) and ((R)-3-Amino-pyrrolidin-1-yl)-(2-trifluoromethyl-phenyl)-methanone (intermediate 10) | 428.1 |
| 131 | 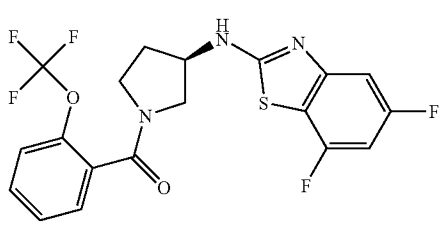 | 443.4 | [(R)-3-(5,7-Difluoro-benzothiazol-2-ylamino)-pyrrolidin-1-yl]-(2-trifluoromethoxy-phenyl)-methanone | 2-Chloro-5,7-difluorobenzothiazole (commercially available) and ((R)-3-Amino-pyrrolidin-1-yl)-(2-trifluoromethoxy-phenyl)-methanone (intermediate 11) | 444.1 |

-continued

| No. | structure | MW | name | starting materials | MW found (MH+) |
|---|---|---|---|---|---|
| 132 | 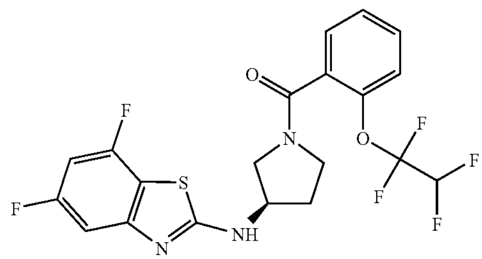 | 475.4 | [(R)-3-(5,7-Difluoro-benzothiazol-2-ylamino)-pyrrolidin-1-yl]-[2-(1,1,2,2-tetrafluoro-ethoxy)-phenyl]-methanone | 2-Chloro-5,7-difluorobenzothiazole (commercially available) and ((R)-3-Amino-pyrrolidin-1-yl)-[2-(1,1,2,2-tetrafluoro-ethoxy)-phenyl]-methanone (intermediate 12) | 476.2 |
| 133 | 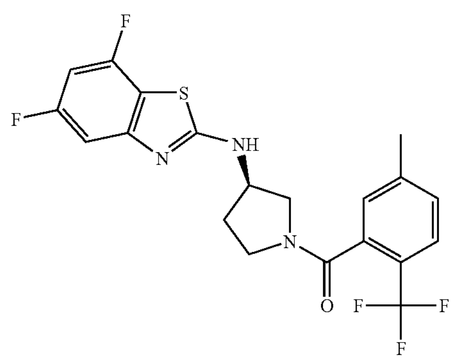 | 441.4 | [(R)-3-(5,7-Difluoro-benzothiazol-2-ylamino)-pyrrolidin-1-yl]-(5-methyl-2-trifluoromethyl-phenyl)-methanone | 2-Chloro-5,7-difluorobenzothiazol (commercially available) and ((R)-3-Amino-pyrrolidin-1-yl)-(5-methyl-2-trifluoromethyl-phenyl)-methanone (intermediate 13) | 442.1 |
| 134 | 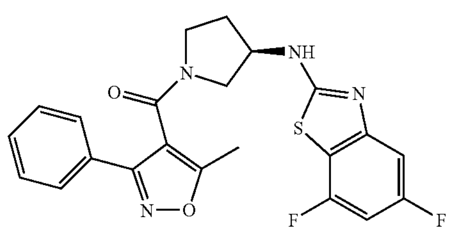 | 440.5 | [(R)-3-(5,7-Difluoro-benzothiazol-2-ylamino)-pyrrolidin-1-yl]-(5-methyl-3-phenyl-isoxazol-4-yl)-methanone | 2-Chloro-5,7-difluorobenzothiazole (commercially available) and ((R)-3-Amino-pyrrolidin-1-yl)-(5-methyl-3-phenyl-isoxazol-4-yl)-methanone (intermediate 14) | 441.1 |
| 135 | 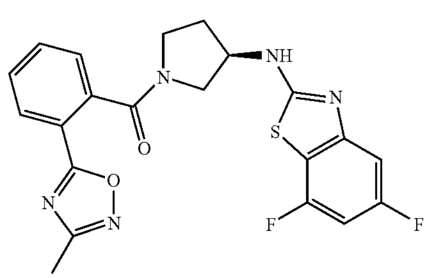 | 441.5 | [(R)-3-(5,7-Difluoro-benzothiazol-2-ylamino)-pyrrolidin-1-yl]-[2-(3-methyl-[1,2,4]oxadiazol-5-yl)-phenyl]-methanone | 2-Chloro-5,7-difluorobenzothiazole (commercially available) and ((R)-3-Amino-pyrrolidin-1-yl)-[2-(3-methyl-[1,2,4]oxadiazol-5-yl)-phenyl]-methanone (intermediate 15) | 442.2 |
| 136 | 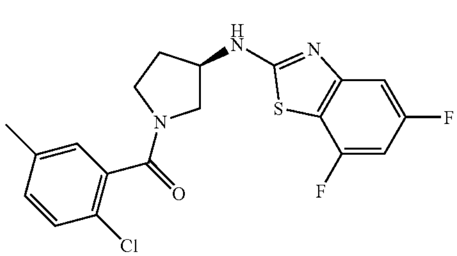 | 407.9 | (2-Chloro-5-methyl-phenyl)-[(R)-3-(5,7-difluoro-benzothiazol-2-ylamino)-pyrrolidin-1-yl]-methanone | 2-Chloro-5,7-difluorobenzothiazole (commercially available) and ((R)-3-Amino-pyrrolidin-1-yl)-(2-chloro-5-methyl-phenyl)-methanone (intermediate 16) | 408.1 |

-continued

| No. | structure | MW | name | starting materials | MW found (MH+) |
|---|---|---|---|---|---|
| 137 | 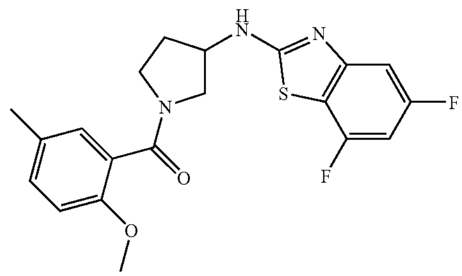 | 403.5 | [(R)-3-(5,7-Difluoro-benzothiazol-2-ylamino)-pyrrolidin-1-yl]-(2-methoxy-5-methyl-phenyl)-methanone | 2-Chloro-5,7-difluorobenzothiazole (commercially available) and ((R)-3-Amino-pyrrolidin-1-yl)-(2-methoxy-5-methyl-phenyl)-methanone (intermediate 17) | 404.2 |
| 138 | 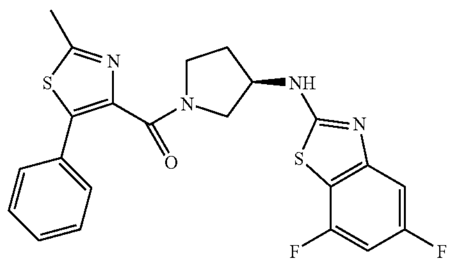 | 456.5 | [(R)-3-(5,7-Difluoro-benzothiazol-2-ylamino)-pyrrolidin-1-yl]-(2-methyl-5-phenyl-thiazol-4-yl)-methanone | 2-Chloro-5,7-difluorobenzothiazole (commercially available) and ((R)-3-Amino-pyrrolidin-1-yl)-(2-methyl-5-phenyl-thiazol-4-yl)-methanone (intermediate 18) | 457.1 |
| 139 | 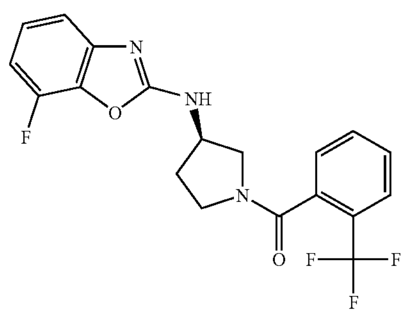 | 393.3 | [(R)-3-(7-Fluoro-benzooxazol-2-ylamino)-pyrrolidin-1-yl]-(2-trifluoromethyl-phenyl)-methanone | 2-Chloro-7-fluorobenzooxazole (Bioorganic & Medicinal Chemistry Letters 2007, 17, 4689) and ((R)-3-Amino-pyrrolidin-1-yl)-(2-trifluoromethyl-phenyl)-methanone (intermediate 10) | 394.1 |
| 140 | 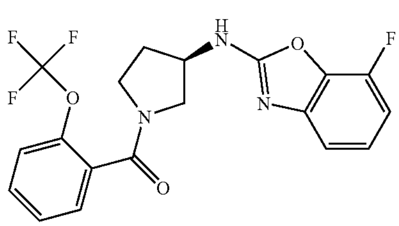 | 409.3 | [(R)-3-(7-Fluoro-benzooxazol-2-ylamino)-pyrrolidin-1-yl]-(2-trifluoromethoxy-phenyl)-methanone | 2-Chloro-7-fluorobenzooxazole (Bioorganic & Medicinal Chemistry Letters 2007, 17, 4689) and ((R)-3-Amino-pyrrolidin-1-yl)-(2-trifluoromethoxy-phenyl)-methanone (intermediate 11) | 410.1 |
| 141 | 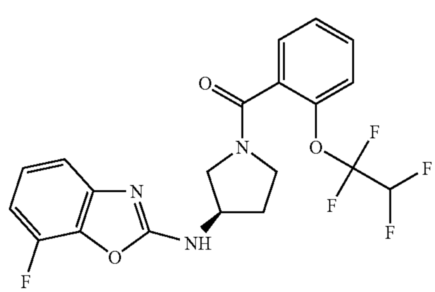 | 441.4 | [(R)-3-(7-Fluoro-benzooxazol-2-ylamino)-pyrrolidin-1-yl]-[2-(1,1,2,2-tetrafluoro-ethoxy)-phenyl]-methanone | 2-Chloro-7-fluorobenzooxazole (Bioorganic & Medicinal Chemistry Letters 2007, 17, 4689) and ((R)-3-Amino-pyrrolidin-1-yl)-[2-(1,1,2,2-tetrafluoro-ethoxy)-phenyl]-methanone (intermediate 12) | 442.1 |

-continued

| No. | structure | MW | name | starting materials | MW found (MH+) |
|---|---|---|---|---|---|
| 142 | 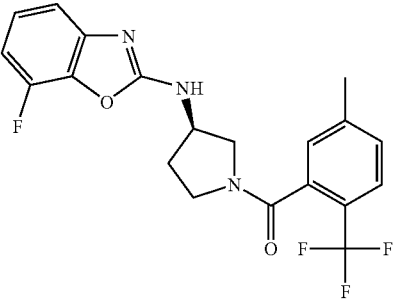 | 407.4 | [(R)-3-(7-Fluoro-benzooxazol-2-ylamino)-pyrrolidin-1-yl]-(5-methyl-2-trifluoromethyl-phenyl)-methanone | 2-Chloro-7-fluorobenzooxazole (Bioorganic & Medicinal Chemistry Letters 2007, 17, 4689) and ((R)-3-Amino-pyrrolidin-1-yl)-(5-methyl-2-trifluoromethyl-phenyl)-methanone (intermediate 13) | 408.2 |
| 143 | 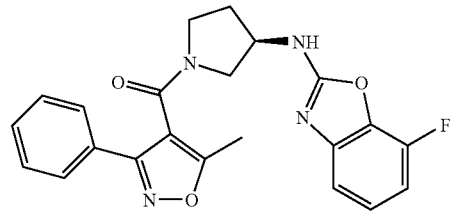 | 406.4 | [(R)-3-(7-Fluoro-benzooxazol-2-ylamino)-pyrrolidin-1-yl]-(5-methyl-3-phenyl-isoxazol-4-yl)-methanone | 2-Chloro-7-fluorobenzooxazole (Bioorganic & Medicinal Chemistry Letters 2007, 17, 4689) and ((R)-3-Amino-pyrrolidin-1-yl)-(5-methyl-3-phenyl-isoxazol-4-yl)-methanone (intermediate 14) | 407.2 |
| 144 | 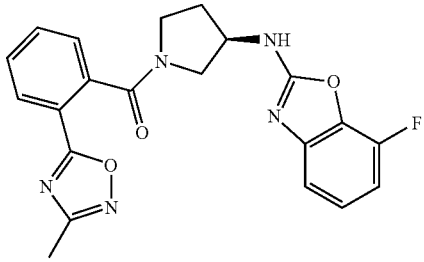 | 407.4 | [(R)-3-(7-Fluoro-benzooxazol-2-ylamino)-pyrrolidin-1-yl]-[2-(3-methyl-[1,2,4]oxadiazol-5-yl)-phenyl]-methanone | 2-Chloro-7-fluorobenzooxazole (Bioorganic & Medicinal Chemistry Letters 2007, 17, 4689) and ((R)-3-Amino-pyrrolidin-1-yl)-[2-(3-methyl-[1,2,4]oxadiazol-5-yl)-phenyl]-methanone (intermediate 15) | 408.2 |
| 145 | 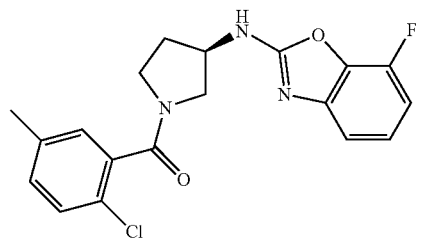 | 373.8 | (2-Chloro-5-methyl-phenyl)-[(R)-3-(7-fluoro-benzooxazol-2-ylamino)-pyrrolidin-1-yl]-methanone | 2-Chloro-7-fluorobenzooxazole (Bioorganic & Medicinal Chemistry Letters 2007, 17, 4689) and ((R)-3-Amino-pyrrolidin-1-yl)-(2-chloro-5-methyl-phenyl)-methanone (intermediate 16) | 374.1 |
| 146 | 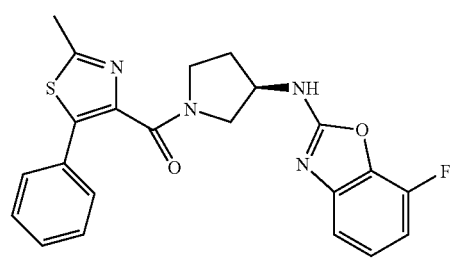 | 422.5 | [(R)-3-(7-Fluoro-benzooxazol-2-ylamino)-pyrrolidin-1-yl]-(2-methyl-5-phenyl-thiazol-4-yl)-methanone | 2-Chloro-7-fluorobenzooxazole (Bioorganic & Medicinal Chemistry Letters 2007, 17, 4689) and ((R)-3-Amino-pyrrolidin-1-yl)-(2-methyl-5-phenyl-thiazol-4-yl)-methanone (intermediate 18) | 423.1 |

-continued

| No. | structure | MW | name | starting materials | MW found (MH+) |
|---|---|---|---|---|---|
| 147 | 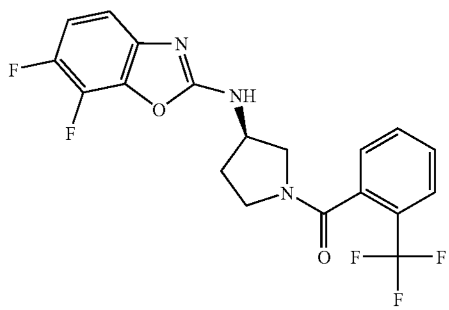 | 411.3 | [(R)-3-(6,7-Difluoro-benzooxazol-2-ylamino)-pyrrolidin-1-yl]-(2-trifluoromethyl-phenyl)-methanone | (6,7-Difluoro-benzooxazol-2-yl)-(R)-pyrrolidin-3-yl-amine (intermediate 6) and ((R)-3-Amino-pyrrolidin-1-yl)-(2-trifluoromethyl-phenyl)-methanone (intermediate 10) | 412.1 |
| 148 | 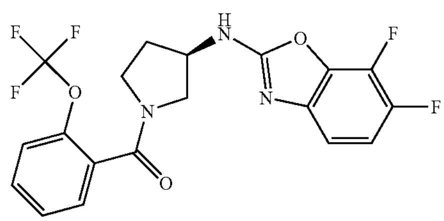 | 427.3 | [(R)-3-(6,7-Difluoro-benzooxazol-2-ylamino)-pyrrolidin-1-yl]-(2-trifluoromethoxy-phenyl)-methanone | (6,7-Difluoro-benzooxazol-2-yl)-(R)-pyrrolidin-3-yl-amine (intermediate 6) and ((R)-3-Amino-pyrrolidin-1-yl)-(2-trifluoromethoxy-phenyl)-methanone (intermediate 11) | 428.1 |
| 149 | 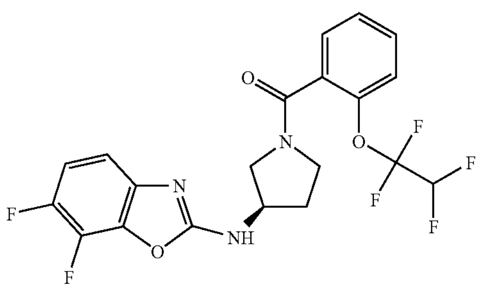 | 459.3 | [(R)-3-(6,7-Difluoro-benzooxazol-2-ylamino)-pyrrolidin-1-yl]-[2-(1,1,2,2-tetrafluoro-ethoxy)-phenyl]-methanone | (6,7-Difluoro-benzooxazol-2-yl)-(R)-pyrrolidin-3-yl-amine (intermediate 6) and ((R)-3-Amino-pyrrolidin-1-yl)-[2-(1,1,2,2-tetrafluoro-ethoxy)-phenyl]-methanone (intermediate 12) | 460.2 |
| 150 | 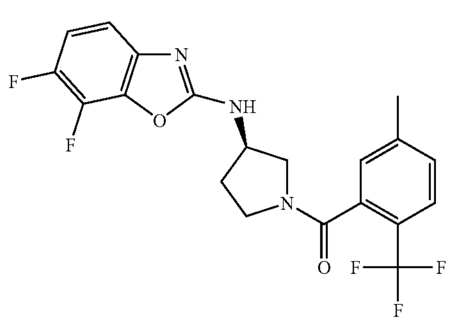 | 425.4 | [(R)-3-(6,7-Difluoro-benzooxazol-2-ylamino)-pyrrolidin-1-yl]-(5-methyl-2-trifluoromethyl-phenyl)-methanone | (6,7-Difluoro-benzooxazol-2-yl)-(R)-pyrrolidin-3-yl-amine (intermediate 6) and ((R)-3-Amino-pyrrolidin-1-yl)-(5-methyl-2-trifluoromethyl-phenyl)-methanone (intermediate 13) | 426.1 |
| 151 | 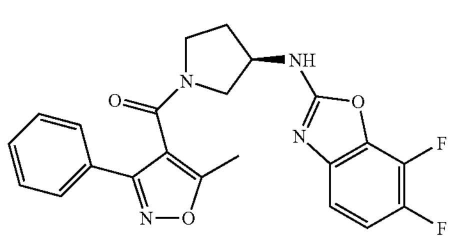 | 424.4 | [(R)-3-(6,7-Difluoro-benzooxazol-2-ylamino)-pyrrolidin-1-yl]-(5-methyl-3-phenyl-isoxazol-4-yl)-methanone | (6,7-Difluoro-benzooxazol-2-yl)-(R)-pyrrolidin-3-yl-amine (intermediate 6) and ((R)-3-Amino-pyrrolidin-1-yl)-(5-methyl-3-phenyl-isoxazol-4-yl)-methanone (intermediate 14) | 425.2 |

| No. | structure | MW | name | starting materials | MW found (MH+) |
|---|---|---|---|---|---|
| 152 | 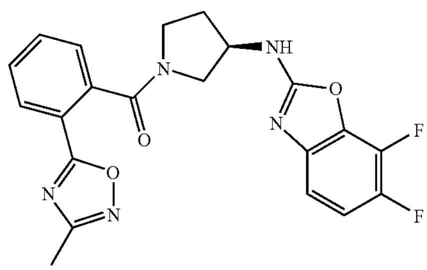 | 425.4 | [(R)-3-(6,7-Difluoro-benzooxazol-2-ylamino)-pyrrolidin-1-yl]-[2-(-methyl-[1,2,4]oxadiazol-5-yl)-phenyl]-methanone | (6,7-Difluoro-benzooxazol-2-yl)-(R)-pyrrolidin-3-yl-amine (intermediate 6) and ((R)-3-Amino-pyrrolidin-1-yl)-[2-(3-methyl-[1,2,4]oxadiazol-5-yl)-phenyl]-methanone (intermediate 15) | 426.2 |
| 153 | 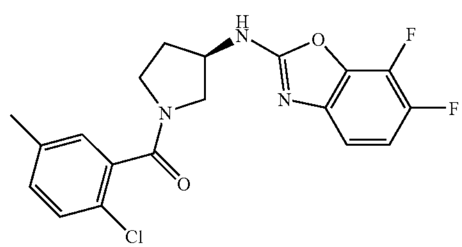 | 391.8 | (2-Chloro-5-methyl-phenyl)-[(R)-3-(6,7-difluoro-benzooxazol-2-ylamino)-pyrrolidin-1-yl]-methanone | (6,7-Difluoro-benzooxazol-2-yl)-(R)-pyrrolidin-3-yl-amine (intermediate 6) and ((R)-3-Amino-pyrrolidin-1-yl)-(2-chloro-5-methyl-phenyl)-methanone (intermediate 16) | 392.1 |
| 154 | 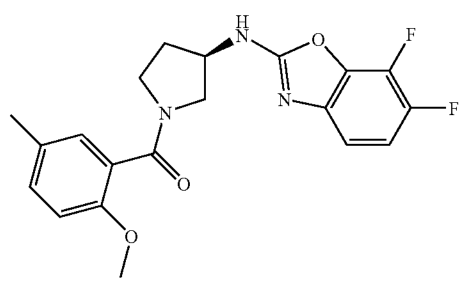 | 387.4 | [(R)-3-(6,7-Difluoro-benzooxazol-2-ylamino)-pyrrolidin-1-yl]-(2-methoxy-5-methyl-phenyl)-methanone | (6,7-Difluoro-benzooxazol-2-yl)-(R)-pyrrolidin-3-yl-amine (intermediate 6) and ((R)-3-Amino-pyrrolidin-1-yl)-(2-methoxy-5-methyl-phenyl)-methanone (intermediate 17) | 388.2 |
| 155 | 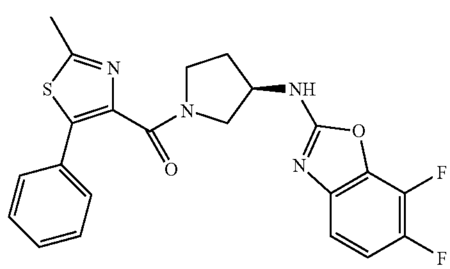 | 440.5 | [(R)-3-(6,7-Difluoro-benzooxazol-2-ylamino)-pyrrolidin-1-yl]-(2-methyl-5-phenyl-thiazol-4-yl)-methanone | (6,7-Difluoro-benzooxazol-2-yl)-(R)-pyrrolidin-3-yl-amine (intermediate 6) and ((R)-3-Amino-pyrrolidin-1-yl)-(2-methyl-5-phenyl-thiazol-4-yl)-methanone (intermediate 18) | 441.1 |
| 156 | 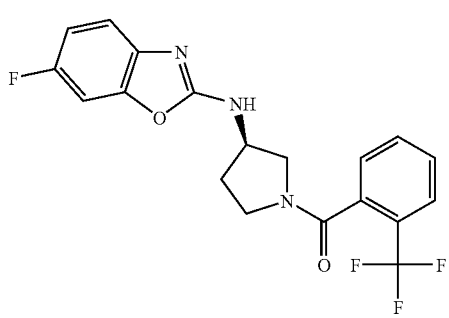 | 393.3 | [(R)-3-(6-Fluoro-benzooxazol-2-ylamino)-pyrrolidin-1-yl]-(2-trifluoromethyl-phenyl)-methanone | 2-Chloro-6-fluorobenzothiazole (Bioorganic & Medicinal Chemistry Letters 2007, 17, 4689) and ((R)-3-Amino-pyrrolidin-1-yl)-(2-trifluoromethyl-phenyl)-methanone (intermediate 10) | 394.1 |

-continued

| No. | structure | MW | name | starting materials | MW found (MH+) |
|---|---|---|---|---|---|
| 157 | 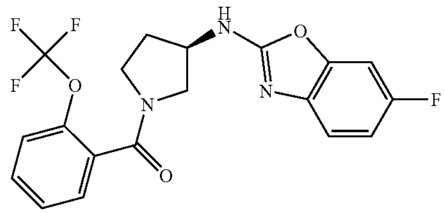 | 409.3 | [(R)-3-(6-Fluoro-benzooxazol-2-ylamino)-pyrrolidin-1-yl]-(2-trifluoromethoxy-phenyl)-methanone | 2-Chloro-6-fluorobenzothiazole (Bioorganic & Medicinal Chemistry Letters 2007, 17, 4689) and ((R)-3-Amino-pyrrolidin-1-yl)-(2-trifluoromethoxy-phenyl)-methanone (intermediate 11) | 410.1 |
| 158 | 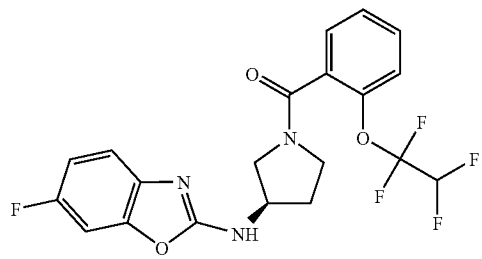 | 441.4 | [(R)-3-(6-Fluoro-benzooxazol-2-ylamino)-pyrrolidin-1-yl]-[2-(1,1,2,2-tetrafluoro-ethoxy)-phenyl]-methanone | 2-Chloro-6-fluorobenzothiazole (Bioorganic & Medicinal Chemistry Letters 2007, 17, 4689) and ((R)-3-Amino-pyrrolidin-1-yl)-]2-(1,1,2,2-tetrafluoro-ethoxy)-phenyl]-methanone (intermediate 12) | 442.1 |
| 159 | 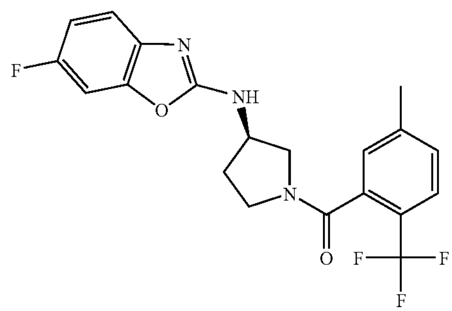 | 407.4 | [(R)-3-(6-Fluoro-benzooxazol-2-ylamino)-pyrrolidin-1-yl]-(5-methyl-2-trifluoromethyl-phenyl)-methanone | 2-Chloro-6-fluorobenzothiazole (Bioorganic & Medicinal Chemistry Letters 2007, 17, 4689) and ((R)-3-Amino-pyrrolidin-1-yl)-(5-methyl-2-trifluoromethyl-phenyl)-methanone (intermediate 13) | 408.2 |
| 160 | 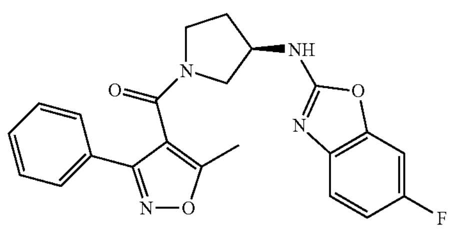 | 406.4 | [(R)-3-(6-Fluoro-benzooxazol-2-ylamino)-pyrrolidin-1-yl]-(5-methyl-3-phenyl-isoxazol-4-yl)-methanone | 2-Chloro-6-fluorobenzothiazole (Bioorganic & Medicinal Chemistry Letters 2007, 17, 4689) and ((R)-3-Amino-pyrrolidin-1-yl)-(5-methyl-3-phenyl-isoxazol-4-yl)-methanone (intermediate 14) | 407.2 |
| 161 | 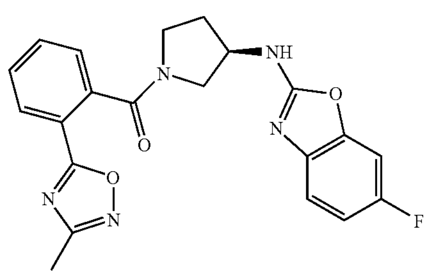 | 407.4 | [(R)-3-(6-Fluoro-benzooxazol-2-ylamino)-pyrrolidin-1-yl]-[2-(3-methyl-[1,2,4]oxadiazol-5-yl)-phenyl]-methanone | 2-Chloro-6-fluorobenzothiazole (Bioorganic & Medicinal Chemistry Letters 2007, 17, 4689) and ((R)-3-Amino-pyrrolidin-1-yl)-[2-(3-methyl-[1,2,4]oxadiazol-5-yl)-phenyl]-methanone (intermediate 15) | 408.2 |
| 162 | 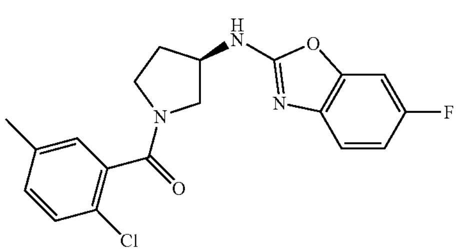 | 373.8 | (2-Chloro-5-methyl-phenyl)-[(R)-3-(6-fluoro-benzooxazol-2-ylamino)-pyrrolidin-1-yl]-methanone | 2-Chloro-6-fluorobenzothiazole (Bioorganic & Medicinal Chemistry Letters 2007, 17, 4689) and ((R)-3-Amino-pyrrolidin-1-yl)-(2-chloro-5-methyl-phenyl)-methanone (intermediate 16) | 374.1 |

-continued

| No. | structure | MW | name | starting materials | MW found (MH+) |
|---|---|---|---|---|---|
| 163 | 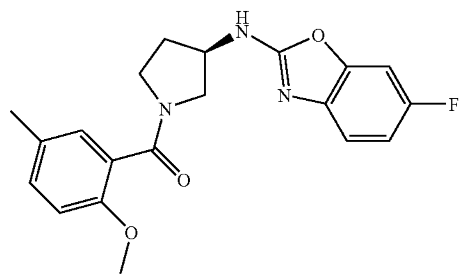 | 369.4 | [(R)-3-(6-Fluoro-benzooxazol-2-ylamino)-pyrrolidin-1-yl]-(2-methoxy-5-methyl-phenyl)-methanone | 2-Chloro-6-fluorobenzothiazole (Bioorganic & Medicinal Chemistry Letters 2007, 17, 4689) and ((R)-3-Amino-pyrrolidin-1-yl)-(2-methoxy-5-methyl-phenyl)-methanone (intermediate 17) | 370.2 |
| 164 | 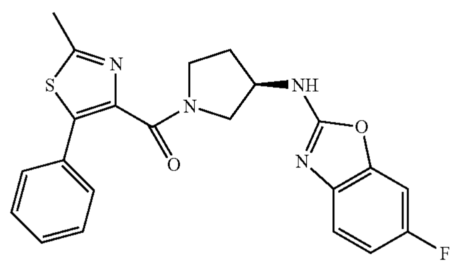 | 422.5 | [(R)-3-(6-Fluoro-benzooxazol-2-ylamino)-pyrrolidin-1-yl]-(2-methyl-5-phenyl-thiazol-4-yl)-methanone | 2-Chloro-6-fluorobenzothiazole (Bioorganic & Medicinal Chemistry Letters 2007, 17, 4689) and ((R)-3-Amino-pyrrolidin-1-yl)-(2-methyl-5-phenyl-thiazol-4-yl)-methanone (intermediate 18) | 423.1 |
| 165 | 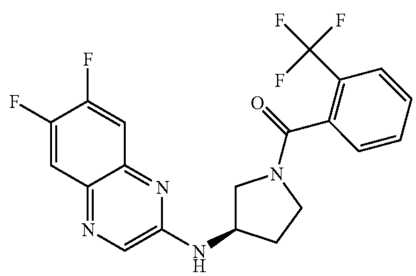 | 422.4 | [(R)-3-(6,7-Difluoro-quinoxalin-2-ylamino)-pyrrolidin-1-yl]-(2-trifluoromethyl-phenyl)-methanone | 2-Chloro-6,7-difluoroquinoxaline (WO2003051368) and ((R)-3-Amino-pyrrolidin-1-yl)-(2-trifluoromethyl-phenyl)-methanone (intermediate 10) | 423.2 |
| 166 | 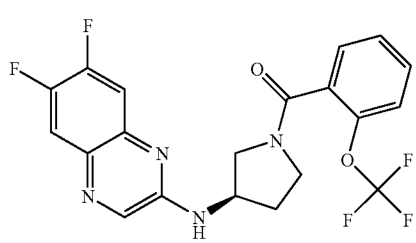 | 438.4 | [(R)-3-(6,7-Difluoro-quinoxalin-2-ylamino)-pyrrolidin-1-yl]-(2-trifluoromethoxy-phenyl)-methanone | 2-Chloro-6,7-difluoroquinoxaline (WO2003051368) and ((R)-3-Amino-pyrrolidin-1-yl)-(2-trifluoromethoxy-phenyl)-methanone (intermediate 11) | 439.2 |
| 167 | 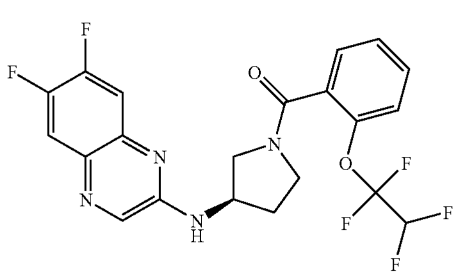 | 470.4 | [(R)-3-(6,7-Difluoro-quinoxalin-2-ylamino)-pyrrolidin-1-yl]-[2-(1,1,2,2-tetrafluoro-ethoxy)-phenyl]-methanone | 2-Chloro-6,7-difluoroquinoxaline (WO2003051368) and ((R)-3-Amino-pyrrolidin-1-yl)-[2-(1,1,2,2-tetrafluoro-ethoxy)-phenyl]-methanone (intermediate 12) | 471.3 |

| No. | structure | MW | name | starting materials | MW found (MH+) |
|---|---|---|---|---|---|
| 168 | 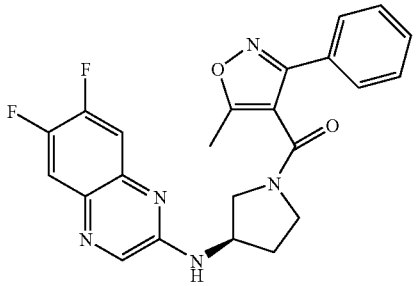 | 435.4 | [(R)-3-(6,7-Difluoro-quinoxalin-2-ylamino)-pyrrolidin-1-yl]-(5-methyl-3-phenyl-isoxazol-4-yl)-methanone | 2-Chloro-6,7-difluoroquinoxaline (WO2003051368) and ((R)-3-Amino-pyrrolidin-1-yl)-(5-methyl-3-phenyl-isoxazol-4-yl)-methanone (intermediate 14) | 436.2 |
| 169 | 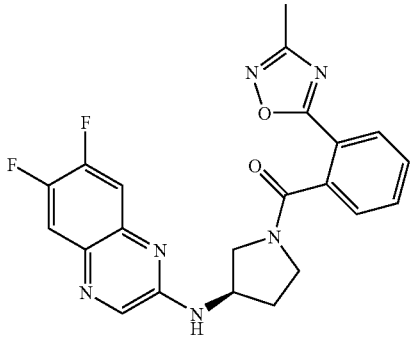 | 436.4 | [(R)-3-(6,7-Difluoro-quinoxalin-2-ylamino)-pyrrolidin-1-yl]-[2-(3-methyl-[1,2,4]oxadiazol-5-yl)-phenyl]-methanone | 2-Chloro-6,7-difluoroquinoxaline (WO2003051368) and ((R)-3-Amino-pyrrolidin-1-yl)-[2-(3-methyl-[1,2,4]oxadiazol-5-yl)-phenyl]-methanone (intermediate 15) | 437.2 |
| 170 | 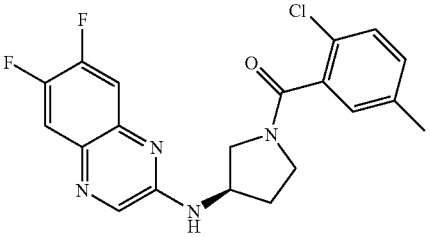 | 402.8 | (2-Chloro-5-methyl-phenyl)-[(R)-3-(6,7-difluoro-quinoxalin-2-ylamino)-pyrrolidin-1-yl]-methanone | 2-Chloro-6,7-difluoroquinoxaline (WO2003051368) and ((R)-3-Amino-pyrrolidin-1-yl)-(2-chloro-5-methyl-phenyl)-methanone (intermediate 16) | 403.2 |
| 171 | 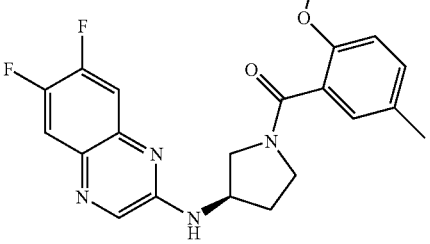 | 398.4 | [(R)-3-(6,7-Difluoro-quinoxalin-2-ylamino)-pyrrolidin-1-yl]-(2-methoxy-5-methyl-phenyl)-methanone | 2-Chloro-6,7-difluoroquinoxaline (WO2003051368) and ((R)-3-Amino-pyrrolidin-1-yl)-(2-methoxy-5-methyl-phenyl)-methanone (intermediate 17) | 399.2 |
| 172 | 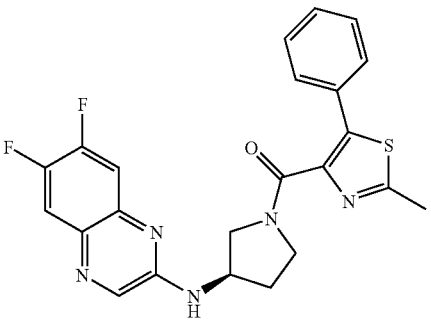 | 451.5 | [(R)-3-(6,7-Difluoro-quinoxalin-2-ylamino)-pyrrolidin-1-yl]-(2-methyl-5-phenyl-thiazol-4-yl)-methanone | 2-Chloro-6,7-difluoroquinoxaline (WO2003051368) and ((R)-3-Amino-pyrrolidin-1-yl)-(2-methyl-5-phenyl-thiazol-4-yl)-methanone (intermediate 18) | 452.2 |

| No. | structure | MW | name | starting materials | MW found (MH+) |
|---|---|---|---|---|---|
| 173 | 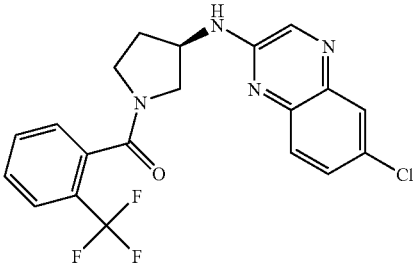 | 420.8 | [(R)-3-(6-Chloro-quinoxalin-2-ylamino)-pyrrolidin-1-yl]-(2-trifluoromethyl-phenyl)-methanone | 2,6-Dichloroquinoxaline (commercially available) and ((R)-3-Amino-pyrrolidin-1-yl)-(2-trifluoromethyl-phenyl)-methanone (intermediate 10) | 421.2 |
| 174 | 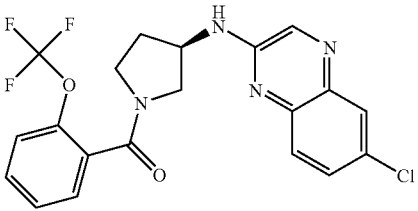 | 436.8 | [(R)-3-(6-Chloro-quinoxalin-2-ylamino)-pyrrolidin-1-yl]-(2-trifluoromethoxy-phenyl)-methanone | 2,6-Dichloroquinoxaline (commercially available) and ((R)-3-Amino-pyrrolidin-1-yl)-(2-trifluoromethoxy-phenyl)-methanone (intermediate 11) | 437.2 |
| 175 | 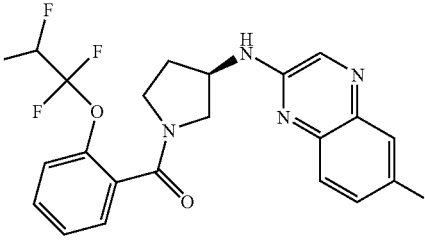 | 468.8 | [(R)-3-(6-Chloro-quinoxalin-2-ylamino)-pyrrolidin-1-yl]-[2-(1,1,2,2-tetrafluoro-ethoxy)-phenyl]-methanone | 2,6-Dichloroquinoxaline (commercially available) and ((R)-3-Amino-pyrrolidin-1-yl)-[2-(1,1,2,2-tetrafluoro-ethoxy)-phenyl]-methanone (intermediate 12) | 469.2 |
| 176 | 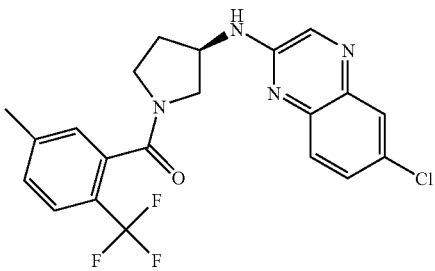 | 434.8 | [(R)-3-(6-Chloro-quinoxalin-2-ylamino)-pyrrolidin-1-yl]-(5-methyl-2-trifluoromethyl-phenyl)-methanone | 2,6-Dichloroquinoxaline (commercially available) and ((R)-3-Amino-pyrrolidin-1-yl)-(5-methyl-2-trifluoromethyl-phenyl)-methanone (intermediate 13) | 435.2 |
| 177 | 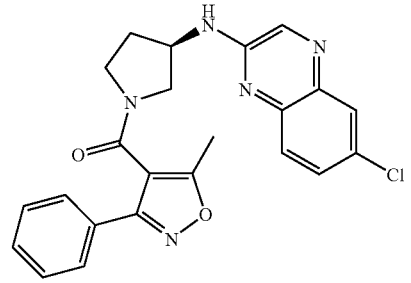 | 433.9 | [(R)-3-(6-Chloro-quinoxalin-2-ylamino)-pyrrolidin-1-yl]-(5-methyl-3-phenyl-isoxazol-4-yl)-methanone | 2,6-Dichloroquinoxaline (commercially available) and ((R)-3-Amino-pyrrolidin-1-yl)-(5-methyl-3-phenyl-isoxazol-4-yl)-methanone (intermediate 14) | 434.2 |

-continued

| No. | structure | MW | name | starting materials | MW found (MH+) |
|---|---|---|---|---|---|
| 178 | 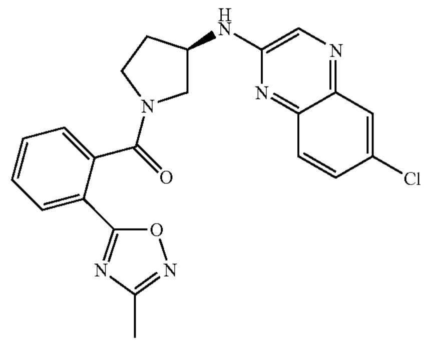 | 434.9 | [(R)-3-(6-Chloro-quinoxalin-2-ylamino)-pyrrolidin-1-yl]-[2-(3-methyl-[1,2,4]oxadiazol-5-yl)-phenyl]-methanone | 2,6-Dichloroquinoxaline (commercially available) and ((R)-3-Amino-pyrrolidin-1-yl)-[2-(3-methyl-[1,2,4]oxadiazol-5-yl)-phenyl]-methanone (intermediate 15) | 435.2 |
| 179 | 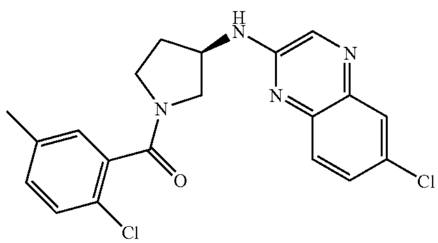 | 401.3 | (2-Chloro-5-methyl-phenyl)-[(R)-3-(6-chloro-quinoxalin-2-ylamino)-pyrrolidin-1-yl]-methanone | 2,6-Dichloroquinoxaline (commercially available) and ((R)-3-Amino-pyrrolidin-1-yl)-(2-chloro-5-methyl-phenyl)-methanone (intermediate 16) | 401.2 |
| 180 | 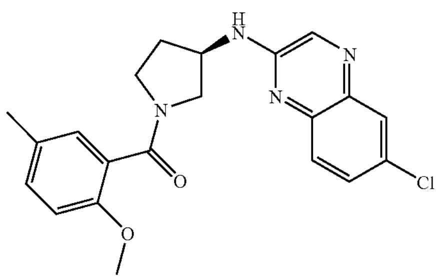 | 396.9 | [(R)-3-(6-Chloro-quinoxalin-2-ylamino)-pyrrolidin-1-yl]-(2-methoxy-5-methyl-phenyl)-methanone | 2,6-Dichloroquinoxaline (commercially available) and ((R)-3-Amino-pyrrolidin-1-yl)-(2-methoxy-5-methyl-phenyl)-methanone (intermediate 17) | 397.2 |
| 181 | 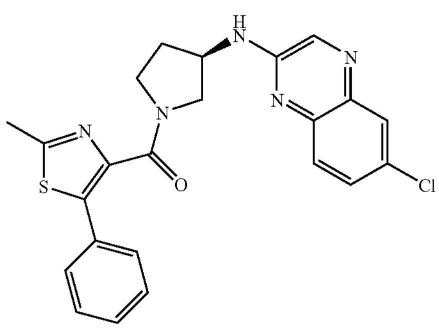 | 450.0 | [(R)-3-(6-Chloro-quinoxalin-2-ylamino)-pyrrolidin-1-yl]-(2-methyl-5-phenyl-thiazol-4-yl)-methanone | 2,6-Dichloroquinoxaline (commercially available) and ((R)-3-Amino-pyrrolidin-1-yl)-(2-methyl-5-phenyl-thiazol-4-yl)-methanone (intermediate 18) | 450.2 |
| 182 | 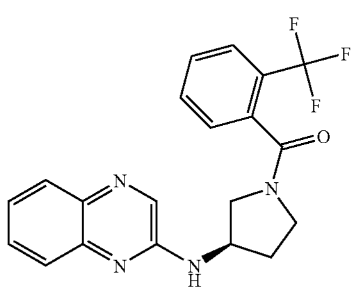 | 386.4 | [(R)-3-(Quinoxalin-2-ylamino)-pyrrolidin-1-yl]-(2-trifluoromethyl-phenyl)-methanone | 2-Chloroquinoxaline (commercially available) and ((R)-3-Amino-pyrrolidin-1-yl)-(2-trifluoromethyl-phenyl)-methanone (intermediate 10) | 387.2 |

-continued

| No. | structure | MW | name | starting materials | MW found (MH+) |
|---|---|---|---|---|---|
| 183 | 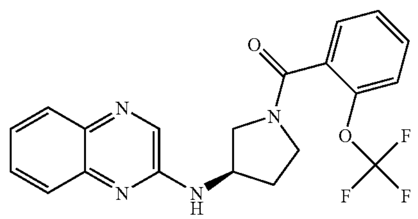 | 402.4 | [(R)-3-(Quinoxalin-2-ylamino)-pyrrolidin-1-yl]-(2-trifluoromethoxy-phenyl)-methanone | 2-Chloroquinoxaline (commercially available) and ((R)-3-Amino-pyrrolidin-1-yl)-(2-trifluoromethoxy-phenyl)-methanone (intermediate 11) | 403.2 |
| 184 | 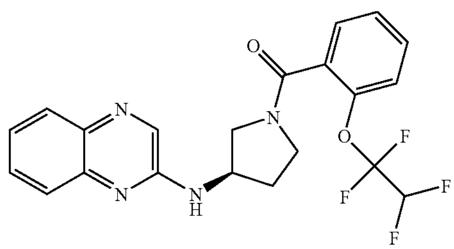 | 434.4 | [(R)-3-(Quinoxalin-2-ylamino)-pyrrolidin-1-yl]-[2-(1,1,2,2-tetrafluoro-ethoxy)-phenyl]-methanone | 2-Chloroquinoxaline (commercially available) and ((R)-3-Amino-pyrrolidin-1-yl)-[2-(1,1,2,2-tetrafluoro-ethoxy)-phenyl]-methanone (intermediate 12) | 435.2 |
| 185 | 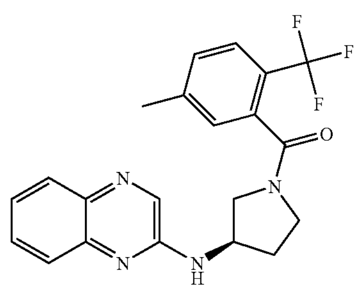 | 400.4 | (5-Methyl-2-trifluoromethyl-phenyl)-[(R)-3-(quinoxalin-2-ylamino)-pyrrolidin-1-yl]-methanone | 2-Chloroquinoxaline (commercially available) and ((R)-3-Amino-pyrrolidin-1-yl)-(5-methyl-2-trifluoromethyl-phenyl)-methanone (intermediate 13) | 401.2 |
| 186 | 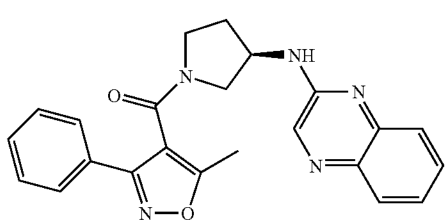 | 399.5 | (5-Methyl-3-phenyl-isoxazol-4-yl)-[(R)-3-(quinoxalin-2-ylamino)-pyrrolidin-1-yl]-methanone | 2-Chloroquinoxaline (commercially available) and ((R)-3-Amino-pyrrolidin-1-yl)-(5-methyl-3-phenyl-isoxazol-4-yl)-methanone (intermediate 14) | 400.3 |
| 187 | 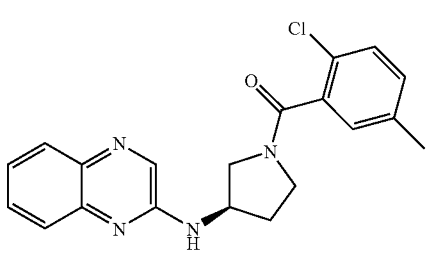 | 366.9 | (2-Chloro-5-methyl-phenyl)-[(R)-3-(quinoxalin-2-ylamino)-pyrrolidin-1-yl]-methanone | 2-Chloroquinoxaline (commercially available) and ((R)-3-Amino-pyrrolidin-1-yl)-(2-chloro-5-methyl-phenyl)-methanone (intermediate 16) | 367.2 |
| 188 | 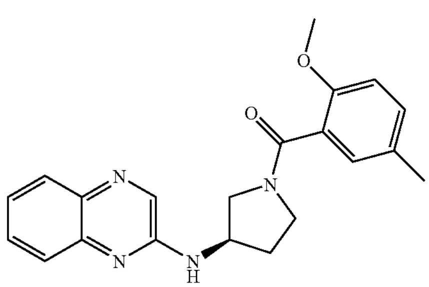 | 362.4 | (2-Methoxy-5-methyl-phenyl)-[(R)-3-(quinoxalin-2-ylamino)-pyrrolidin-1-yl]-methanone | 2-Chloroquinoxaline (commercially available) and ((R)-3-Amino-pyrrolidin-1-yl)-(2-methoxy-5-methyl-phenyl)-methanone (intermediate 17) | 363.2 |

| No. | structure | MW | name | starting materials | MW found (MH+) |
|---|---|---|---|---|---|
| 189 | 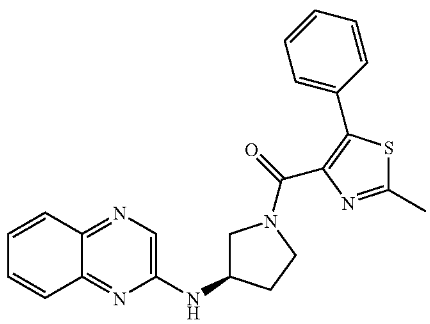 | 415.5 | (2-Methyl-5-phenyl-thiazol-4-yl)-[(R)-3-(quinoxalin-2-ylamino)-pyrrolidin-1-yl]-methanone | 2-Chloroquinoxaline (commercially available) and ((R)-3-Amino-pyrrolidin-1-yl)-(2-methyl-5-phenyl-thiazol-4-yl)-methanone (intermediate 18) | 416.2 |
| 190 | 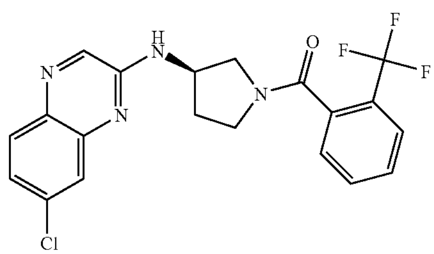 | 420.8 | [(R)-3-(7-Chloro-quinoxalin-2-ylamino)-pyrrolidin-1-yl]-(2-trifluoromethyl-phenyl)-methanone | 2,7-Dichloroquinoxaline (commercially available) and ((R)-3-Amino-pyrrolidin-1-yl)-(2-trifluoromethyl-phenyl)-methanone (intermediate 10) | 421.2 |
| 191 | 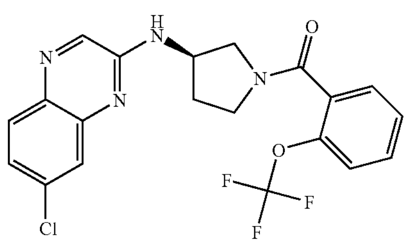 | 436.8 | [(R)-3-(7-Chloro-quinoxalin-2-ylamino)-pyrrolidin-1-yl]-(2-trifluoromethoxy-phenyl)-methanone | 2,7-Dichloroquinoxaline (commerically available) and ((R)-3-Amino-pyrrolidin-1-yl)-(2-trifluoromethoxy-phenyl)-methanone (intermediate 11) | 437.2 |
| 192 | 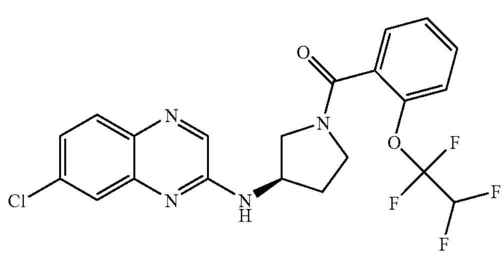 | 468.8 | [(R)-3-(7-Chloro-quinoxalin-2-ylamino)-pyrrolidin-1-yl]-[2-(1,1,2,2-tetrafluoro-ethoxy)-phenyl]-methanone | 2,7-Dichloroquinoxaline (commercially available) and ((R)-3-Amino-pyrrolidin-1-yl)-[2-(1,1,2,2-tetrafluoro-ethoxy)-phenyl]-methanone (intermediate 12) | 469.2 |
| 193 | 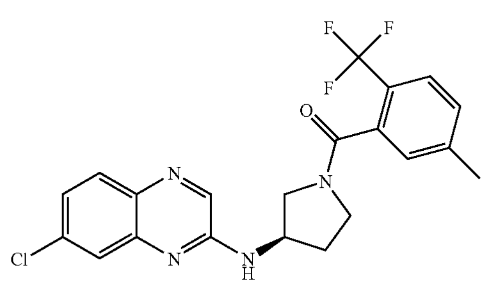 | 434.8 | [(R)-3-(7-Chloro-quinoxalin-2-ylamino)-pyrrolidin-1-yl]-(5-methyl-2-trifluoromethyl-phenyl)-methanone | 2,7-Dichloroquinoxaline (commercially available) and ((R)-3-Amino-pyrrolidin-1-yl)-(5-methyl-2-trifluoromethyl-phenyl)-methanone (intermediate 13) | 435.2 |

| No. | structure | MW | name | starting materials | MW found (MH+) |
|---|---|---|---|---|---|
| 194 | 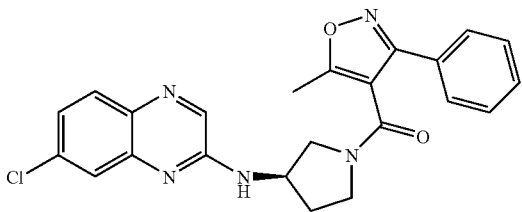 | 433.9 | [(R)-3-(7-Chloro-quinoxalin-2-ylamino)-pyrrolidin-1-yl]-(5-methyl-3-phenyl-isoxazol-4-yl)-methanone | 2,7-Dichloroquinoxaline (commercially available) and ((R)-3-Amino-pyrrolidin-1-yl)-(5-methyl-3-phenyl-isoxazol-4-yl)-methanone (intermediate 14) | 434.2 |
| 195 | 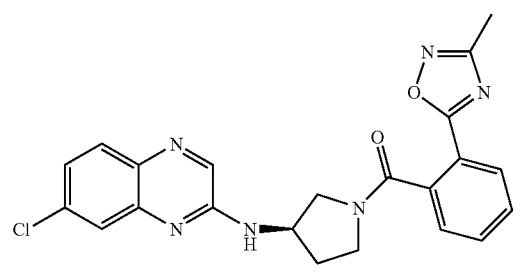 | 434.9 | [(R)-3-(7-Chloro-quinoxalin-2-ylamino)-pyrrolidin-1-yl]-[2-(3-methyl-[1,2,4]oxadiazol-5-yl)-phenyl]-mathanone | 2,7-Dichloroquinoxaline (commercially available) and ((R)-3-Amino-pyrrolidin-1-yl)-[2-(3-methyl-[1,2,4]oxadiazol-5-yl)-phenyl]-methanone (intermediate 15) | 435.2 |
| 196 | 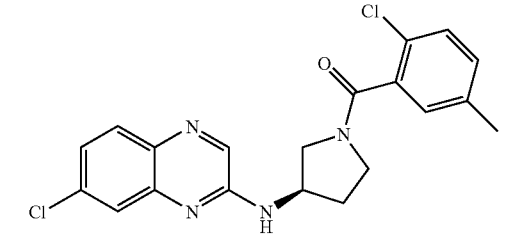 | 401.3 | (2-Chloro-5-methyl-phenyl)-[(R)-3-(7-chloro-quinoxalin-2-ylamino)-pyrrolidin-1-yl]-methanone | 2,7-Dichloroquinoxaline (commercially available) and ((R)-3-Amino-pyrrolidin-1-yl)-(2-chloro-5-methyl-phenyl)-methanone (intermediate 16) | 401.2 |
| 197 | 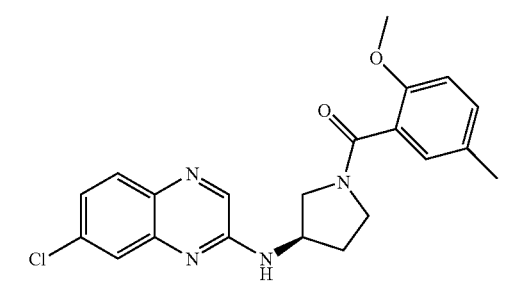 | 396.9 | [(R)-3-(7-Chloro-quinoxalin-2-ylamino)-pyrrolidin-1-yl]-(2-methoxy-5-methyl-phenyl)-methanone | 2,7-Dichloroquinoxaline (commercially available) and ((R)-3-Amino-pyrrolidin-1-yl)-(2-methoxy-5-methyl-phenyl)-methanone (intermediate 17) | 397.2 |
| 198 | 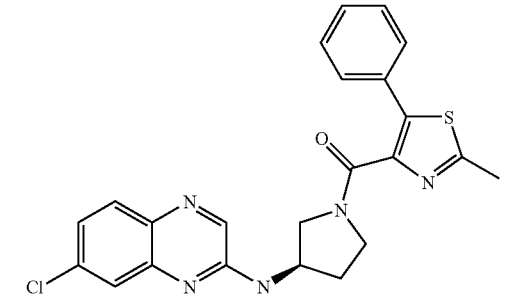 | 450.0 | [(R)-3-(7-Chloro-quinoxalin-2-ylamino)-pyrrolidin-1-yl]-(2-methyl-5-phenyl-thiazol-4-yl)-methanone | 2,7-Dichloroquinoxaline (commercially available) and ((R)-3-Amino-pyrrolidin-1-yl)-(2-methyl-5-phenyl-thiazol-4-yl)-methanone (intermediate 18) | 450.2 |

-continued

| No. | structure | MW | name | starting materials | MW found (MH+) |
|---|---|---|---|---|---|
| 199 | 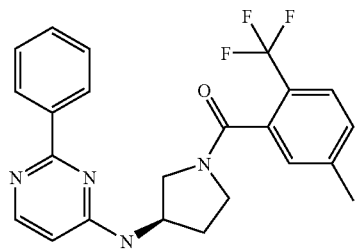 | 404.5 | (2,6-Dimethoxy-phenyl)-[(R)-3-(4-phenyl-pyrimidin-2-ylamino)-pyrrolidin-1-yl]-methanone | 2-Chloro-4-phenylpyrimidine (commercially available) and ((R)-3-Amino-pyrrolidin-1-yl)-(2,6-dimethoxy-phenyl)-methanone (intermediate 5) | 405.2 |

EXAMPLE 200

(5-Methyl-2-trifluoromethyl-phenyl)-[(R)-3-(2-phenyl-pyrimidin-4-ylamino)-pyrrolidin-1-yl]-methanone

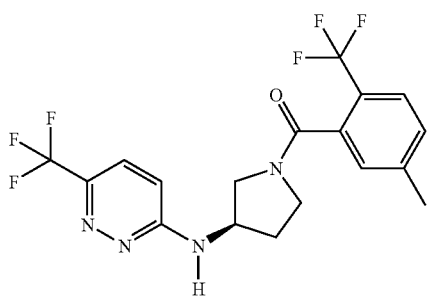

A solution of 30 mg (0.16 mmol) 4-chloro-2-phenyl-pyrimidine (CAS: 14790-42-2), 42.8 mg (0.16 mmol) ((R)-3-Amino-pyrrolidin-1-yl)-(5-methyl-2-trifluoromethyl-phenyl)-methanone (intermediate 13), 54.3 mg (0.39 mmol) $K_2CO_3$ and 6.5 mg (0.039 mmol) KI in 1 mL N,N-dimethylacetamide was heated in a 60° C. for 2 h, and at 100° C. for 23 h. The solvent was removed in vacuo. The residue was dissolved in ethyl acetate and washed twice with water. The organic layer was dried with $Na_2SO_4$ and filtered. The mixture was concentrated and purified with flash column chromatography on silica eluting with a gradient formed from n-heptane and ethyl acetate to provide 31 mg (46%) of the titled compound as a light yellow solid. MS(m/e): 427.2 (M+H+).

EXAMPLE 201

(5-Methyl-2-trifluoromethyl-phenyl)-[(R)-3-(6-trifluoromethyl-pyridazin-3-ylamino)-pyrrolidin-1-yl]-methanone

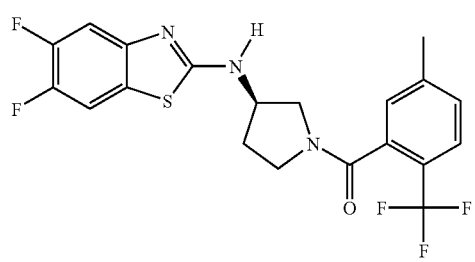

In analogy to the procedure described for example 200, the title compound was prepared from ((R)-3-Amino-pyrrolidin-1-yl)-(5-methyl-2-trifluoromethyl-phenyl)-methanone (intermediate 13) and 3-chloro-6-trifluoromethyl-pyridazine (commercially available). (MH+) 419.3.

EXAMPLE 202

[(R)-3-(5,6-Difluoro-benzothiazol-2-ylamino)-pyrrolidin-1-yl]-(5-methyl-2-trifluoromethyl-phenyl)-methanone

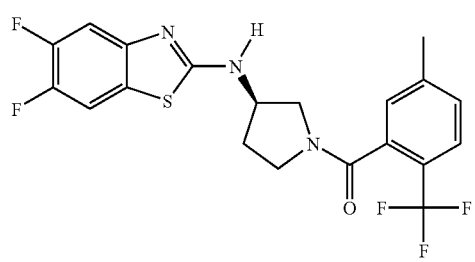

a) Step 1: 5,6-Difluoro-benzothiazole-2-thiol

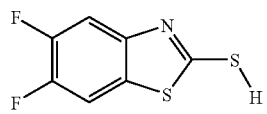

A mixture of 1 g (6.80 mmol) 2,4,5-trifluoroaniline and 1.33 g (8.16 mmol) potassium ethylxanthogenate in 5 mL dry N,N-dimethylformamide was heated in a 95° C. oil bath for 7 h. The reaction mixture was cooled to room temperature and diluted with water (15 mL). The mixture was acidified with aqueous HCl 2N. The precipitate was collected by filtration, washed with water and dried to provide 0.55 g (40%) of the titled compound as a light yellow solid. MS(m/e): 201.9 (M−H+).

b) Step 2: 5,6-Difluoro-2-methylsulfanyl-benzothiazole

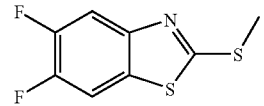

A suspension (0° C.) of 300 mg (1.476 mmol) 5,6-difluoro-benzothiazole-2-thiol and 306 mg (2.214 mmol) potassium carbonate in 6 mL N,N-dimethylformamide under nitrogen, were added 110.5 μL (1.77 mmol) iodomethane. The mixture was stirred at 0° C. for 1 h. The mixture was diluted with water (30 mL) and extracted with ethyl acetate. The combined extracts were washed with water and brine, dried over c) Step 3: rac-5,6-Difluoro-2-methanesulfinyl-benzothiazole

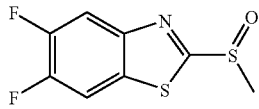

To a solution of 240 mg (1.1 mmol) 5,6-difluoro-2-methylsulfanyl-benzothiazole in 8 mL methanol under nitrogen at 0-5° C., was added drop wise a solution of 1.019 g (1.658 mmol) oxone in 4 mL water. The reaction mixture was stirred at 0° C. for 1 h. The suspension was diluted with water (10 mL). The solid was filtered, washed with water and dissolved in dichloromethane. The solution was dried over $Na_2SO_4$, filtered, concentrated in vacuo and purified with flash column chromatography on silica eluting with a gradient formed from n-heptane and ethyl acetate to provide 130 mg (50.6%) of the title compound as white solid. MS(m/e): 234.1 (M+H$^+$).

d) Step 4: [(R)-3-(5,6-Difluoro-benzothiazol-2-ylamino)-pyrrolidin-1-yl]-(5-methyl-2-trifluoromethyl-phenyl)-methanone A mixture of 30 mg (0.129 mmol) rac-5,6-difluoro-2-methanesulfinyl-benzothiazole and 70.3 mg (0.258 mmol) ((R)-3-Amino-pyrrolidin-1-yl)-(5-methyl-2-trifluoromethyl-phenyl)-methanone (intermediate 13) in 540 μL dimethyl sulfoxide was heated in a 100° C. oil-bath for 4 h. The solution was cooled to room temperature, diluted with water and basified with a saturated $NaHCO_3$ solution. The mixture was stirred for 1 h. The solid was filtered, washed with water and dissolved in dichloromethane. The solution was dried over $Na_2SO_4$, filtered and concentrated in vacuo. The crude compound was purified with flash column chromatography on silica eluting with a gradient formed from n-heptane and ethyl acetate to provide 27 mg (47.6%) of the title compound as a white solid. MS(m/e): 442.2 (M+H$^+$).

EXAMPLE 203

(R)-3-(4-Chloro-benzothiazol-2-ylamino)-pyrrolidin-1-yl]-(5-methyl-2-trifluoromethyl-phenyl)-methanone

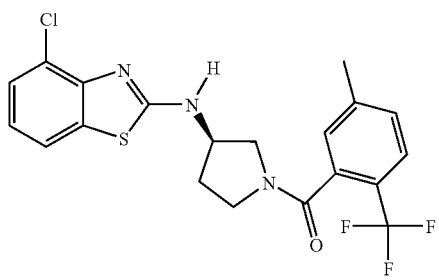

Step 1: rac-4-chloro-2-methanesulfinyl-benzothiazole

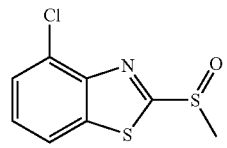

In analogy to the procedure described for example 202, step 1-3, the title compound was prepared from 2-amino-3-chloro-benzenethiol. (M+H$^+$) 232.1.

Step 2: (R)-3-(4-Chloro-benzothiazol-2-ylamino)-pyrrolidin-1-yl]-(5-methyl-2-trifluoromethyl-phenyl)-methanone In analogy to the procedure described for example 202, step 4, the title compound was prepared from rac-4-chloro-2-methanesulfinyl-benzothiazole and ((R)-3-Amino-pyrrolidin-1-yl)-(5-methyl-2-trifluoromethyl-phenyl)-methanone (intermediate 13). (M+H$^+$) 440.2.

EXAMPLE 204

(R)-3-(6-tert-Butyl-quinoxalin-2-ylamino)-pyrrolidin-1-yl]-(5-methyl-2-trifluoromethyl-phenyl)-methanone

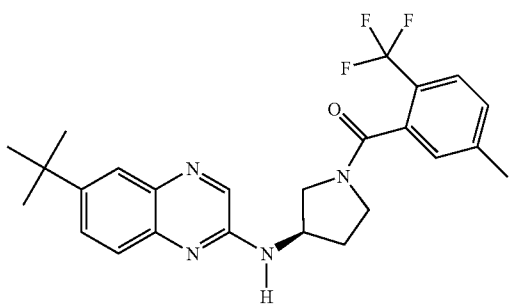

Step 1: 6-tert-Butyl-quinoxalin-2-ol

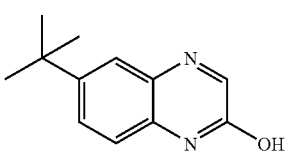

To a solution of 2 g (12.18 mmol) 4-tert-butyl-1,2-diaminobenzene in 20 mL ethanol under argon at room temperature, was added 3.139 mL (15.83 mmol) ethyl glyoxalate (50% in toluene). The reaction mixture was stirred at room temperature for 4 h. The resulting suspension was filtered and washed with ethanol. The powder was dried to provide 257 mg (10.4%) of the title compound as a white solid. MS(m/e): 201.0 (M−H).

Step 2: 6-tert-Butyl-2-chloro-quinoxaline

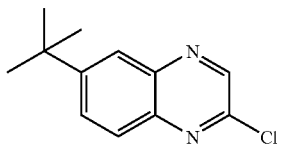

A solution of 250 mg (1.236 mmol) of 6-tert-Butyl-quinoxalin-2-ol in 1.07 mL (11.43 mmol) phosphorus oxychloride under nitrogen was heated at 110° C. for 3 h. The solution was cooled to room temperature and added drop wise to water (10-15° C.). Ethyl acetate was added. The aqueous layer was extracted with ethylacetate. The combined organic phases were washed with water, dried over $Na_2SO_4$ and concentrated. The crude compound was purified with flash column chromatography on silica eluting with a gradient formed from n-heptane and ethyl acetate to provide 219 mg (80.3%) of the title compound as a green solid. MS(m/e): 220 (M+H$^+$).

Step 3: (R)-3-(6-tert-Butyl-quinoxalin-2-ylamino)-pyrrolidin-1-yl]-(5-methyl-2-trifluoromethyl-phenyl)-methanone In analogy to the procedure described for example 200, the title compound was prepared from ((R)-3-Amino-pyrrolidin-1-yl)-(5-methyl-2-trifluoromethyl-phenyl)-methanone (intermediate 13) and 6-tert-Butyl-2-chloro-quinoxaline. (MH$^+$) 457.3.

EXAMPLE 205

(R)-3-(8-Chloro-6-trifluoromethyl-quinoxalin-2-ylamino)-pyrrolidin-1-yl]-(5-methyl-2-trifluoromethyl-phenyl)-methanone

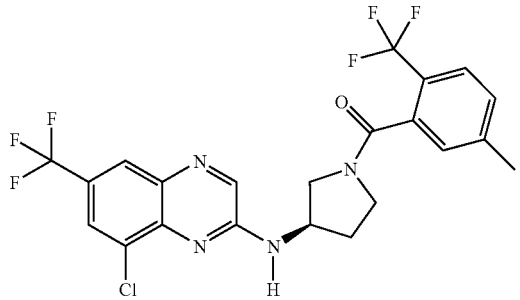

Step 1: 2,8-dichloro-6-trifluoromethyl-quinoxaline

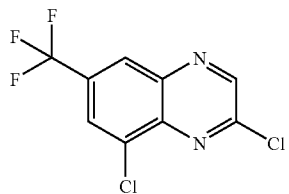

In analogy to the procedure described for example 204, step 1-2, the title compound was prepared from 3-chloro-5-trifluoromethyl-benzene-1,2-diamine. (M$^+$) 266.

Step 2: (R)-3-(8-Chloro-6-trifluoromethyl-quinoxalin-2-ylamino)-pyrrolidin-1-yl]-(5-methyl-2-trifluoromethyl-phenyl)-methanone In analogy to the procedure described for example 200, the title compound was prepared from 2,8-dichloro-6-trifluoromethyl-quinoxaline and ((R)-3-Amino-pyrrolidin-1-yl)-(5-methyl-2-trifluoromethyl-phenyl)-methanone. (M–H$^+$) 501.1.

EXAMPLE 206

(R)-3-(7-Methoxy-quinoxalin-2-ylamino)-pyrrolidin-1-yl]-(5-methyl-2-trifluoromethyl-phenyl)-methanone

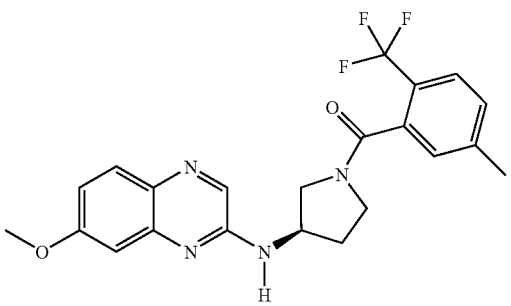

Step 1: 2-Chloro-7-methoxy-quinoxaline

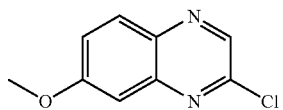

In analogy to the procedure described for example 204, step 1-2, the title compound was prepared from 4-methoxy-benzene-1,2-diamine. (M+H$^+$) 195.2.

Step 2: (R)-3-(7-Methoxy-quinoxalin-2-ylamino)-pyrrolidin-1-yl]-(5-methyl-2-trifluoromethyl-phenyl)-methanone In analogy to the procedure described for example 200, the title compound was prepared from 2-chloro-7-methoxy-quinoxaline and ((R)-3-amino-pyrrolidin-1-yl)-(5-methyl-2-trifluoromethyl-phenyl)-methanone (intermediate 13). (M–H$^+$) 431.3.

EXAMPLE 207

(R)-3-(6-Fluoro-quinoxalin-2-ylamino)-pyrrolidin-1-yl]-(5-methyl-2-trifluoromethyl-phenyl)-methanone

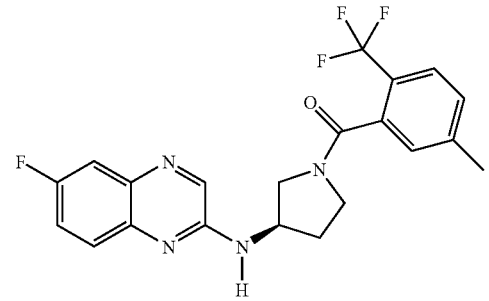

Step 1: 2-Chloro-6-fluoro-quinoxaline

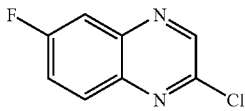

In analogy to the procedure described for example 204, step 1-2, the title compound was prepared from 4-fluoro-benzene-1,2-diamine. (M+H$^+$) 182.0.

Step 2: (R)-3-(6-Fluoro-quinoxalin-2-ylamino)-pyrrolidin-1-yl]-(5-methyl-2-trifluoromethyl-phenyl)-methanone In analogy to the procedure described for example 200, the title compound was prepared from 2-chloro-6-fluoro-quinoxaline and ((R)-3-amino-pyrrolidin-1-yl)-(5-methyl-2-trifluoromethyl-phenyl)-methanone (intermediate 13), (M–H$^+$) 419.3.

EXAMPLE 208

(R)-3-(5-Fluoro-6-trifluoromethyl-benzothiazol-2-ylamino)-pyrrolidin-1-yl]-(5-methyl-2-trifluoromethyl-phenyl)-methanone

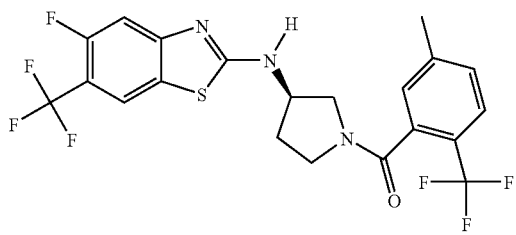

Step 1: rac-5-Fluoro-2-methanesulfinyl-6-trifluoromethyl-benzothiazole

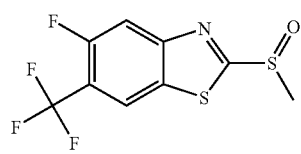

In analogy to the procedure described for example 202, step 1-3, the title compound was prepared from 2-amino-4-fluoro-5-trifluoromethyl-benzenethiol. (M+H$^+$) 284.0.

Step 2: (R)-3-(5-Fluoro-6-trifluoromethyl-benzothiazol-2-ylamino)-pyrrolidin-1-yl]-(5-methyl-2-trifluoromethyl-phenyl)-methanone In analogy to the procedure described for example 202, step 4, the title compound was prepared from rac-5-fluoro-2-methanesulfinyl-6-trifluoromethyl-benzothiazole and ((R)-3-amino-pyrrolidin-1-yl)-(5-methyl-2-trifluoromethyl-phenyl)-methanone (intermediate 13). (M+H$^+$) 492.2.

EXAMPLE 209

(R)-3-(6,7-Dichloro-quinoxalin-2-ylamino)-pyrrolidin-1-yl]-(5-methyl-2 trifluoromethyl-phenyl)-methanone

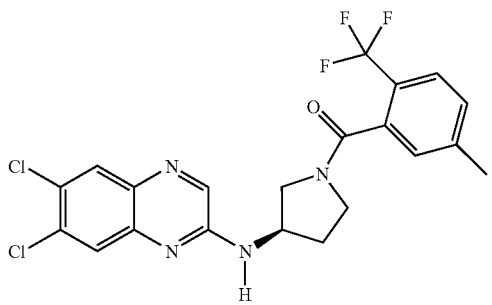

Step 1: 2,6,7-Trichloro-quinoxaline

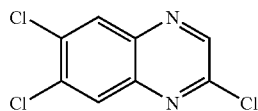

In analogy to the procedure described for example 204, step 1-2, the title compound was prepared from 4,5-dichloro-benzene-1,2-diamine. (M+H$^+$) 182.0

Step 2: (R)-3-(6,7-Dichloro-quinoxalin-2-ylamino)-pyrrolidin-1-yl]-(5-methyl-2 trifluoromethyl-phenyl)-methanone In analogy to the procedure described for example 200, the title compound was prepared from 2,6,7-trichloro-quinoxaline and ((R)-3-amino-pyrrolidin-1-yl)-(5-methyl-2-trifluoromethyl-phenyl)-methanone (intermediate 13). (M–H$^+$) 469.2.

EXAMPLE 210

(5-Methyl-2-trifluoromethyl-phenyl)-(R)-3-(6-trifluoromethyl-quinoxalin-2-ylamino)-pyrrolidin-1-yl]-methanone

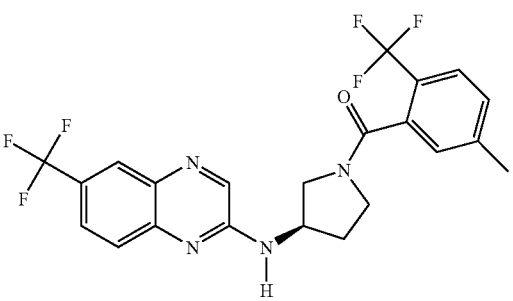

Step 1: 2-Chloro-6-trifluoromethyl-quinoxaline

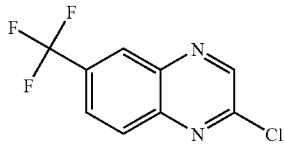

In analogy to the procedure described for example 204, step 1-2, the title compound was prepared from 4-trifluoromethyl-benzene-1,2-diamine. (M+H$^+$) 232.

Step 2: (5-Methyl-2-trifluoromethyl-phenyl)-[(R)-3-(6-trifluoromethyl-quinoxalin-2-ylamino)-pyrrolidin-1-yl]-methanone In analogy to the procedure described for example 200, the title compound was prepared from 2-chloro-6-trifluoromethyl-quinoxaline and ((R)-3-amino-pyrrolidin-1-yl)-(5-methyl-2-trifluoromethyl-phenyl)-methanone (intermediate 13). (M+H$^+$) 469.2.

EXAMPLE 211

(5-Methyl-2-trifluoromethyl-phenyl)-(R)-3-(7-trifluoromethyl-quinoxalin-2-ylamino)-pyrrolidin-1-yl]-methanone

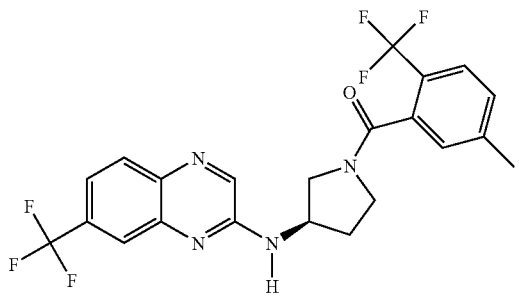

Step 1: 2-Chloro-7-trifluoromethyl-quinoxaline

In analogy to the procedure described for example 204, step 1-2, the title compound was prepared from 4-trifluoromethyl-benzene-1,2-diamine. (M+H$^+$) 232.

Step 2: (5-Methyl-2-trifluoromethyl-phenyl)-[(R)-3-(7-trifluoromethyl-quinoxalin-2-ylamino)-pyrrolidin-1-yl]-methanone In analogy to the procedure described for example 200, the title compound was prepared from 2-chloro-7-trifluoromethyl-quinoxaline and ((R)-3-amino-pyrrolidin-1-yl)-(5-methyl-2-trifluoromethyl-phenyl)-methanone (intermediate 13). (M+H$^+$) 469.2.

EXAMPLE 212

(R)-3-(7-Chloro-6-methyl-quinoxalin-2-ylamino)-pyrrolidin-1-yl]-(5-methyl-2-trifluoromethyl-phenyl)-methanone

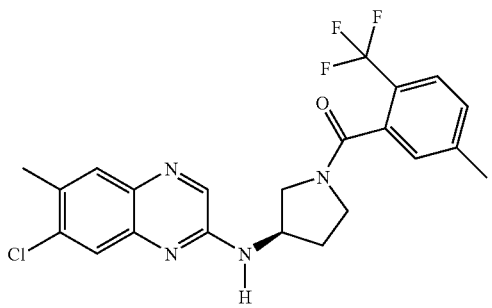

Step 1: 2,7-Dichloro-6-methyl-quinoxaline

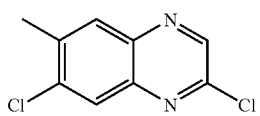

In analogy to the procedure described for example 204, step 1-2, the title compound was prepared from 4-chloro-5-methyl-benzene-1,2-diamine. (M–H$^+$) 212.

Step 2: (R)-3-(7-Chloro-6-methyl-quinoxalin-2-ylamino)-pyrrolidin-1-yl]-(5-methyl-2-trifluoromethyl-phenyl)-methanone In analogy to the procedure described for example 200, the title compound was prepared from 2,7-dichloro-6-methyl-quinoxaline and ((R)-3-amino-pyrrolidin-1-yl)-(5-methyl-2-trifluoromethyl-phenyl)-methanone (intermediate 13). (M+H$^+$) 449.2.

EXAMPLE 213

(R)-3-(6-Chloro-7-methyl-quinoxalin-2-ylamino)-pyrrolidin-1-yl]-(5-methyl-2-trifluoromethyl-phenyl)-methanone

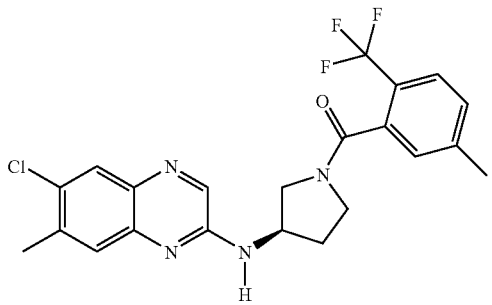

Step 1: 2,6-Dichloro-7-methyl-quinoxaline

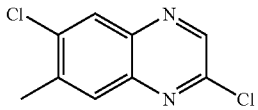

In analogy to the procedure described for example 204, step 1-2, the title compound was prepared from 4-chloro-5-methyl-benzene-1,2-diamine. (M−H⁺) 212.

Step 2: (R)-3-(6-Chloro-7-methyl-quinoxalin-2-ylamino)-pyrrolidin-1-yl]-(5-methyl-2-trifluoromethyl-phenyl)-methanone In analogy to the procedure described for example 200, the title compound was prepared from 2,6-dichloro-7-methyl-quinoxaline and ((R)-3-amino-pyrrolidin-1-yl)-(5-methyl-2-trifluoromethyl-phenyl)-methanone (intermediate 13). (M+H⁺) 449.2.

EXAMPLE 214

(R)-3-(6-Chloro-benzothiazol-2-ylamino)-pyrrolidin-1-yl]-(5-methyl-2-trifluoromethyl-phenyl)-methanone

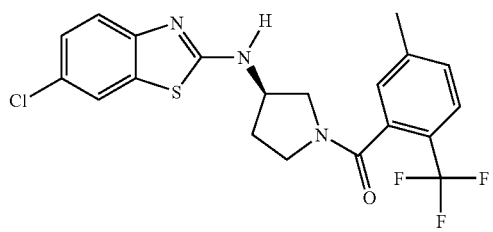

Step 1: rac-6-Chloro-2-methanesulfinyl-benzothiazole

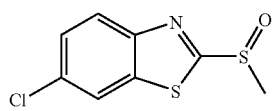

In analogy to the procedure described for example 202, step 1-3, the title compound was prepared from 2-amino-5-chloro-benzenethiol. (M+H⁺) 232.1.

Step 2: (R)-3-(6-Chloro-benzothiazol-2-ylamino)-pyrrolidin-1-yl]-(5-methyl-2-trifluoromethyl-phenyl)-methanone In analogy to the procedure described for example 202, step 4, the title compound was prepared from rac-6-chloro-2-methanesulfinyl-benzothiazole and ((R)-3-amino-pyrrolidin-1-yl)-(5-methyl-2-trifluoromethyl-phenyl)-methanone (intermediate 13). (M+H⁺) 440.2.

EXAMPLE 215

(R)-3-(5,6-Dimethyl-quinoxalin-2-ylamino)-pyrrolidin-1-yl]-(5-methyl-2-trifluoromethyl-phenyl)-methanone

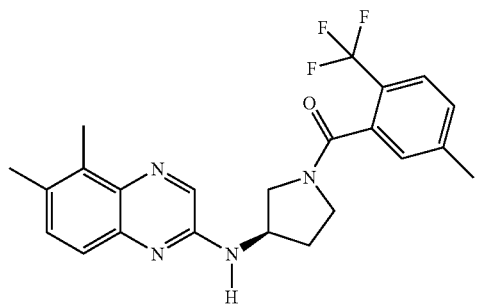

Step 1: 2-Chloro-5,6-dimethyl-quinoxaline

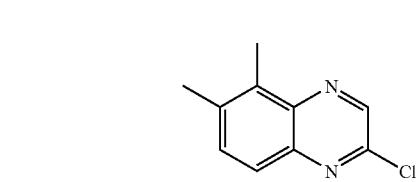

In analogy to the procedure described for example 204, step 1-2, the title compound was prepared from 3,4-dimethyl-benzene-1,2-diamine. (M+H⁺) 193.

Step 2: (R)-3-(5,6-Dimethyl-quinoxalin-2-ylamino)-pyrrolidin-1-yl]-(5-methyl-2-trifluoromethyl-phenyl)-methanone In analogy to the procedure described for example 200, the title compound was prepared from 2-chloro-5,6-dimethyl-quinoxaline and ((R)-3-amino-pyrrolidin-1-yl)-(5-methyl-2-trifluoromethyl-phenyl)-methanone (intermediate 13). (M+H⁺) 429.3.

EXAMPLE 216

(R)-3-(7,8-Dimethyl-quinoxalin-2-ylamino)-pyrrolidin-1-yl]-(5-methyl-2-trifluoromethyl-phenyl)-methanone

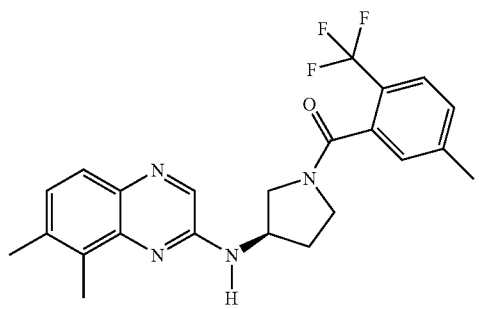

Step 1: 2-Chloro-7,8-dimethyl-quinoxaline

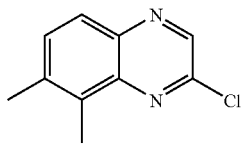

In analogy to the procedure described for example 204, step 1-2, the title compound was prepared from 3,4-dimethyl-benzene-1,2-diamine. (M+H⁺) 193.

Step 2: (R)-3-(7,8-Dimethyl-quinoxalin-2-ylamino)-pyrrolidin-1-yl]-(5-methyl-2-trifluoromethyl-phenyl)-methanone In analogy to the procedure described for example 200, the title compound was prepared from 2-chloro-7,8-dimethyl-quinoxaline and ((R)-3-amino-pyrrolidin-1-yl)-(5-methyl-2-trifluoromethyl-phenyl)-methanone (intermediate 13). (M+H⁺) 429.3.

EXAMPLE 217

(2,6-Dimethoxy-phenyl)-(R)-3-(5-trifluoromethyl-benzothiazol-2-ylamino)-pyrrolidin-1-yl]-methanone

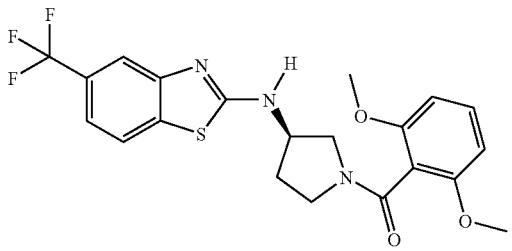

Step 1: 2-Methylsulfanyl-5-trifluoromethyl-benzothiazole

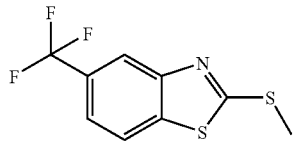

In analogy to the procedure described for example 202, step 1-2, the title compound was prepared from 2-amino-4-trifluoromethyl-benzenethiol, (M+H⁺) 250.1.

Step 2: 2-Methanesulfonyl-5-trifluoromethyl-benzothiazole

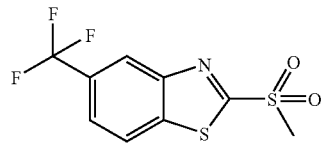

In analogy to the procedure described for example 202, step 3, the title compound was prepared from 2-methylsulfanyl-5-trifluoromethyl-benzothiazole. (M+H⁺) 282.0.

Step 3: (2,6-Dimethoxy-phenyl)-[(R)-3-(5-trifluoromethyl-benzothiazol-2-ylamino)-pyrrolidin-1-yl]-methanone In analogy to the procedure described for example 202, step 4, the title compound was prepared from 2-methanesulfonyl-5-trifluoromethyl-benzothiazole and ((R)-3-Amino-pyrrolidin-1-yl)-(2,6-dimethoxy-phenyl)-methanone (Intermediate 5). (M+H⁺) 452.2.

EXAMPLE 218

(R)-3-(5,7-Difluoro-benzothiazol-2-ylamino)-pyrrolidin-1-yl]-(5-phenyl-isoxazol-4-yl)-methanone

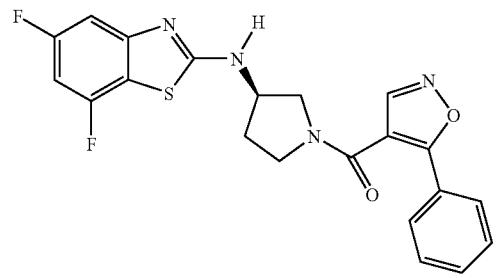

Step 1: 5,7-Difluoro-benzothiazole-2-thiol

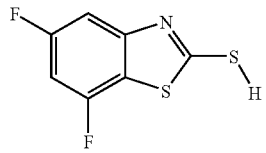

In analogy to the procedure described for example 202, step 1, the title compound was prepared from 2-amino-4,6-difluoro-benzenethiol. (M−H⁺) 201.9.

Step 2: 2-Chloro-5,7-difluoro-benzothiazole

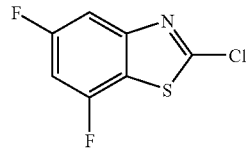

To a suspension of 2 g (9.841 mmol) 5,7-difluoro-benzothiazole-2-thiol in 10.7 mL (147.6 mmol) thionyl chloride was added drop wise 215 □L N,N-dimethylformamide at room temperature. The mixture was stirred at room temperature for 2 days. The solvent was removed in vacuo. The crude compound was purified with flash column chromatography on silica eluting with a gradient formed from n-heptane and ethyl acetate to provide 659 mg (32.6%) of the title compound as an off-white solid. MS(m/e): 205 (M+H⁺).

Step 3: (R)-3-(5,7-Difluoro-benzothiazol-2-ylamino)-pyrrolidin-1-yl]-(5-phenyl-isoxazol-4-yl)-methanone To a solution of 30 mg (0.146 mmol) 2-chloro-5,7-difluoro-benzothiazole and 45 mg (0.175 mmol) ((R)-3-Aminopyrrolidin-1-yl)-(5-phenyl-isoxazol-4-yl)-methanone (intermediate 19) in 0.5 mL DMF were added 50 μL (0.292 mmol) N-ethyldiisopropylamine. The mixture was heated in a 90° C. oil-bath for 20 minutes. The solvent was removed under reduced pressure. The crude gum was purified with flash column chromatography on silica eluting with a gradient formed from n-heptane and ethyl acetate to provide 13.2 mg (21%) of the title compound as a light yellow solid. MS(m/e): 427.1 (M+H⁺).

EXAMPLE 219

(R)-3-(5-Chloro-benzothiazol-2-ylamino)-pyrrolidin-1-yl]-(2,6-dimethoxy-phenyl)-methanone

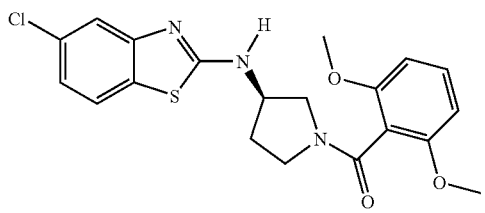

Step 1:
rac-5-Chloro-2-methanesulfinyl-benzothiazole

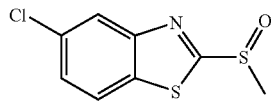

In analogy to the procedure described for example 202, step 1-3, the title compound was prepared from 2-amino-4-chloro-benzenethiol. (M+H⁺) 232.1.

Step 2: (R)-3-(5-Fluoro-6-trifluoromethyl-benzothiazol-2-ylamino)-pyrrolidin-1-yl]-(5-methyl-2-trifluoromethyl-phenyl)-methanone In analogy to the procedure described for example 202, step 4, the title compound was prepared from rac-5-chloro-2-methanesulfinyl-benzothiazole and ((R)-3-amino-pyrrolidin-1-yl)-(2,6-dimethoxy-phenyl)-methanone (Intermediate 5). (M+H⁺) 418.3.

EXAMPLE 220

(R)-3-(6,7-Difluoro-quinoxalin-2-ylamino)-pyrrolidin-1-yl]-(5-methyl-2-trifluoromethyl-phenyl)-methanone

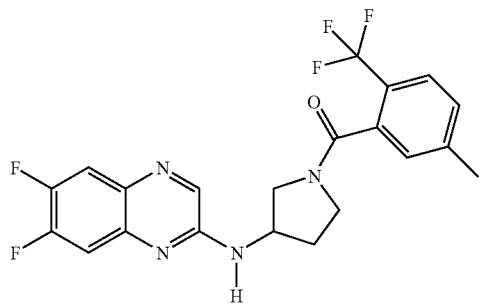

Step 1: 2-Chloro-6,7-difluoro-quinoxaline

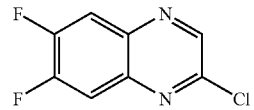

In analogy to the procedure described for example 204, step 1-2, the title compound was prepared from 4,5-difluoro-benzene-1,2-diamine. (M+H⁺) 200.

Step 2: (R)-3-(5,6-Dimethyl-quinoxalin-2-ylamino)-pyrrolidin-1-yl]-(5-methyl-2-trifluoromethyl-phenyl)-methanone In analogy to the procedure described for example 200, the title compound was prepared from 2-chloro-6,7-difluoro-quinoxaline and ((R)-3-amino-pyrrolidin-1-yl)-(5-methyl-2-trifluoromethyl-phenyl)-methanone (intermediate 13). (M+H⁺) 437.3.

EXAMPLE 221

(R)-3-(7-Chloro-benzothiazol-2-ylamino)-pyrrolidin-1-yl]-(5-methyl-2-trifluoromethyl-phenyl)-methanone

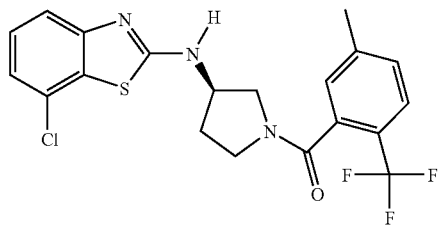

Step 1:
rac-7-Chloro-2-methanesulfinyl-benzothiazole

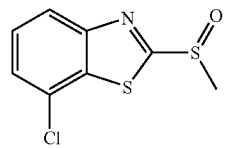

In analogy to the procedure described for example 202, step 1-3, the title compound was prepared from 2-amino-6-chloro-benzenethiol. (M+H⁺) 232.1.

Step 2: (R)-3-(7-Chloro-benzothiazol-2-ylamino)-pyrrolidin-1-yl]-(5-methyl-2-trifluoromethyl-phenyl)-methanone In analogy to the procedure described for example 202, step 4, the title compound was prepared from rac-7-chloro-2-methanesulfinyl-benzothiazole and ((R)-3-amino-pyrrolidin-1-yl)-(5-methyl-2-trifluoromethyl-phenyl)-methanone (intermediate 13). (M−H⁺) 438.1.

EXAMPLE 222

(R)-3-(4,6-Difluoro-benzothiazol-2-ylamino)-pyrrolidin-1-yl]-(5-phenyl-isoxazol-4-yl)-methanone

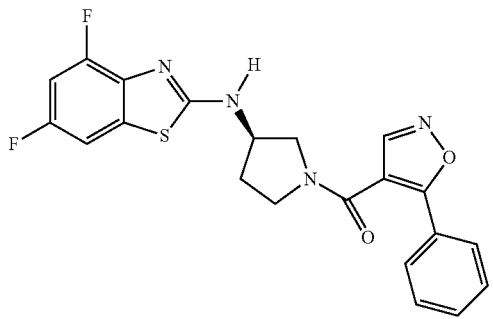

In analogy to the procedure described for example 217, step 3, the title compound was prepared from 2-chloro-4,6-difluoro-benzothiazole (commercially available) and ((R)-3-Amino-pyrrolidin-1-yl)-(5-phenyl-isoxazol-4-yl)-methanone (intermediate 19), (M−H⁺) 427.1.

EXAMPLE 223

(R)-3-(5-Chloro-benzothiazol-2-ylamino)-pyrrolidin-1-yl]-(5-methyl-2-trifluoromethyl-phenyl)-methanone

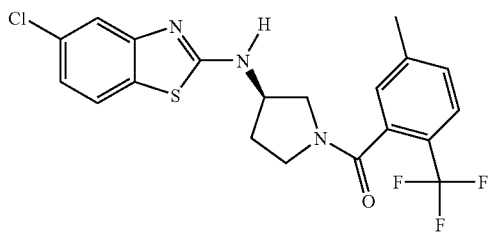

In analogy to the procedure described for example 202, step 4, the title compound was prepared from 5-chloro-2-methanesulfinyl-benzothiazole (example 219, step 1) and ((R)-3-amino-pyrrolidin-1-yl)-(5-methyl-2-trifluoromethyl-phenyl)-methanone (intermediate 13). (M+H⁺) 440.2.

The invention claimed is:
1. A compound of formula I

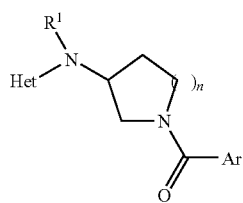

wherein
Ar is an unsubstituted or substituted aryl or heteroaryl group, wherein the substituted aryl and heteroaryl groups are substituted by one or more substituents $R^2$;

$R^2$ is hydroxy, halogen, lower alkyl, lower alkyl substituted by halogen, lower alkoxy, lower alkoxy substituted by halogen, C(O)-lower alkyl, nitro, NR'R", cyano, S-lower alkyl, $SO_2$-lower alkyl, cycloalkyl, heterocycloalkyl, phenyloxy, benzyloxy, phenyl, NH-phenyl or heteroaryl, wherein the phenyl and heteroaryl groups are unsubstituted or substituted by one or more substituents selected from lower alkyl and halogen;
R'/R" are each independently hydrogen or lower alkyl;
$R^1$ is hydrogen or lower alkyl;
Het is a heteroaryl group selected from the group consisting of pyrimidinyl, pyridazinyl, quinolinyl, quinoxalinyl, quinazolinyl, benzooxazolyl, and benzothiazolyl, unsubstituted or substituted by one or more substituents selected from $R^3$;
$R^3$ is hydroxy, halogen, =O, lower alkyl, lower alkyl substituted by halogen, lower alkoxy, phenyl, lower alkoxy substituted by halogen, nitro, cyano, $SO_2$-lower alkyl, cycloalkyl or heterocycloalkyl;
n is 1;
or a pharmaceutically suitable acid addition salt thereof.

2. The compound of claim 1, wherein Het is benzooxazolyl, unsubstituted or substituted by one or more substituents selected from $R^3$.

3. The compound of claim 2, wherein Ar is aryl that is unsubstituted or substituted by $R^2$.

4. The compound of claim 2, wherein Ar is heteroaryl that is unsubstituted or substituted by $R^2$.

5. The compound of claim 2, selected from the group consisting of
[3-(6-chloro-benzooxazol-2-ylamino)-pyrrolidin-1-yl]-(2,6-dimethoxy-phenyl)-methanone;
[(R)-3-(6-chloro-benzooxazol-2-ylamino)-pyrrolidin-1-yl]-(2,6-dimethoxy-phenyl)-methanone;
[(R)-3-(6-chloro-benzooxazol-2-ylamino)-pyrrolidin-1-yl]-(2-pyrrol-1-yl-phenyl)-methanone;
[(R)-3-(6-chloro-benzooxazol-2-ylamino)-pyrrolidin-1-yl]-(2,6-dichloro-phenyl)-methanone;
[(R)-3-(6-chloro-benzooxazol-2-ylamino)-pyrrolidin-1-yl]-(2-chloro-6-methyl-phenyl)-methanone;
[(R)-3-(6-chloro-benzooxazol-2-ylamino)-pyrrolidin-1-yl]-(2-ethyl-phenyl)-methanone;
[(R)-3-(6-chloro-benzooxazol-2-ylamino)-pyrrolidin-1-yl]-(2-ethoxy-phenyl)-methanone;
[(R)-3-(6-chloro-benzooxazol-2-ylamino)-pyrrolidin-1-yl]-(2-methylsulfanyl-phenyl)-methanone;
[(R)-3-(6-chloro-benzooxazol-2-ylamino)-pyrrolidin-1-yl]-(2-difluoromethoxy-phenyl)-methanone;
[(R)-3-(6-chloro-benzooxazol-2-ylamino)-pyrrolidin-1-yl]-(2-furan-2-yl-phenyl)-methanone; and
[(R)-3-(6-chloro-benzooxazol-2-ylamino)-pyrrolidin-1-yl]-(5-phenyl-isoxazol-4-yl)-methanone.

6. The compound of claim 2, selected from the group consisting of
[(R)-3-(6-chloro-benzooxazol-2-ylamino)-pyrrolidin-1-yl]-[2-(2H-[1,2,4]triazol-3-yl)-phenyl]-methanone;
[(R)-3-(6-chloro-benzooxazol-2-ylamino)-pyrrolidin-1-yl]-(2-trifluoromethyl-phenyl)-methanone;
[(R)-3-(6-chloro-benzooxazol-2-ylamino)-pyrrolidin-1-yl]-(2-pyridin-3-yl-phenyl)-methanone;
[(R)-3-(6-chloro-benzooxazol-2-ylamino)-pyrrolidin-1-yl]-(5-methyl-3-phenyl-isoxazol-4-yl)-methanone;
[(R)-3-(6-chloro-benzooxazol-2-ylamino)-pyrrolidin-1-yl]-(5-methyl-2-trifluoromethyl-phenyl)-methanone;
[(R)-3-(6-chloro-benzooxazol-2-ylamino)-pyrrolidin-1-yl]-[2-(3-methyl-[1,2,4]oxadiazol-5-yl)-phenyl]-methanone;

[(R)-3-(6-chloro-benzooxazol-2-ylamino)-pyrrolidin-1-yl]-(2-thiophen-2-yl-phenyl)-methanone;
[(R)-3-(6-chloro-benzooxazol-2-ylamino)-pyrrolidin-1-yl]-(2-trifluoromethoxy-phenyl)-methanone;
[(R)-3-(6-chloro-benzooxazol-2-ylamino)-pyrrolidin-1-yl]-(2-fluoro-6-trifluoromethyl-phenyl)-methanone;
[(R)-3-(6-chloro-benzooxazol-2-ylamino)-pyrrolidin-1-yl]-(2,6-diethoxy-phenyl)-methanone; and
[(R)-3-(6-chloro-benzooxazol-2-ylamino)-pyrrolidin-1-yl]-(3'-methyl-biphenyl-2-yl)-methanone.

7. The compound of claim 2, selected from the group consisting of
[(R)-3-(6-chloro-benzooxazol-2-ylamino)-pyrrolidin-1-yl]-(2-methyl-4-phenyl-thiazol-5-yl)-methanone;
[(R)-3-(6-chloro-benzooxazol-2-ylamino)-pyrrolidin-1-yl]-(2-chloro-6-trifluoromethyl-phenyl)-methanone;
[(R)-3-(6-chloro-benzooxazol-2-ylamino)-pyrrolidin-1-yl]-[2-(1,1,2,2-tetrafluoro-ethoxy)-phenyl]-methanone;
[(R)-3-(6-chloro-benzooxazol-2-ylamino)-pyrrolidin-1-yl]-(2-thiophen-3-yl-phenyl)-methanone;
[(R)-3-(6-chloro-benzooxazol-2-ylamino)-pyrrolidin-1-yl]-(5-methyl-2-trifluoromethyl-furan-3-yl)-methanone;
[(R)-3-(6-chloro-benzooxazol-2-ylamino)-pyrrolidin-1-yl]-(2-fluoro-6-pyrrolidin-1-yl-phenyl)-methanone;
[(R)-3-(6,7-difluoro-benzooxazol-2-ylamino)-pyrrolidin-1-yl]-(2,6-dimethoxy-phenyl)-methanone;
(2,6-dimethoxy-phenyl)-[(R)-3-(6-fluoro-benzooxazol-2-ylamino)-pyrrolidin-1-yl]-methanone;
[(R)-3-(7-chloro-benzooxazol-2-ylamino)-pyrrolidin-1-yl]-(2,6-dimethoxy-phenyl)-methanone; and
(2,6-dimethoxy-phenyl)-[(R)-3-(4-methyl-benzooxazol-2-ylamino)-pyrrolidin-1-yl]-methanone.

8. The compound of claim 2, selected from the group consisting of
[(R)-3-(7-fluoro-benzooxazol-2-ylamino)-pyrrolidin-1-yl]-[2-(1,1,2,2-tetrafluoro-ethoxy)-phenyl]-methanone;
[(R)-3-(6,7-difluoro-benzooxazol-2-ylamino)-pyrrolidin-1-yl]-(2-trifluoromethoxy-phenyl)-methanone;
[(R)-3-(6,7-difluoro-benzooxazol-2-ylamino)-pyrrolidin-1-yl]-[2-(1,1,2,2-tetrafluoro-ethoxy)-phenyl]-methanone;
[(R)-3-(6,7-difluoro-benzooxazol-2-ylamino)-pyrrolidin-1-yl]-(5-methyl-2-trifluoromethyl-phenyl)-methanone;
[(R)-3-(6,7-difluoro-benzooxazol-2-ylamino)-pyrrolidin-1-yl]-(5-methyl-3-phenyl-isoxazol-4-yl)-methanone;
[(R)-3-(6,7-difluoro-benzooxazol-2-ylamino)-pyrrolidin-1-yl]-(2-methyl-5-phenyl-thiazol-4-yl)-methanone;
[(R)-3-(6-fluoro-benzooxazol-2-ylamino)-pyrrolidin-1-yl]-(2-trifluoromethoxy-phenyl)-methanone;
[(R)-3-(6-fluoro-benzooxazol-2-ylamino)-pyrrolidin-1-yl]-[2-(1,1,2,2-tetrafluoro-ethoxy)-phenyl]-methanone;
[(R)-3-(6-fluoro-benzooxazol-2-ylamino)-pyrrolidin-1-yl]-(5-methyl-2-trifluoromethyl-phenyl)-methanone; and
[(R)-3-(6-fluoro-benzooxazol-2-ylamino)-pyrrolidin-1-yl]-(2-methyl-5-phenyl-thiazol-4-yl)-methanone.

9. The compound of claim 1, wherein Het is quinoxalinyl unsubstituted or substituted by one or more substituents selected from R³.

10. The compound of claim 9, wherein Ar is aryl that is unsubstituted or substituted by R².

11. The compound of claim 9, wherein Ar is heteroaryl that is unsubstituted or substituted by R².

12. The compound of claim 9, selected from the group consisting of
(2,6-dimethoxy-phenyl)-[3-(quinoxalin-2-ylamino)-pyrrolidin-1-yl]-methanone;
(2,6-dimethoxy-phenyl)-[(R)-3-(quinoxalin-2-ylamino)-pyrrolidin-1-yl]-methanone;
[(R)-3-(6-chloro-quinoxalin-2-ylamino)-pyrrolidin-1-yl]-(2,6-dimethoxy-phenyl)-methanone;
(2,6-dimethoxy-phenyl)-[(R)-3-(6-fluoro-quinoxalin-2-ylamino)-pyrrolidin-1-yl]-methanone;
[(R)-3-(6,7-difluoro-quinoxalin-2-ylamino)-pyrrolidin-1-yl]-(2-trifluoromethyl-phenyl)-methanone;
[(R)-3-(6,7-difluoro-quinoxalin-2-ylamino)-pyrrolidin-1-yl]-(2-trifluoromethoxy-phenyl)-methanone;
[(R)-3-(6,7-difluoro-quinoxalin-2-ylamino)-pyrrolidin-1-yl]-[2-(1,1,2,2-tetrafluoro-ethoxy)-phenyl]-methanone;
[(R)-3-(6,7-difluoro-quinoxalin-2-ylamino)-pyrrolidin-1-yl]-(5-methyl-3-phenyl-isoxazol-4-yl)-methanone;
[(R)-3-(6,7-difluoro-quinoxalin-2-ylamino)-pyrrolidin-1-yl]-[2-(3-methyl-[1,2,4]oxadiazol-5-yl)-phenyl]-methanone; and
(2-chloro-5-methyl-phenyl)-[(R)-3-(6,7-difluoro-quinoxalin-2-ylamino)-pyrrolidin-1-yl]-methanone.

13. The compound of claim 9, selected from the group consisting of
[(R)-3-(6,7-difluoro-quinoxalin-2-ylamino)-pyrrolidin-1-yl]-(2-methoxy-5-methyl-phenyl)-methanone;
[(R)-3-(6,7-difluoro-quinoxalin-2-ylamino)-pyrrolidin-1-yl]-(2-methyl-5-phenyl-thiazol-4-yl)-methanone;
[(R)-3-(6-chloro-quinoxalin-2-ylamino)-pyrrolidin-1-yl]-[2-(1,1,2,2-tetrafluoro-ethoxy)-phenyl]-methanone;
[(R)-3-(6-chloro-quinoxalin-2-ylamino)-pyrrolidin-1-yl]-(5-methyl-2-trifluoromethyl-phenyl)-methanone;
[(R)-3-(6-chloro-quinoxalin-2-ylamino)-pyrrolidin-1-yl]-(5-methyl-3-phenyl-isoxazol-4-yl)-methanone;
[(R)-3-(6-chloro-quinoxalin-2-ylamino)-pyrrolidin-1-yl]-[2-(3-methyl-[1,2,4]oxadiazol-5-yl)-phenyl]-methanone;
(2-chloro-5-methyl-phenyl)-[(R)-3-(6-chloro-quinoxalin-2-ylamino)-pyrrolidin-1-yl]-methanone;
[(R)-3-(6-chloro-quinoxalin-2-ylamino)-pyrrolidin-1-yl]-(2-methyl-5-phenyl-thiazol-4-yl)-methanone; and
[(R)-3-(quinoxalin-2-ylamino)-pyrrolidin-1-yl]-(2-trifluoromethyl-phenyl)-methanone.

14. The compound of claim 9, selected from the group consisting of
[(R)-3-(quinoxalin-2-ylamino)-pyrrolidin-1-yl]-(2-trifluoromethoxy-phenyl)-methanone;
[(R)-3-(quinoxalin-2-ylamino)-pyrrolidin-1-yl]-[2-(1,1,2,2-tetrafluoro-ethoxy)-phenyl]-methanone;
(5-methyl-2-trifluoromethyl-phenyl)-[(R)-3-(quinoxalin-2-ylamino)-pyrrolidin-1-yl]-methanone;
(2-methyl-5-phenyl-thiazol-4-yl)-[(R)-3-(quinoxalin-2-ylamino)-pyrrolidin-1-yl]-methanone;
[(R)-3-(7-chloro-quinoxalin-2-ylamino)-pyrrolidin-1-yl]-[2-(1,1,2,2-tetrafluoro-ethoxy)-phenyl]-methanone;
(R)-[3-(6-tert-butyl-quinoxalin-2-ylamino)-pyrrolidin-1-yl]-(5-methyl-2-trifluoromethyl-phenyl)-methanone;
(R)-[3-(6-fluoro-quinoxalin-2-ylamino)-pyrrolidin-1-yl]-(5-methyl-2-trifluoromethyl-phenyl)-methanone;
(R)-[3-(7-chloro-6-methyl-quinoxalin-2-ylamino)-pyrrolidin-1-yl]-(5-methyl-2-trifluoromethyl-phenyl)-methanone; and
(R)-[3-(6-Chloro-7-methyl-quinoxalin-2-ylamino)-pyrrolidin-1-yl]-(5-methyl-2-trifluoromethyl-phenyl)-methanone.

15. The compound of claim 1, wherein Het is benzothiazolyl, unsubstituted or substituted by one or more substituents selected from R³.

16. The compound of claim 15, wherein Ar is aryl that is unsubstituted or substituted by $R^2$.

17. The compound of claim 15, wherein Ar is heteroaryl that is unsubstituted or substituted by $R^2$.

18. The compound of claim 15, selected from the group consisting of
[3-(6-chloro-benzothiazol-2-ylamino)-pyrrolidin-1-yl]-(2,6-dimethoxy-phenyl)-methanone;
[(R)-3-(6-chloro-benzothiazol-2-ylamino)-pyrrolidin-1-yl]-(2,6-dimethoxy-phenyl)-methanone;
[(R)-3-(4-chloro-benzothiazol-2-ylamino)-pyrrolidin-1-yl]-(2,6-dimethoxy-phenyl)-methanone;
(2,6-dimethoxy-phenyl)-[(R)-3-(6-fluoro-benzothiazol-2-ylamino)-pyrrolidin-1-yl]-methanone;
(2,6-dimethoxy-phenyl)-[(R)-3-(4-fluoro-benzothiazol-2-ylamino)-pyrrolidin-1-yl]-methanone;
(2,6-dimethoxy-phenyl)-[(R)-3-(7-fluoro-benzothiazol-2-ylamino)-pyrrolidin-1-yl]-methanone;
[(R)-3-(5,7-difluoro-benzothiazol-2-ylamino)-pyrrolidin-1-yl]-(2,6-dimethoxy-phenyl)-methanone;
[(R)-3-(6-fluoro-benzothiazol-2-ylamino)-pyrrolidin-1-yl]-(2-trifluoromethyl-phenyl)-methanone; and
[(R)-3-(6-fluoro-benzothiazol-2-ylamino)-pyrrolidin-1-yl]-(2-trifluoromethoxy-phenyl)-methanone.

19. The compound of claim 15, selected from the group consisting of
[(R)-3-(6-fluoro-benzothiazol-2-ylamino)-pyrrolidin-1-yl]-[2-(1,1,2,2-tetrafluoro-ethoxy)-phenyl]-methanone;
[(R)-3-(6-fluoro-benzothiazol-2-ylamino)-pyrrolidin-1-yl]-(5-methyl-2-trifluoromethyl-phenyl)-methanone;
[(R)-3-(6-fluoro-benzothiazol-2-ylamino)-pyrrolidin-1-yl]-(5-methyl-3-phenyl-isoxazol-4-yl)-methanone;
[(R)-3-(6-fluoro-benzothiazol-2-ylamino)-pyrrolidin-1-yl]-[2-(3-methyl-[1,2,4]oxadiazol-5-yl)-phenyl]-methanone;
(2-chloro-5-methyl-phenyl)-[(R)-3-(6-fluoro-benzothiazol-2-ylamino)-pyrrolidin-1-yl]-methanone;
[(R)-3-(6-fluoro-benzothiazol-2-ylamino)-pyrrolidin-1-yl]-(2-methyl-5-phenyl-thiazol-4-yl)-methanone;
[(R)-3-(4-fluoro-benzothiazol-2-ylamino)-pyrrolidin-1-yl]-(2-trifluoromethoxy-phenyl)-methanone;
[(R)-3-(4-fluoro-benzothiazol-2-ylamino)-pyrrolidin-1-yl]-[2-(1,1,2,2-tetrafluoro-ethoxy)-phenyl]-methanone; and
[(R)-3-(4-fluoro-benzothiazol-2-ylamino)-pyrrolidin-1-yl]-(5-methyl-2-trifluoromethyl-phenyl)-methanone.

20. The compound of claim 15, selected from the group consisting of
[(R)-3-(4-fluoro-benzothiazol-2-ylamino)-pyrrolidin-1-yl]-[2-(3-methyl-[1,2,4]oxadiazol-5-yl)-phenyl]-methanone;
[(R)-3-(5,7-difluoro-benzothiazol-2-ylamino)-pyrrolidin-1-yl]-[2-(1,1,2,2-tetrafluoro-ethoxy)-phenyl]-methanone;
[(R)-3-(5,7-difluoro-benzothiazol-2-ylamino)-pyrrolidin-1-yl]-(5-methyl-3-phenyl-isoxazol-4-yl)-methanone;
[(R)-3-(5,7-difluoro-benzothiazol-2-ylamino)-pyrrolidin-1-yl]-[2-(3-methyl-[1,2,4]oxadiazol-5-yl)-phenyl]-methanone;
[(R)-3-(5,6-difluoro-benzothiazol-2-ylamino)-pyrrolidin-1-yl]-(5-methyl-2-trifluoromethyl-phenyl)-methanone; and
(R)-[3-(4-chloro-benzothiazol-2-ylamino)-pyrrolidin-1-yl]-(5-methyl-2-trifluoromethyl-phenyl)-methanone.

21. The compound of claim 1, wherein Het is pyrimidinyl, unsubstituted or substituted by one or more substituents selected from $R^3$.

22. The compound of claim 21, wherein Ar is aryl that is unsubstituted or substituted by $R^2$.

23. The compound of claim 21, wherein Ar is heteroaryl that is unsubstituted or substituted by $R^2$.

24. The compound of claim 21, wherein the compound is (5-methyl-2-trifluoromethyl-phenyl)-[(R)-3-(2-phenyl-pyrimidin-4-ylamino)-pyrrolidin-1-yl]-methanone.

25. A pharmaceutical composition comprising a therapeutically effective amount of a compound of formula I

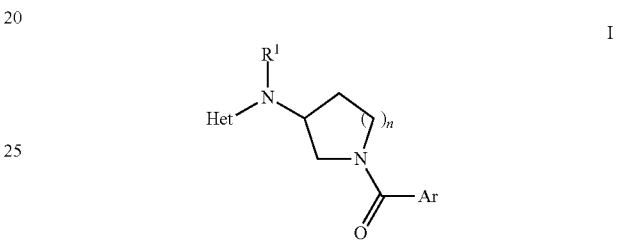

wherein
Ar is an unsubstituted or substituted aryl or heteroaryl group, wherein the substituted aryl and heteroaryl groups are substituted by one or more substituents $R^2$;
$R^2$ is hydroxy, halogen, lower alkyl, lower alkyl substituted by halogen, lower alkoxy, lower alkoxy substituted by halogen, C(O)-lower alkyl, nitro, NR'R", cyano, S-lower alkyl, SO$_2$-lower alkyl, cycloalkyl, heterocycloalkyl, phenyloxy, benzyloxy, phenyl, NH-phenyl or heteroaryl, wherein the phenyl and heteroaryl groups are unsubstituted or substituted by one or more substituents selected from lower alkyl and halogen;
R'/R" are each independently hydrogen or lower alkyl;
$R^1$ is hydrogen or lower alkyl;
Het is a heteroaryl group selected from the group consisting of pyrimidinyl, pyridazinyl, quinolinyl, quinoxalinyl, quinazolinyl, benzooxazolyl, and benzothiazolyl, unsubstituted or substituted by one or more substituents selected from $R^3$;
$R^3$ is hydroxy, halogen, =O, lower alkyl, lower alkyl substituted by halogen, lower alkoxy, phenyl, lower alkoxy substituted by halogen, nitro, cyano, SO$_2$-lower alkyl, cycloalkyl or heterocycloalkyl;
n is 1;
or a pharmaceutically suitable acid addition salt thereof and a pharmaceutically acceptable carrier.

* * * * *